(12) United States Patent
Kahvejian et al.

(10) Patent No.: US 10,568,910 B2
(45) Date of Patent: Feb. 25, 2020

(54) COMPOSITIONS AND METHODS RELATED TO ENGINEERED ERYTHROID CELLS COMPRISING IL-15

(71) Applicant: RUBIUS THERAPEUTICS, INC., Cambridge, MA (US)

(72) Inventors: Avak Kahvejian, Lexington, MA (US); Jordi Mata-Fink, Baltimore, MD (US); Robert J. Deans, Riverside, CA (US); Tiffany F. Chen, Cambridge, MA (US); John Round, Cambridge, MA (US); Noubar B. Afeyan, Lexington, MA (US); Torben Straight Nissen, Chestnut Hill, MA (US); Nathan Dowden, Winchester, MA (US); Tom Wickham, Groton, MA (US); Sivan Elloul, Newton, MA (US)

(73) Assignee: RUBIUS THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/906,873

(22) Filed: Feb. 27, 2018

(65) Prior Publication Data
US 2018/0193385 A1 Jul. 12, 2018

Related U.S. Application Data

(63) Continuation of application No. 15/716,141, filed on Sep. 26, 2017, now Pat. No. 10,456,421, which is a continuation of application No. PCT/US2017/013035, filed on Jan. 11, 2017.

(60) Provisional application No. 62/420,973, filed on Nov. 11, 2016, provisional application No. 62/370,915, filed on Aug. 4, 2016, provisional application No. 62/359,448, filed on Jul. 7, 2016, provisional application No. 62/277,130, filed on Jan. 11, 2016.

(51) Int. Cl.
| | |
|---|---|
| *A61K 35/18* | (2015.01) |
| *A61K 35/12* | (2015.01) |
| *A61K 38/19* | (2006.01) |
| *A61K 39/00* | (2006.01) |
| *A61K 39/395* | (2006.01) |
| *C12N 5/078* | (2010.01) |
| *A61P 17/00* | (2006.01) |
| *C07K 14/705* | (2006.01) |

(52) U.S. Cl.
CPC .............. *A61K 35/18* (2013.01); *A61K 35/12* (2013.01); *A61K 38/191* (2013.01); *A61K 39/0011* (2013.01); *A61K 39/3955* (2013.01); *A61P 17/00* (2018.01); *C07K 14/705* (2013.01); *C12N 5/0641* (2013.01); *A61K 2039/505* (2013.01); *A61K 2039/515* (2013.01); *C07K 2319/00* (2013.01); *C12N 2510/00* (2013.01)

(58) Field of Classification Search
CPC .................................................... A61K 35/18
See application file for complete search history.

(56) References Cited

U.S. PATENT DOCUMENTS

| | | | |
|---|---|---|---|
| 5,674,704 A | 10/1997 | Goodwin et al. | |
| 6,462,189 B1 | 10/2002 | Koide | |
| 6,673,901 B2 | 1/2004 | Koide | |
| 7,462,485 B2 | 12/2008 | Glaser | |
| 8,124,084 B2 * | 2/2012 | Lefrancois | C07K 14/5443 424/134.1 |
| 8,211,656 B2 | 7/2012 | Hyde et al. | |
| 8,617,840 B2 | 12/2013 | Godfrin | |
| 8,852,880 B2 | 10/2014 | Godfrin | |
| 8,974,802 B2 | 3/2015 | Dufour et al. | |
| 9,125,876 B2 | 9/2015 | Godfrin et al. | |
| 9,364,504 B2 | 6/2016 | Godfrin et al. | |
| 9,644,180 B2 | 5/2017 | Kahvejian et al. | |
| 10,253,296 B2 | 4/2019 | Kahvejian et al. | |
| 10,301,593 B2 | 5/2019 | Kahvejian et al. | |
| 10,301,594 B1 | 5/2019 | Kahvejian et al. | |
| 10,329,531 B2 | 6/2019 | Kahvejian et al. | |
| 10,344,263 B2 | 7/2019 | Kahvejian et al. | |
| 2002/0151004 A1 | 10/2002 | Craig | |
| 2006/0188490 A1 | 8/2006 | Hoerr et al. | |
| 2010/0041014 A1 | 2/2010 | Hyde et al. | |
| 2010/0316620 A1 | 12/2010 | Bourgeaux et al. | |
| 2012/0129210 A1 | 5/2012 | Bourgeaux et al. | |
| 2012/0207745 A1 | 8/2012 | Godfrin et al. | |
| 2014/0363413 A1 | 12/2014 | Bourgeaux et al. | |
| 2015/0086521 A1 | 3/2015 | Godfrin | |
| 2015/0118265 A1 | 4/2015 | Edinger et al. | |
| 2015/0182588 A1 | 7/2015 | Kahvejian et al. | |
| 2015/0306212 A1 | 10/2015 | Kahvejian et al. | |
| 2016/0082046 A1 | 3/2016 | Lodish et al. | |
| 2016/0095884 A1 | 4/2016 | Godfrin et al. | |
| 2016/0120956 A1 | 5/2016 | Godfrin et al. | |
| 2016/0122707 A1 | 5/2016 | Swee et al. | |
| 2016/0257932 A1 | 9/2016 | Kahvejian et al. | |
| 2016/0361361 A1 | 12/2016 | Godfrin et al. | |
| 2017/0020926 A1 | 1/2017 | Mata-Fink et al. | |
| 2017/0369843 A1 | 12/2017 | Kahvejian et al. | |

(Continued)

FOREIGN PATENT DOCUMENTS

| | | |
|---|---|---|
| CN | 103224957 A | 7/2013 |
| WO | 2007030708 A2 | 3/2007 |

(Continued)

OTHER PUBLICATIONS

Shi et. al. PNAS 2014;111:10131-5.*

(Continued)

*Primary Examiner* — Scott Long
(74) *Attorney, Agent, or Firm* — Lando & Anastasi, LLP

(57) ABSTRACT

The invention includes compositions and methods related to multimodal therapies, e.g., for treating a cancer. A multimodal therapy described herein provides and/or administers a plurality of agents that function in a coordinated manner to provide a therapeutic benefit to a subject in need thereof, e.g., a subject having a cancer.

18 Claims, 6 Drawing Sheets

Specification includes a Sequence Listing.

(56) References Cited

U.S. PATENT DOCUMENTS

| | | |
|---|---|---|
| 2018/0030411 A1 | 2/2018 | Kahvejian et al. |
| 2018/0085402 A1 | 3/2018 | Kahvejian et al. |
| 2018/0119101 A1 | 5/2018 | Kahvejian et al. |
| 2018/0135012 A1 | 5/2018 | Mata-Fink et al. |
| 2018/0153989 A1 | 6/2018 | Kahvejian et al. |
| 2018/0187153 A1 | 7/2018 | Kahvejian et al. |
| 2018/0187154 A1 | 7/2018 | Kahvejian et al. |
| 2018/0187155 A1 | 7/2018 | Kahvejian et al. |
| 2018/0208897 A1 | 7/2018 | Kahvejian et al. |
| 2018/0216067 A1 | 8/2018 | Kahvejian et al. |
| 2018/0265847 A1 | 9/2018 | Kahvejian et al. |
| 2018/0271910 A1 | 9/2018 | Mata-Fink et al. |
| 2018/0280440 A1 | 10/2018 | Lodish et al. |
| 2018/0344770 A1 | 12/2018 | Wickham et al. |
| 2019/0062788 A1 | 2/2019 | Harandi et al. |
| 2019/0083540 A1 | 3/2019 | Kahvejian et al. |
| 2019/0160102 A1 | 5/2019 | Hoffman et al. |
| 2019/0161730 A1 | 5/2019 | Kahvejian et al. |
| 2019/0201548 A1 | 7/2019 | Kahvejian et al. |
| 2019/0247440 A1 | 8/2019 | Mata-Fink et al. |
| 2019/0264177 A1 | 8/2019 | Kahvejian et al. |

FOREIGN PATENT DOCUMENTS

| | | | | |
|---|---|---|---|---|
| WO | 2014183066 A2 | 11/2014 | | |
| WO | 2014183071 A2 | 11/2014 | | |
| WO | WO2014/183071 | * | 11/2014 | ............ A61K 35/18 |
| WO | 2015073587 A2 | 5/2015 | | |
| WO | 2015153102 A1 | 10/2015 | | |
| WO | 2016183482 A1 | 11/2016 | | |
| WO | 2017114966 A1 | 7/2017 | | |
| WO | 2017123644 A1 | 7/2017 | | |
| WO | 2017123646 A1 | 7/2017 | | |
| WO | 2018009838 A1 | 1/2018 | | |

OTHER PUBLICATIONS

Shook et al. Tissue Antigens 2011;78:409-15.*
Kurpad et al. J Hematother Stem Cell Res 1999;8:585-92.*
Bessard et al. Mol Cancer Ther 2009;8:2736-45.*
Jakobisiak et al. (Cytokine & Growth Factor Reviews 22 (2011) 99-108). (Year: 2011).*
Shi et al. (PNAS. Jul. 15, 2014; 111(28) 10131-10136) (Year: 2014).*
Kermer et al. (Mol Cancer Ther; Jan. 2014; 13(1): 112-121) (Year: 2014).*
Beavis et al. "Reprogramming the tumor microenvironment to enhance adoptive cellular therapy" Seminars in Immunology (2016) vol. 28, pp. 64-72.
Buchsbaum et al. "TRAIL-receptor antibodies as potential cancer treatment" Future Oncol. (2007) vol. 3, No. 4, pp. 405-409.
Chester et al. "Natural Killer Cell Immunomodulation: Targeting Activating, Inhibitory, and Co-stimulatory Receptor Signaling for Cancer Immunotherapy" Frontiers in Immunology (2015) vol. 6, No. 601, pp. 1-9.
Gasparian et al. "Generation of new TRAIL mutants DR5-A and DR5-B with improved selectivity to death receptor 5" Apoptosis (2009) vol. 14, pp. 778-787.
Hu et al. "Isolation and functional characterization of human erythroblasts at distinct stages: implications for understanding of normal and disordered erythropoiesis in vivo" Blood (2013) vol. 121, No. 16, pp. 3246-3253.
International Search Report and Written Opinion for International Application No. PCT/US2017/013033 dated May 15, 2017.
International Search Report and Written Opinion for International Application No. PCT/US2017/013035 dated Apr. 28, 2017.
Johnson et al. "Membrane Proteins—Molecular Biology of the Cell" NCBI Bookshelf 2002, pp. 1-18; www.ncbi.nlm.nih.gov/books/NBK26878.
Kim et al. "A Chemically Cross-Linked Knottin Dimer Binds Integrins eith Picomolar Affinity and Inhibits Tumor Cell Migration and Proliferation" JACS (2015) vol. 137, pp. 6-9.
Lienert et al. "Synthetic biology in mammalian cells: next generation research tools and therapeutics" Nature Reviews, Molecular Cell Biology (2014) vol. 15, pp. 95-107.
Marconi et al. "Constitutive localization of DR4 in lipid rafts is mandatory for TRAIL-induced apoptosis in B-cell hematologic malignancies" Cell Death and Disease (2013) vol. 4, e863, pp. 1-13.
Mohr et al. "TRAIL-receptor preferences in pancreatic cancer cells revisited: Both TRAIL-R1 and TRAIL-R2 have a licence to kill" BMC Cancer (2015) vol. 15, No. 494, pp. 1-11.
Muzykantov et al. "Drug delivery by red blood cells: vascular carriers designed by Mother Nature" Expert Opin Drug Deilv. (2010) vol. 7, No. 4, pp. 403-427.
Tan et al. "A quantatative analysis of therapeutic cancer vaccines in phase 2 or phase 3 trial" (2015) vol. 3, No. 48, pp. 1-12.
Tan et al. "Cell or Cell Membrane-Based Drug Delivery Systems" Theranostics (2015) vol. 5, No. 8, pp. 863-881.
Vezys et al., "4-1BB Signaling Synergizes with Programmed Death Ligand 1 Blackade to Augment CD8 T Cell Responses during Chronic Viral Infection," J Immunol (2011) vol. 187, pp. 1634-1642.
Bernard et al., "Packed Red Blood Cells suppress T-Cell Proliferation Through a Process Involving Cell-Cell Contact," Journal of Trauma (2010) vol. 69, No. 2, pp. 320-329.
Castillo et al., "Regulating the Immune system via IL-15 Transpresentation," Cytokine (2012) vol. 59, No. 3, pp. 479-490.
Cooley et al., "Trans-presentation of IL-15 modulates STAT5 activation and Bcl-6 expression in TH1 cells," Sci Rep (2015) vol. 5, Article 15722, 9 pages.
Fabbi et al., "Dual Roles of IL-15 in Cancer Biology," J Cytokine Biol (2016) vol. 1, Issue 2, Article 1000103, 7 pages.
Fehniger at al., "Interleukin 15: biology and relevance to human disease," Blood (2001) vol. 97, No. 1, pp. 14-32.
Feng et al., "Prediction of Membrane Protein Types Based no The Hydrophobic Index of Amino Acids," J Protein Chem (2000) vol. 19, No. 4, pp. 369-375.
SenCore, sequence No. 9 search result, Jan. 2018.
Hornig et al., "Evaluating combinations of costimulatory antibody-ligand fusion proteins for targeted cancer Immunotherapy," Cancer Immunol Immunother (2013) vol. 62, pp. 1369-1380.
Kim et al., "Matrix Metalloproteinases, New Insights into the Understanding of Neurogenerative Disorders," Biomol Ther (2012) vol. 20, No. 2 pp. 133-143.
Kokaji et al., "IL-15 Transpresentation Augments CD8+ T Cell Activation and Is Required for Optimal Recall Responses by Central Memory CD8+ T Cells," J Immunol (2008) vol. 180, pp. 4391-4401.
Mullarky et al., "Gamma Interferon Suppresses Erythropoiesis via Interleukin-15," Infection and Immunity (2007) vol. 75, No. 5, pp. 2630-2633.
Otegbeye et al., "The IL-15 Super-Agonist ALT-803 Promotes Superior Activation and Cytotoxicity of Ex Vivo Expanded NK Cells Against AML," Blood (2015) vol. 126, Issue 23, p. 3090.
Perdreau et al., "Different dynamics of IL-15R activation following IL-15 cis- or trans-presentation," Eur Cytokine Rev (2010) vol. 21, No. 4, pp. 297-307.
Sato et al., "The IL-15/IL-15Ra on cell surfaces enables sustained IL-15 activity and contributes to the long survival of CD8 memory T cells," PNAS (2007) vol. 104, No. 2, pp. 588-593.
Sinclair, "Erythropoiesis stimulating agents: approaches to modulate activity," Biologics: Targets and Therapy (2013) vol. 7, pp. 161-174.
Stonier et al., "Trans-presentation: a novel mechanism regulating IL-15 and responses," Immunol Lett (2010) vol. 127, No. 2, pp. 85-92.
Tamzalit et al., "IL-15.IL-15Ra complex shedding following transpresentation is essential for the survival of IL-15 responding NK and T cells," PNAS (2014) vol. 111, No. 23, pp. 8565-8570.
Ui et al., "Grafting synthetic transmembrane units to the engineered low-toxicity a-hemolysin to restore its hemolytic activity," Mol Bio Syst (2014) vol. 10, pp. 3199-3206.
U.S. Appl. No. 16/207,568, filed Dec. 3, 2018.
Cheuk et al., "Role of 4-1BB:4-1BB ligand in cancer immunotherapy," Cancer Gene Therapy (2004) vol. 11, pp. 215-226.

(56) References Cited

OTHER PUBLICATIONS

Declaration by Dr. Stephen Smiley as filed in U.S. Appl. No. 12/005,767 dated Jul. 16, 2010.
Bu et al., "Familial Atypical Hemolytic Uremic Syndrome: A Review of Its Genetic and Clinical Aspects," Clin Dev Immunol (2012) Article 370426, 9 pages.
Dasgupta et al., "Isopeptide Ligation Catalyzed by Quintessential Sortase A: Mechanistic Cues from Cyclic and Branched Oligomers of Indolicidin," J Biol Chem (2011) vol. 286, No. 27, pp. 23996-24006.
Pasini et al., "In-depth analysis of the membrane and cytosolic proteome of red blood cells," Blood (2006) vol. 108, pp. 791-801.
Shao et al., "Membrane Protein Insertion at the Endoplasmic Reticulum," Annu Rev Cell Dev Biol (2011) vol. 27, pp. 25-56.
Swee et al.,"One-Step Enzymatic Modification of the Cell Surface Redirects Cellular Cytotoxicity and Parasite Tropism," ACS Chem Biol (2015) vol. 10, pp. 460-465.

* cited by examiner

Targeting and enzyme

Targeting and capture

Targeting and promoting activity

Cell specific targeting and promoting activity

COMPOSITIONS AND METHODS RELATED TO ENGINEERED ERYTHROID CELLS COMPRISING IL-15

RELATED APPLICATIONS

This application is a continuation of U.S. Ser. No. 15/716,141, filed Sep. 26, 2017, which is a continuation of International Application No. PCT/US2017/013035, filed Jan. 11, 2017, which claims priority to U.S. Ser. No. 62/277,130 filed Jan. 11, 2016, U.S. Ser. No. 62/359,448 filed Jul. 7, 2016, U.S. Ser. No. 62/370,915 filed Aug. 4, 2016, and U.S. Ser. No. 62/420,973 filed Nov. 11, 2016, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 6, 2017, is named R2081-702020FT-_SL.txt and is 24,595 bytes in size.

BACKGROUND

Red blood cells have been considered for use as drug delivery systems, e.g., to degrade toxic metabolites or inactivate xenobiotics, and in other biomedical applications.

SUMMARY OF THE INVENTION

The invention includes compositions and methods related to multimodal therapies. The therapies are useful, e.g., for treating cancer. A multimodal therapy described herein provides and/or administers a plurality of agents that function in a coordinated manner to provide a therapeutic benefit to a subject in need thereof, e.g., a subject having a cancer. In general, a multimodal therapy described herein includes the administration to a subject of a preparation of engineered red blood cells, e.g., enucleated red blood cells, comprising (e.g., expressing or containing) a plurality of agents (e.g., polypeptides) that function in a coordinated manner (e.g., agent-additive, agent-synergistic, multiplicative, independent function, localization-based, proximity-dependent, scaffold-based, multimer-based, or compensatory).

In some aspects, the present disclosure provides an enucleated red blood cell, e.g., a reticulocyte, comprising a plurality of agents, e.g., a plurality of polypeptides (e.g., exogenous polypeptides), e.g., a first exogenous polypeptide, a second exogenous polypeptide, and a third exogenous polypeptide.

In some aspects, the present disclosure provides an enucleated red blood cell, e.g., a reticulocyte, comprising a plurality of exogenous polypeptides, wherein a first and a second exogenous polypeptide of the plurality have agent-additive, agent-synergistic, multiplicative, independent function, localization-based, proximity-dependent, scaffold-based, multimer-based, or compensatory activity.

In some aspects, the present disclosure provides an enucleated red blood cell, e.g., a reticulocyte, comprising a first exogenous polypeptide and a second exogenous polypeptide, wherein:

a) the first and second exogenous polypeptides act on the same target, wherein optionally the target is a cell surface receptor and/or an endogenous human protein;

b) the first exogenous polypeptide binds to a first endogenous human protein and the second exogenous polypeptide binds to a second endogenous human target protein, e.g., with a Kd of less than 500, 200, 100, 50, 20, 10, 5, 2, or 1 nM;

c) the first exogenous polypeptide acts on (e.g., binds) a first target, and the second exogenous polypeptide act on (e.g., binds) a second target, wherein the first and second targets are members of the same biological pathway, wherein optionally the targets are cell surface receptors, endogenous human proteins, or both;

d) the first exogenous polypeptide comprises a first pro-apoptotic polypeptide and the second exogenous polypeptide comprises a second pro-apoptotic polypeptide, e.g., a TRAIL receptor ligand, e.g., a TRAIL polypeptide;

e) the first and second exogenous polypeptides are in close proximity to each other, e.g., are less than 10, 7, 5, 4, 3, 2, 1, 0.5, 0.2, or 0.1 nm apart for a duration of at least 1, 2, 5, 10, 30, or 60 seconds; 1, 2, 5, 10, 30, or 60 minutes, or 1, 2, 3, 6, 12, or 14 hours;

f) the first and second exogenous polypeptides have a Kd of less than 500, 200, 100, 50, 20, 10, 5, 2, or 1 nM for each other;

g) the first exogenous polypeptide comprises an antigen-presenting polypeptide, e.g., an MHC molecule, e.g., an MHC class II molecule, and the second exogenous polypeptide comprises an antigen, e.g., a cancer antigen;

h) the first and second exogenous polypeptides act on different targets, wherein optionally at least one of the targets is a cell surface receptor and/or an endogenous human protein, e.g., the first exogenous polypeptide binds a first cell type, e.g., a cancer cell, and the second exogenous polypeptide binds a second cell type, e.g., an immune effector cell, e.g., a T cell;

i) the first exogenous polypeptide and the second exogenous polypeptide have an abundance ratio of about 1:1, from about 2:1 to 1:2, from about 5:1 to 1:5, from about 10:1 to 1:10, from about 20:1 to 1:20, from about 50:1 to 1:50, from about 100:1 to 1:100 by weight or by copy number;

j) the first exogenous polypeptide and the second exogenous polypeptide have a Kd for a first target and a second target, respectively, with a ratio of about 1:1, from about 2:1 to 1:2, from about 5:1 to 1:5, from about 10:1 to 1:10, from about 20:1 to 1:20, from about 50:1 to 1:50, from about 100:1 to 1:100;

k) the first exogenous polypeptide has a first activity (e.g., binding) towards a first target, and the second exogenous polypeptide has a second activity (e.g., binding) towards the first target, e.g., the first and second exogenous polypeptides bind a single target;

l) the first exogenous polypeptide acts on (e.g., binds) a first target and the second exogenous polypeptide acts on (e.g., binds) a second target, and the first and second targets are part of the same pathway, wherein optionally the first exogenous polypeptide acts on the first target and the second exogenous polypeptide acts on the second target simultaneously;

m) the first exogenous polypeptide acts on (e.g., binds) a first target and the second exogenous polypeptide acts on (e.g., binds) a second target, and the first and second targets are part of different pathways, wherein optionally the first and second pathways both act to promote a given cellular response;

n) the first exogenous polypeptide localizes the enucleated red blood cell to a desired site, e.g., a human cell, and the second exogenous polypeptide has a therapeutic activity, e.g., an immunomodulation activity such as a T cell activation activity or antigen presenting activity (e.g., for a cancer vaccine);

o) the first exogenous polypeptide binds a first target, e.g., a first cell, e.g., a first cell type, e.g., a cancer cell, and the second exogenous polypeptide binds a second target, e.g., a second cell, e.g., a second cell type, e.g., an immune effector cell, e.g., a T cell;

p) the first exogenous polypeptide and the second exogenous polypeptide are non-human proteins;

q) the first exogenous polypeptide and the second exogenous polypeptide are both enzymes, e.g., biosynthetic enzymes;

r) the first exogenous polypeptide promotes formation of an intermediate molecule and the second exogenous polypeptide acts on the intermediate molecule; or s) the first exogenous polypeptide and the second exogenous polypeptide act on successive steps of a pathway.

Any of the aspects herein, e.g., the aspects above, can be characterized by one or more of the embodiments herein, e.g., the embodiments below.

In some embodiments, the exogenous polypeptides have synergistic activity. In some embodiments, the exogenous polypeptides have additive activity.

In some embodiments, the exogenous polypeptides have proximity-dependent activity.

The proximity between the plurality of polypeptides, before, during, or after, interaction with a target moiety or moieties, may confer a property or result which is not seen in the absence of such proximity in vivo or in vitro.

In some embodiments, the first exogenous polypeptide interacts with, e.g., binds, a first target moiety, e.g., a first target cell polypeptide on a target cell (e.g., an immune effector cell, e.g., a T cell), and the second exogenous polypeptide interacts with, e.g., binds, a second target moiety, e.g., a second target cell polypeptide on the target cell (e.g., wherein binding of the first and second target cell polypeptide alters a biological property of the target cell). In an embodiment the first and second targets are subunits of a multimeric complex on the target cell.

In some embodiments, the first exogenous polypeptide promotes fusion of the red blood cell with a target cell and the second exogenous polypeptide is a polypeptide of any of Table 1, Table 2, or Table 3 (e.g., a human polypeptide of any of Table 1, Table 2, Table 3, or Table 4, e.g., a polypeptide having the amino acid sequence of the human wild type polypeptide).

In some embodiments the first and second exogenous polypeptides interact with one another, e.g., the first modifies, e.g., by cleavage or phosphorylation, the second, or the first and second form a dimeric or multimeric protein.

In some embodiments, the enucleated red blood cell comprises 3, 4, 5, 6, 7, 8, 9, or 10 different exogenous polypeptides. In an embodiment a plurality (e.g., 2, 3, 4, 5, 6, 7, 8, 9, or 10), or all, of the different exogenous polypeptides, have a preselected level of homology to each other, e.g., at least 40, 50, 60, 70, 75, 80, 85, 90, 95, 96, 97, 98, 99, or 99.5% sequence identity to each other. In an embodiment a plurality (e.g., 2, 3, 4, 5, 6, 7, 8, 9, or 10), or all, of the different exogenous polypeptides, have a preselected level of homology to a reference sequence, e.g., at least 40, 50, 60, 70, 75, 80, 85, 90, 95, 96, 97, 98, 99, 99.5%, or 100% sequence identity with a reference sequence (which reference sequence, includes an entire polypeptide sequence, or a portion thereof, e.g., a preselected domain), e.g., a plurality or all of the different exogenous polypeptides are antibodies or antibody molecules. In some embodiments, the reference sequence is an antibody sequence or fragment thereof. In some embodiments, the reference sequence comprises a heavy chain constant region or portion thereof, light chain constant region or fragment thereof, heavy chain variable region or portion thereof, light chain variable region or fragment thereof, or any combination of the foregoing.

In some embodiments, the enucleated red blood cell comprises at least 2 but no more than 5, 6, 7, 8, 9, or 10 different exogenous polypeptides, e.g., exogenous polypeptides that are encoded by one or more exogenous nucleic acids that are not retained by the enucleated red blood cell.

In some embodiments, the exogenous polypeptides are encoded by one or more exogenous nucleic acids that are not retained by the enucleated red blood cell.

In some embodiments, one or more (e.g., two or three) of the first, second, and optionally third exogenous polypeptides are transmembrane polypeptides or surface-anchored polypeptides.

In some embodiments, the first exogenous polypeptide interacts with, e.g., binds, a moiety on a target cell, and the second exogenous polypeptide alters a property of the target cell, e.g., kills or activates the target cell.

In some embodiments, the first exogenous polypeptide and the second exogenous polypeptide have an abundance ratio of about 1:1, from about 2:1 to 1:2, from about 5:1 to 1:5, from about 10:1 to 1:10, from about 20:1 to 1:20, from about 50:1 to 1:50, or from about 100:1 to 1:100 by weight or by copy number. In some embodiments, both the first and second polypeptides have a stoichiometric mode of action, or both have a catalytic mode of action, and both are present at a similar abundance, e.g., about 1:1 or from about 2:1 to 1:2. In some embodiments, the first exogenous polypeptide is more abundant than the second exogenous polypeptide by at least about 10%, 20%, 30%, 50%, or a factor of 2, 3, 4, 5, 10, 20, 50, or 100 (and optionally up to 10 or 100 fold) by weight or copy number. In some embodiments, the second exogenous polypeptide is more abundant than the first exogenous polypeptide by at least about 10%, 20%, 30%, 50%, or a factor of 2, 3, 4, 5, 10, 20, 50, or 100 (and optionally up to 10 or 100 fold) by weight or copy number. In some embodiments, the first polypeptide has a stoichiometric mode of action and the second polypeptide has a catalytic mode of action, and the first polypeptide is more abundant than the second polypeptide. In some embodiments, the second polypeptide has a stoichiometric mode of action and the first polypeptide has a catalytic mode of action, and the second polypeptide is more abundant than the first polypeptide.

In some embodiments, the first exogenous polypeptide comprises a targeting moiety.

In some embodiments, the enucleated red blood cell has one or more of the following characteristics:

a) an osmotic fragility of less than 50% cell lysis at 0.3%, 0.35%, 0.4%, 0.45%, or 0.5% NaCl;

b) a cell volume of about 10-200 fL or a cell diameter of between about 1 micron and about 20 microns, between about 2 microns and about 20 microns, between about 3 microns and about 20 microns, between about 4 microns and about 20 microns, between about 5 microns and about 20 microns, between about 6 microns and about 20 microns, between about 5 microns and about 15 microns, or between about 10 microns and about 30 microns;

c) greater than 1%, 2%, 3%, 4%, 5%, 6%, 7%, 8%, 9% or 10% fetal hemoglobin; or at least about 20, 25, or 30 pg/cell of hemoglobin; or d) phosphatidylserine content of the outer leaflet is less than 30%, 25%, 20%, 15%, 10%, or 5% as measured by Annexin V staining.

In some embodiments, at least one, e.g., all, of the plurality of exogenous polypeptides are glycosylated. In some embodiments, at least one, e.g., all, of the plurality of exogenous polypeptides are phosphorylated.

In some embodiments, the enucleated red blood cell is a reticulocyte.

In some embodiments, the exogenous polypeptide or polypeptides lack a sortase transfer signature (i.e., a sequence that can be created by a sortase reaction) such as LPXTG (SEQ ID NO: 17).

In some aspects, the present disclosure provides a method of treating a disease or condition described herein, comprising administering to a subject in need thereof an enucleated red blood cell, e.g., a reticulocyte, described herein. In some embodiments, the disease or condition is a cancer, e.g., a cancer described herein.

In some aspects, the present disclosure provides a method of bringing into proximity a first and a second cell surface moiety, e.g., transmembrane receptors, comprising administering to a subject in need thereof an enucleated red blood cell, e.g., a reticulocyte, described herein.

In some aspects, the present disclosure provides a method of delivering, presenting, or expressing a plurality of proximity-dependent molecules comprising providing an enucleated red blood cell, e.g., a reticulocyte, described herein.

In some aspects, the present disclosure provides a method of producing an enucleated red blood cell, e.g., a reticulocyte, described herein, providing contacting a red blood cell precursor with one or more nucleic acids encoding the exogenous polypeptides and placing the cell in conditions that allow enucleation to occur.

In some aspects, the present disclosure provides a preparation, e.g., pharmaceutical preparation, comprising a plurality of enucleated red blood cells, e.g., reticulocytes, described herein, e.g., at least $10^8$, $10^9$, $10^{10}$, $10^{11}$, or $10^{12}$ cells.

In some aspects, the present disclosure provides a cell complex, e.g., an in vitro or in vivo complex, of an engineered red blood cell (RBC), e.g., an enucleated red blood cell, e.g., a reticulocyte, and a target cell, the complex mediated by one of the exogenous polypeptides. In some embodiments, the cell complex comprises at least 2, 3, 4, 5, 10, 20, 50, or 100 cells. In some embodiments, the cell complex comprises at least two cell types in addition to the engineered RBC, e.g., a cancer cell and an immune effector cell.

In some aspects, the present disclosure proves a reaction mixture comprising an engineered RBC, e.g., an enucleated red blood cell, e.g., a reticulocyte, and nucleic acid, e.g., one or more nucleic acid molecules, encoding a multimodal pair described herein. In some embodiments, the nucleic acid comprises at least one promoter that is active in a red blood cell.

In some embodiments, nucleic acid encodes at least two proteins described herein (e.g., in Table 1, Table 2, and Table 3). In some embodiments, the nucleic acid encodes a third exogenous polypeptide.

In some aspects, the present disclosure comprises a method of making an engineered RBC (e.g., an enucleated red blood cell, e.g., a reticulocyte) described herein, comprising: providing, e.g., receiving, information about a target cell or subject, responsive to that information selecting a plurality of exogenous polypeptides, and introducing nucleic acids encoding the exogenous polypeptides into a RBC or RBC precursor.

In some aspects, the present invention comprises a method of evaluating an engineered erythroid cell, e.g., RBC (e.g., enucleated RBC, e.g., a reticulocyte), comprising providing a candidate erythroid cell, e.g., RBC, and determining if nucleic acid encoding a plurality of exogenous polypeptides, e.g., a multimodal pair of the exogenous polypeptides, are present.

In some aspects, the present invention comprises a method of evaluating an engineered erythroid cell, e.g., RBC (e.g., enucleated RBC, e.g., a reticulocyte), comprising providing a candidate erythroid cell, e.g., RBC, and determining if a plurality of exogenous polypeptides, e.g., a multimodal pair of exogenous polypeptides, are present, e.g., by protein detection.

The present disclosure provides, in some aspects, an enucleated erythroid cell comprising:
a first exogenous polypeptide that interacts with a target, and
a second exogenous polypeptide that modifies the target;
wherein one or more of:
(a) the second exogenous polypeptide comprises a moiety that cleaves an antibody, e.g., that cleaves at a hinge region, a CH2 region, or between a hinge and CH2 region, e.g., an IdeS polypeptide;
(b) the second exogenous polypeptide comprises an enzyme (e.g., a protease) that modifies, e.g., is specific, e.g., binds to a site on target, binds (e.g., specifically) and modifies, e.g., covalently modifies, e.g., cleaves, or removes or attaches a moiety to, the target; (c) the second exogenous polypeptide comprises a polypeptide, e.g., an enzyme, e.g., a protease, that modifies the secondary, tertiary, or quaternary structure of the target, and, in embodiments, alters, e.g., decreases or increases, the ability of the target to interact with another molecule, e.g., the first exogenous polypeptide or a molecule other than the first exogenous polypeptide, wherein optionally the target comprises an antibody, or complement factor;
(d) the second exogenous polypeptide comprises a polypeptide, e.g., an enzyme (e.g., a protease) that cleaves the target, e.g., a polypeptide, between a first target domain and a second target domain, e.g., a first target domain that binds a first substrate and a second target domain that binds a second substrate;
(e) the target is a polypeptide, a carbohydrate (e.g., a glycan), a lipid (e.g., a phospholipid), or a nucleic acid (e.g., DNA, or RNA);
(f) the first exogenous polypeptide binds a target, e.g., an antibody, but does not cleave, and the second exogenous polypeptide cleaves a bond e.g., a covalent bond, e.g., a covalent bond in the antibody;
(g) the target comprises an antibody (e.g., an anti-drug antibody) and the first exogenous polypeptide binds the variable region of the antibody target;
(h) the target comprises an antibody (e.g., an anti-drug antibody) and first exogenous polypeptide binds the constant region of the antibody target;
(i) the first exogenous polypeptide has an affinity for the target that is about 1-2 pM, 2-5 pM, 5-10 pM, 10-20 pM, 20-50 pM, 50-100 pM, 100-200 pM, 200-500 pM, 500-1000 pM, 1-2 nM, 2-5 nM, 5-10 nM, 10-20 nM, 20-50 nM, 50-100 nM, 100-200 nM, 200-500 nM, 500-1000 nM, 1-2 μM, 2-5 μM, 5-10 μM, 10-20 μM, 20-50 μM, or 50-100 μM;

(j) the second exogenous polypeptide has a $K_M$ for the target of about $10^{-1}$-$10^{-7}$M, $10^{-1}$-$10^{-2}$M, $10^{-2}$-$10^{-3}$M, $10^{-3}$-$10^{-4}$M, $10^{-4}$-$10^{-5}$M, $10^{-5}$-$10^{-6}$M, or $10^{-6}$-$10^{-7}$M;

(k) a ratio of the $K_d$ of the first exogenous polypeptide for the target (measured in M) divided by the $K_M$ of the second exogenous polypeptide for the target (measured in M) is about $1\times10^{-9}$-$2\times10^{-9}$, $2\times10^{-9}$-$5\times10^{-9}$, $5\times10^{-9}$-$1\times10^{-8}$, $1\times10^{-8}$-$2\times10^{-8}$, $2\times10^{-8}$-$5\times10^{-8}$, $5\times10^{-8}$-$1\times10^{-7}$, $1\times10^{-7}$-$2\times10^{-7}$, $2\times10^{-7}$-$5\times10^{-7}$, $5\times10^{-7}$-$1\times10^{-6}$, $1\times10^{-6}$-$2\times10^{-6}$, $2\times10^{-6}$-$5\times10^{-6}$, $5\times10^{-6}$-$1\times10^{-5}$, $1\times10^{-5}$-$2\times10^{-5}$, $2\times10^{-5}$-$5\times10^{-5}$, $5\times10^{-5}$-$1\times10^{4}$, $1\times10^{-4}$-$2\times10^{-4}$, $2\times10^{-4}$-$5\times10^{-4}$, $5\times10^{-4}$-$1\times10^{-3}$, $1\times10^{-3}$-$2\times10^{-3}$, $2\times10^{-3}$-$5\times10^{-3}$, $5\times10^{-3}$-$1\times10^{-2}$, $1\times10^{-2}$-$2\times10^{2}$, $2\times10^{-2}$-$5\times10^{-2}$, $5\times10^{-2}$-$1\times10^{-1}$, $1\times10^{-1}$-$2\times10^{-1}$, $2\times10^{-1}$-$5\times10^{-1}$, or $5\times10^{-1}$-1;

(l) the observed reaction rate of the second exogenous polypeptide modifying the target is greater than the reaction rate of an enucleated cell which is similar but which lacks the first exogenous polypeptide under otherwise similar reaction conditions;

(m) a ratio of the average number of the first exogenous polypeptide on the erythroid cell to the average number of the second exogenous polypeptide on the erythroid cell is about 50:1, 20:1, 10:1, 8:1, 6:1, 4:1, 2:1, 1:1, 1:2, 1:4, 1:6, 1:8, 1:10, 1:20, or 1:50;

(n) affinity of the first exogenous polypeptide for the target is greater than the affinity of the first exogenous polypeptide for the modified (e.g., cleaved) target;

(o) a therapeutically effective dose of the enucleated erythroid cell is less than stoichiometry (e.g., less by 10%, 20%, 30%, 40%, 50%, 60%, 70%, 80%, 90%, 95%, 98%, 99%, 99.5%, 99.9%, or 99.99%) to the amount of target in a subject's peripheral blood at the time of administration;

(p) the number of enucleated erythroid cells in an effective dose, is less than (e.g., less by 10%, 20%, 30%, 40%, 50%, 60%, 70%, 80%, 90%, 95%, 98%, 99%, 99.5%, 99.9%, or 99.99%) the number of targets, e.g., target molecules, in the subject's peripheral blood at the time of administration;

(q) the number of second exogenous polypeptides comprised by a preselected amount of enucleated erythroid cells, e.g., an effective dose, or in vitro effective amount of enucleated erythroid cells, is less than (e.g., less by 10%, 20%, 30%, 40%, 50%, 60%, 70%, 80%, 90%, 95%, 98%, 99%, 99.5%, 99.9%, or 99.99%) a reference value for targets, e.g., less than the number of targets in the peripheral blood of the subject at the time of administration;

(r) the number of first exogenous polypeptides comprised by a preselected amount of enucleated erythroid cells, e.g., an effective dose, or in vitro effective amount of enucleated erythroid cells, is less than (e.g., less by 10%, 20%, 30%, 40%, 50%, 60%, 70%, 80%, 90%, 95%, 98%, 99%, 99.5%, 99.9%, or 99.99%) a reference value for targets, e.g., less than the number of targets in the peripheral blood of the subject at the time of administration;

(s) the number of first exogenous polypeptides and the number of second exogenous polypeptides comprised by a preselected amount of enucleated erythroid cells, e.g., an effective dose, enucleated erythroid cells, is each less than a reference value for targets, e.g., less than the number of targets in the peripheral blood of the subject at the time of administration;

(t) the second exogenous polypeptide modifies (e.g. cleaves) the target with a $K_M$ of at least $10^{-1}$ M, $10^{-2}$ M, $10^{-3}$ M, $10^{-4}$ M, $10^{-5}$ M, $10^{-6}$ M, or $10^{-7}$ M;

(u) the second exogenous polypeptide comprises a chaperone;

(v) the first exogenous polypeptide comprises a surface-exposed portion and the second exogenous polypeptide comprises a surface exposed portion; or (w) an effective amount of the enucleated erythroid cells is less than (e.g., less by 10%, 20%, 30%, 40%, 50%, 60%, 70%, 80%, 90%, 95%, 98%, 99%, 99.5%, 99.9%, or 99.99%) an effective amount of otherwise similar enucleated erythroid cells that lack the second exogenous polypeptide.

In embodiments, (b) the second exogenous polypeptide comprises an enzyme (e.g., a protease) that modifies, e.g., is specific, e.g., binds to a site on target, binds (e.g., specifically) and modifies, e.g., covalently modifies, e.g., cleaves, or removes or attaches a moiety to, the target, wherein the target is optionally an antibody, e.g., an anti-drug antibody. In embodiments the modification alters, e.g., increases or decreases, the ability of the target to interact with another molecule, e.g., the first exogenous polypeptide or a molecule other than the first exogenous polypeptide.

In embodiments, (d) the second exogenous polypeptide comprises a polypeptide, e.g., an enzyme (e.g., a protease) that cleaves the target, e.g., a polypeptide, between a first target domain and a second target domain, e.g., a first target domain that binds a first substrate and a second target domain that binds a second substrate. In embodiments the first target domain is released from the second target domain. In embodiments cleavage alters the affinity one or both of the first target domain for a first substrate and the affinity of the second target domain for a second substrate. In an embodiment the target comprises an antibody and the first target domain comprises one or more CDRs and the second target domain comprises a portion of the constant region, e.g., a Fc region.

In embodiments, at least two (e.g., at least 3, 4, 5, 6, 7, 8, 9, or 10) of (a)-(w) are present. In embodiments, at least (a) and (e) are present. In embodiments, at least (a) and (i) are present. In embodiments, at least (a) and (j) are present. In embodiments, at least (a) and (m) are present. In embodiments, at least (a) and (q) are present. In embodiments, at least (a) and (r) are present. In embodiments, at least (a) and (s) are present. In embodiments, at least (e) and (i) are present. In embodiments, at least (e) and (j) are present. In embodiments, at least (e) and (m) are present. In embodiments, at least (e) and (q) are present. In embodiments, at least (e) and (r) are present. In embodiments, at least (e) and (s) are present. In embodiments, at least (i) and (j) are present. In embodiments, at least (i) and (m) are present. In embodiments, at least (i) and (q) are present. In embodiments, at least (i) and (r) are present. In embodiments, at least (i) and (s) are present. In embodiments, at least (j) and (m) are present. In embodiments, at least (j) and (q) are present. In embodiments, at least (j) and (r) are present. In embodiments, at least (j) and (s) are present. In embodiments, at least (m) and (q) are present. In embodiments, at least (m) and (r) are present. In embodiments, at least (m) and (s) are present. In embodiments, at least (q) and (r) are present. In embodiments, at least (q) and (s) are present. In embodiments, at least (r) and (s) are present.

In embodiments, at least:

(a) and (b), (a) and (c), (a) and (d), (a) and (e), (a) and (f), (a) and (g), (a) and (h), (a) and (i), (a) and (j), (a) and (k), (a) and (l), (a) and (m), (a) and (n), (a) and (o), (a) and (p), (a) and (q), (a) and (r), (a) and (s), (a) and (t), (a) and (u), (a) and (v), (a) and (w), (b) and (c), (b) and (d), (b) and (e), (b) and (f), (b) and (g), (b) and (h), (b) and (i), (b) and (j), (b) and (k), (b) and (l), (b) and (m), (b) and (n), (b) and (o), (b) and (p), (b) and (q), (b) and (r), (b) and (s), (b) and (t), (b) and (u), (b) and (v), (b) and (w), (c) and (d), (c) and (e), (c) and (f), (c) and (g), (c) and (h), (c) and (i), (c) and (j), (c) and (k), (c) and (l), (c) and (m), (c) and (n), (c) and (o), (c) and (p), (c) and (q), (c) and (r), (c) and (s), (c) and (t), (c) and (u), (c) and (v), (c) and (w), (d) and (e), (d) and (f), (d) and (g), (d) and (h), (d) and (i), (d) and (j), (d) and (k), (d) and (l), (d) and (m), (d) and (n), (d) and (o), (d) and (p), (d) and (q), (d) and (r), (d) and (s), (d) and (t), (d) and (u), (d) and (v), (d) and (w), (e) and (f), (e) and (g), (e) and (h), (e) and (i), (e) and (j), (e) and (k), (e) and (l), (e) and (m), (e) and (n), (e) and (o), (e) and (p), (e) and (q), (e) and (r), (e) and (s), (e) and (t), (e) and (u), (e) and (v), (e) and (w), (f) and (g), (f) and (h), (f) and (i), (f) and (j), (f) and (k), (f) and (l), (f) and (m), (f) and (n), (f) and (o), (f) and (p), (f) and (q), (f) and (r), (f) and (s), (f) and (t), (f) and (u), (f) and (v), (f) and (w), (g) and (h), (g) and (i), (g) and (j), (g) and (k), (g) and (l), (g) and (m), (g) and (n), (g) and (o), (g) and (p), (g) and (q), (g) and (r), (g) and (s), (g) and (t), (g) and (u), (g) and (v), (g) and (w), (h) and (i), (h) and (j), (h) and (k), (h) and (l), (h) and (m), (h) and (n), (h) and (o), (h) and (p), (h) and (q), (h) and (r), (h) and (s), (h) and (t), (h) and (u), (h) and (v), (h) and (w), (i) and (j), (i) and (k), (i) and (l), (i) and (m), (i) and (n), (i) and (o), (i) and (p), (i) and (q), (i) and (r), (i) and (s), (i) and (t), (i) and (u), (i) and (v), (i) and (w), (j) and (k), (j) and (l), (j) and (m), (j) and (n), (j) and (o), (j) and (p), (j) and (q), (j) and (r), (j) and (s), (j) and (t), (j) and (u), (j) and (v), (j) and (w), (k) and (l), (k) and (m), (k) and (n), (k) and (o), (k) and (p), (k) and (q), (k) and (r), (k) and (s), (k) and (t), (k) and (u), (k) and (v), (k) and (w), (l) and (m), (l) and (n), (l) and (o), (l) and (p), (l) and (q), (l) and (r), (l) and (s), (l) and (t), (l) and (u), (l) and (v), (l) and (w), (m) and (n), (m) and (o), (m) and (p), (m) and (q), (m) and (r), (m) and (s), (m) and (t), (m) and (u), (m) and (v), (m) and (w), (n) and (o), (n) and (p), (n) and (q), (n) and (r), (n) and (s), (n) and (t), (n) and (u), (n) and (v), (n) and (w), (o) and (p), (o) and (q), (o) and (r), (o) and (s), (o) and (t), (o) and (u), (o) and (v), (o) and (w), (p) and (q), (p) and (r), (p) and (s), (p) and (t), (p) and (u), (p) and (v), (p) and (w), (q) and (r), (q) and (s), (q) and (t), (q) and (u), (q) and (v), (q) and (w), (r) and (s), (r) and (t), (r) and (u), (r) and (v), (r) and (w), (s) and (t), (s) and (u), (s) and (v), (s) and (w), (t and (u), (t) and (v), (t) and (w), (u) and (v), (u) and (w), or (v) and (w), are present.

In embodiments, the target is other than an infectious component, e.g., other than a bacterial component, a viral component, a fungal component, or a parasitic component. In embodiments, the first exogenous polypeptide comprises a target-binding domain. In embodiments, the surface-exposed portion of the first exogenous polypeptide binds the target. In embodiments, the surface-exposed portion of the second exogenous polypeptide comprises enzymatic activity, e.g., protease activity. In embodiments, the surface-exposed portion of the second exogenous polypeptide enzymatically modifies, e.g., cleaves, the target. In embodiments, the target comprises an anti-drug antibody, the first exogenous polypeptide comprises a polypeptide to which the anti-drug antibody binds, and the second exogenous polypeptide comprises a protease that cleaves the anti-drug antibody to produce a Fab portion and an Fc portion. In embodiments, the enucleated red blood cell is capable of clearing the target from a subject's body at a faster rate than an otherwise similar enucleated red blood cell that lacks the second exogenous polypeptide. In embodiments, the enucleated red blood cell is complexed with the target or a reaction product of the second exogenous protein acting on the target, e.g., during cleavage.

The present disclosure also provides, in certain aspects, an enucleated erythroid cell comprising:

a first exogenous polypeptide comprising a transmembrane domain and a surface-exposed polypeptide capable of binding an anti-drug antibody, and a second exogenous polypeptide comprising a transmembrane domain and a surface-exposed IdeS polypeptide.

The present disclosure also provides, in some aspects, a polypeptide comprising a protease that can cleave an antibody, e.g., an IdeS polypeptide, and a membrane anchor domain, e.g., a transmembrane domain, e.g., type I or type II red blood cell transmembrane domain. The disclosure also provides a nucleic acid encoding said polypeptide.

The present disclosure also provides, in some aspects, a nucleic acid comprising:

a first sequence encoding a protease that can cleave an antibody, e.g., an IdeS polypeptide, a second sequence encoding a membrane anchor domain, e.g., a transmembrane domain, wherein the first and second sequences are operatively linked to form a fusion protein; and optionally, a promoter sequence that is active in an erythroid cell.

The present disclosure also provides, in some aspects, a nucleic acid composition comprising:

a first nucleic acid sequence encoding a first exogenous polypeptide that interacts with a target, e.g., a first exogenous polypeptide described herein, a second nucleic acid sequence encoding a second exogenous polypeptide that modifies the target, e.g., a second nucleic acid sequence described herein and optionally, a promoter sequence that is active in an erythroid cell.

In embodiments, the first nucleic acid sequence and second nucleic acid sequence are contiguous or are separate molecules (e.g., admixed molecules or in separate containers). In embodiments, the first nucleic acid sequence and second nucleic acid sequence are part of the same open reading frame and have a protease cleavage site situated therebetween. In embodiments, the first nucleic acid is operatively linked to a first promoter and the second nucleic acid is operatively linked to a second promoter.

The disclosure provides, in some aspects, a kit comprising:

(A) nucleic acids encoding: (A-i) a plurality of binding moieties (e.g., antibody molecules, e.g., scFv domains), fused to (A-ii) a membrane anchor domain, e.g., a transmembrane domain, wherein (A-i) and (A-ii) are operatively linked to a nucleic acid that directs expression in an erythroid cell; and (B) nucleic acids encoding (B-i) a plurality of enzymes (e.g., proteases), optionally fused to (B-ii) a membrane anchor domain, e.g., a transmembrane domain, wherein (B-i) and (B-ii) are operatively linked to nucleic acid that directs expression in an erythroid cell.

The present disclosure provides, in some aspects, a method of making a fragment of a target, e.g., a target polypeptide, e.g., a method of making a fragment of a target comprising a first target domain, e.g., a method of making a variable region fragment, or a method of making a constant region containing fragment, comprising contacting the target polypeptide with an erythroid cell described herein. In embodiments, the second exogenous polypeptide cleaves the target to provide the fragment. In embodiments, the target polypeptide is an antibody, e.g., an anti-drug antibody. In embodiments, the fragment of the target polypeptide does not activate an immune response and/or inflammation. In embodiments, the contacting comprises administering the erythroid cell to a subject that comprises the target polypeptide.

The present disclosure also provides, in certain aspects, a method of making an inhibitor, e.g., a competitive inhibitor, comprising, e.g., contacting a precursor of the inhibitor (a target) with an erythroid cell described herein. In embodiments, the second exogenous polypeptide interacts with the target, e.g., cleaves the target. In embodiments, the inhibitor is an antibody fragment (e.g., a Fab fragment). In embodiments, the target is an antibody which is cleaved to produce an inhibitor which is an antibody fragment, e.g., Fab fragment. In embodiments, the inhibitor does not activate an immune response and/or inflammation. In embodiments, the precursor of the inhibitor is an antibody, e.g., an anti-drug antibody. In embodiments, the contacting comprises administering the erythroid cell to a subject that comprises the precursor of the inhibitor.

The present disclosure also provides, in some aspects, a method of converting or activating a target, e.g., a polypeptide, e.g., converting a prodrug to a drug, comprising contacting the polypeptide with an erythroid cell described herein. In embodiments, the second exogenous polypeptide interacts with the target (e.g., prodrug), e.g., cleaves the target. In embodiments, the prodrug is an antibody, e.g., an anti-drug antibody. In embodiments, the drug is an antibody fragment, e.g., a Fab fragment. In embodiments, the drug does not activate an immune response and/or inflammation. In embodiments, the contacting comprises administering the erythroid cell to a subject that comprises the polypeptide, e.g., prodrug.

The present disclosure also provides, in some aspects, a method of converting an endogenous polypeptide from a first activity state to a second activity state (e.g., from an inactive state to an active state or an active state to an inactive state), comprising contacting the endogenous polypeptide with an erythroid cell described herein. In embodiments, the second exogenous polypeptide interacts with the target, e.g., covalently modifies, e.g., cleaves the target, or alters its ability to interact with, e.g., bind, another molecule. In embodiments, the endogenous polypeptide is an antibody, e.g., an anti-drug antibody. In embodiments, the contacting comprises administering the erythroid cell to a subject that comprises the endogenous polypeptide.

The disclosure provides, in some aspects, a method of reducing a level of a target (e.g., an antibody, e.g., an anti-drug antibody) in a subject, comprising administering to the subject an erythroid cell described herein. In embodiments, the second exogenous polypeptide interacts with the target, e.g., covalently modifies, e.g., cleaves the target, or alters its ability to interact with, e.g., bind, another molecule. The disclosure also provides, in certain aspects, a method of generating an inhibitory fragment of an antibody (e.g., a Fab fragment) in a subject, comprising administering to the subject an erythrocyte cell described herein. The disclosure provides, in addition, a method of treating a disease in a subject, e.g., cancer, comprising administering to the subject an erythroid cell described herein.

In embodiments, e.g., embodiments of any of the methods described above, the erythroid cell comprises:
a first exogenous polypeptide that interacts with a target, and
a second exogenous polypeptide that modifies the target; wherein one or more of:

(a) the second exogenous polypeptide comprises a moiety that cleaves an antibody, e.g., that cleaves at a hinge region, a CH2 region, or between a hinge and CH2 region, e.g., an IdeS polypeptide;

(b) the second exogenous polypeptide comprises an enzyme (e.g., a protease) that modifies, e.g., is specific, e.g., binds to a site on target, binds (e.g., specifically) and modifies, e.g., covalently modifies, e.g., cleaves, or removes or attaches a moiety to, the target, wherein the target is optionally an antibody;

(c) the second exogenous polypeptide comprises a polypeptide, e.g., an enzyme, e.g., a protease, that modifies the secondary, tertiary, or quaternary structure of the target, and, in embodiments, alters, e.g., decreases or increases, the ability of the target to interact with another molecule, e.g., the first exogenous polypeptide or a molecule other than the first exogenous polypeptide, wherein optionally the target comprises an antibody, or complement factor;

(d) the second exogenous polypeptide comprises a polypeptide, e.g., an enzyme (e.g., a protease) that cleaves the target, e.g., a polypeptide, between a first target domain and a second target domain, e.g., a first target domain that binds a first substrate and a second target domain that binds a second substrate;

(e) the target is a polypeptide, a carbohydrate (e.g., a glycan), a lipid (e.g., a phospholipid), or a nucleic acid (e.g., DNA or RNA);

(f) the first exogenous polypeptide binds a target, e.g., an antibody, but does not cleave, and the second exogenous polypeptide cleaves a bond e.g., a covalent bond, e.g., a covalent bond in the antibody;

(g) the target comprises an antibody and the first exogenous polypeptide binds the variable region of the antibody target;

(h) the target comprises an antibody and first exogenous polypeptide binds the constant region of the antibody target;

(i) the first exogenous polypeptide has an affinity for the target that is about 1-2 pM, 2-5 pM, 5-10 pM, 10-20 pM, 20-50 pM, 50-100 pM, 100-200 pM, 200-500 pM, 500-1000 pM, 1-2 nM, 2-5 nM, 5-10 nM, 10-20 nM, 20-50 nM, 50-100 nM, 100-200 nM, 200-500 nM, 500-1000 nM, 1-2 µM, 2-5 µM, 5-10 µM, 10-20 µM, 20-50 µM, or 50-100 µM;

(j) the second exogenous polypeptide has a $K_M$ for the target of about $10^{-1}$-$10^{-7}$M, $10^{-1}$-$10^{-2}$M, $10^{-2}$-$10^{-3}$M, $10^{-3}$-$10^{-4}$M, $10^{-4}$-$10^{-5}$M, $10^{-5}$-$10^{-6}$M, or $10^{-6}$-$10^{-7}$M;

(k) a ratio of the $K_d$ of the first exogenous polypeptide for the target (measured in M) divided by the $K_M$ of the second exogenous polypeptide for the target (measured in M) is about $1\times10^{-9}$-$2\times10^{-9}$, $2\times10^{-9}$-$5\times10^{-9}$, $5\times10^{-9}$-$1\times10^{-8}$, $1\times10^{-8}$-$2\times10^{-8}$, $2\times10^{-8}$-$5\times10^{-8}$, $5\times10^{-8}$-$1\times10^{-7}$, $1\times10^{-7}$-$2\times10^{-7}$, $2\times10^{-7}$-$5\times10^{-7}$, $5\times10^{-7}$-$1\times10^{-6}$, $1\times10^{-6}$-$2\times10^{-6}$, $2\times10^{-6}$-$5\times10^{-6}$, $5\times10^{-6}$-$1\times10^{-5}$, $1\times10^{-5}$-$2\times10^{-5}$, $2\times10^{-5}$-$5\times10^{-5}$, $5\times10^{-5}$-$1\times10^{4}$, $1\times10^{-4}$, $2\times10^{-4}$, $2\times10^{-4}$-$5\times10^{4}$, $5\times10^{-4}$-$1\times10^{-3}$, $1\times10^{-3}$-$2\times10^{-3}$, $2\times10^{-3}$-$5\times10^{-3}$, $5\times10^{-3}$-$1\times10^{-2}$, $1\times10^{-2}$-$2\times10^{2}$, $2\times10^{-2}$-$5\times10^{-2}$, $5\times10^{-2}$-$1\times10^{-1}$, $1\times10^{-1}$-$2\times10^{-1}$, $2\times10^{-1}$-$5\times10^{-1}$, or $5\times10^{-1}$-1;

(l) the observed reaction rate of the second exogenous polypeptide modifying the target is greater than the reaction rate of an enucleated cell which is similar but which lacks the first exogenous polypeptide under otherwise similar reaction conditions;

(m) a ratio of the average number of the first exogenous polypeptide on the erythroid cell to the average number of the second exogenous polypeptide on the erythroid cell is about 50:1, 20:1, 10:1, 8:1, 6:1, 4:1, 2:1, 1:1, 1:2, 1:4, 1:6, 1:8, 1:10, 1:20, or 1:50;

(n) affinity of the first exogenous polypeptide for the target is greater than the affinity of the first exogenous polypeptide for the modified (e.g., cleaved) target;

(o) a therapeutically effective dose of the enucleated erythroid cell is less than (e.g., less by 10%, 20%, 30%, 40%, 50%, 60%, 70%, 80%, 90%, 95%, 98%, 99%, 99.5%, 99.9%, or 99.99%) stoichiometry to the amount of target in a subject's peripheral blood at the time of administration;

(p) the number of enucleated erythroid cells in an effective dose, is less than (e.g., less by 10%, 20%, 30%, 40%, 50%, 60%, 70%, 80%, 90%, 95%, 98%, 99%, 99.5%, 99.9%, or 99.99%) the number of targets, e.g., target molecules, in the subject's peripheral blood at the time of administration;

(q) the number of second exogenous polypeptides comprised by a preselected amount of enucleated erythroid cells, e.g., an effective dose of enucleated erythroid cells, is less than (e.g., less by 10%, 20%, 30%, 40%, 50%, 60%, 70%, 80%, 90%, 95%, 98%, 99%, 99.5%, 99.9%, or 99.99%) a reference value for targets, e.g., less than the number of targets in the peripheral blood of the subject at the time of administration;

(r) the number of first exogenous polypeptides comprised by a preselected amount of enucleated erythroid cells, e.g., an effective dose of enucleated erythroid cells, is less than (e.g., less by 10%, 20%, 30%, 40%, 50%, 60%, 70%, 80%, 90%, 95%, 98%, 99%, 99.5%, 99.9%, or 99.99%) a reference value for targets, e.g., less than the number of targets in the peripheral blood of the subject at the time of administration;

(s) the number of first exogenous polypeptides and the number of second exogenous polypeptides comprised by a preselected amount of enucleated erythroid cells, e.g., an effective dose, enucleated erythroid cells, is each less than (e.g., less by 10%, 20%, 30%, 40%, 50%, 60%, 70%, 80%, 90%, 95%, 98%, 99%, 99.5%, 99.9%, or 99.99%) a reference value for targets, e.g., less than the number of targets in the peripheral blood of the subject at the time of administration;

(t) the second exogenous polypeptide modifies (e.g. cleaves) the target with a $K_M$ of at least $10^{-1}$ M, $10^{-2}$ M, $10^{-3}$ M, $10^{-4}$ M, $10^{-5}$ M, $10^{-6}$ M, or $10^{-7}$ M;

(u) the second exogenous polypeptide comprises a chaperone;

(v) the first exogenous polypeptide comprises a surface-exposed portion and the second exogenous polypeptide comprises a surface exposed portion; or (w) an effective amount of the enucleated erythroid cells is less than (e.g., less by 10%, 20%, 30%, 40%, 50%, 60%, 70%, 80%, 90%, 95%, 98%, 99%, 99.5%, 99.9%, or 99.99%) an effective amount of otherwise similar enucleated erythroid cells that lack the second exogenous polypeptide.

In some embodiments of any of the compositions and methods described herein involving an exogenous polypeptide, e.g., a fusion protein:

i) at least 50, 60, 70, 80, 90, 95, or 99% of the fusion proteins on the surface of the erythroid cell have an identical sequence, ii) at least 50, 60, 70, 80, 90, 95, or 99% of the fusion protein have the same transmembrane region, iii) the fusion protein does not include a full length endogenous membrane protein, e.g., comprises a segment of a full length endogenous membrane protein, which segment lacks at least 1, 2, 3, 4, 5, 10, 20, 50, 100, 200, or 500 amino acids of the full length endogenous membrane protein;

iv) at least 50, 60, 70, 80, 90, 95, or 99% of the fusion proteins do not differ from one another by more than 1, 2, 3, 4, 5, 10, 20, or 50 amino acids, v) the exogenous polypeptide lacks a sortase transfer signature, vi) the exogenous polypeptide comprises a moiety that is present on less than 1, 2, 3, 4, or 5 sequence distinct fusion polypeptides;

vii) the exogenous polypeptide is present as a single fusion polypeptide;

viii) the fusion protein does not contain Gly-Gly at the junction of an endogenous transmembrane protein and the moiety;

ix) the fusion protein does not contain Gly-Gly, or the fusion protein does not contain Gly-Gly, or does not contain Gly-Gly in an extracellular region, does not contain Gly-Gly in an extracellular region that is within 1, 2, 3, 4, 5, 10, 20, 50, or 100 amino acids of a transmembrane segment; or a combination thereof.

The cell systems described herein may be used in combination with another (one or more) anti-proliferative, anti-neoplastic or anti-tumor drug or treatment that is not part of the cell system. Such drugs or treatments include chemotherapeutic drugs, e.g., cytotoxic drugs (e.g., alkylating agents, antimetabolites, anti-tumor antibiotics, topoisomerase inhibitors, mitotic inhibitors, corticosteroids); cancer growth blockers such as tyrosine kinase inhibitors and proteasome inhibitors; T cell therapy (e.g., CAR-T cell therapy) (see, e.g., PMID: 26611350), Natural Killer (NK) cell immunomodulation (see, e.g., PMID: 26697006); and cancer vaccines (PMID: 26579225); other chemical drugs such as L-asparaginase and bortezomib (Velcade®). Hormone therapies (or anti-hormone therapies) may be used, e.g., for hormone-sensitive cancers.

The cell systems described herein may also be used in combination with non-drug therapies for cancer such as surgery, radiotherapy, or cryotherapy. In some cases, treatment methods of the invention may include a cell system described herein in combination with 2 or more other therapies or drugs, e.g., breast cancer may be treated with a combination of a cell system described herein in combination with surgery or radiotherapy and a chemotherapeutic cocktail or biologic (e.g., an anti-HER2 antibody).

The disclosure contemplates all combinations of any one or more of the foregoing aspects and/or embodiments, as well as combinations with any one or more of the embodiments set forth in the detailed description and examples.

Although methods and materials similar or equivalent to those described herein can be used in the practice or testing of the present invention, suitable methods and materials are described below. All publications, patent applications, patents, and other references (e.g., sequence database reference numbers) mentioned herein are incorporated by reference in their entirety. For example, all GenBank, Unigene, and Entrez sequences referred to herein, e.g., in any Table herein, are incorporated by reference. Unless otherwise specified, the sequence accession numbers specified herein, including in any Table herein, refer to the database entries current as of Jan. 11, 2016. When one gene or protein references a plurality of sequence accession numbers, all of the sequence variants are encompassed.

DETAILED DESCRIPTION OF THE INVENTION

Definitions

Figure 1:
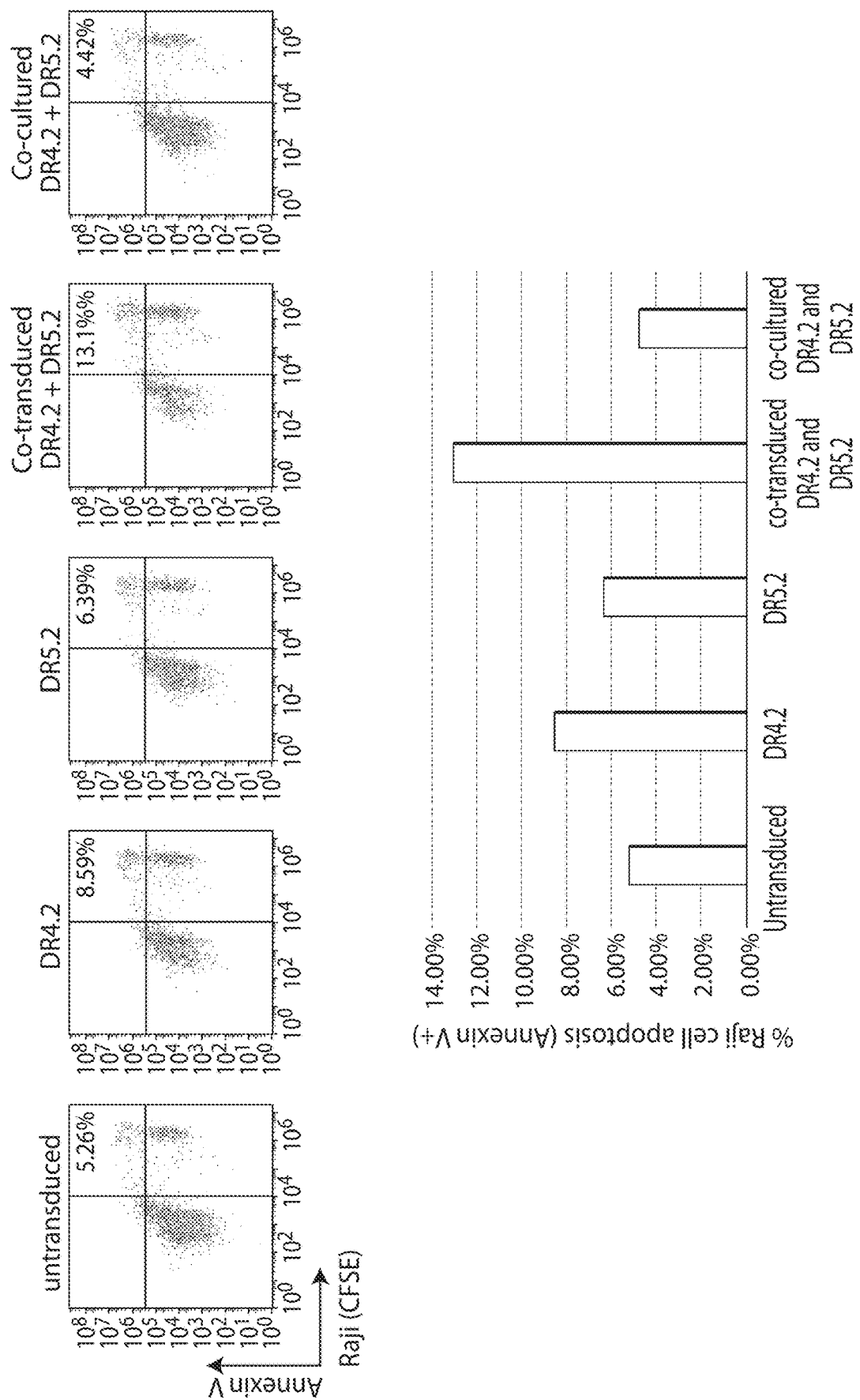
FIG. 1 is a set of graphs showing results of a Raji apoptosis assay measured through flow cytometry. Raji cells are CFSE labeled and co-cultured with erythroid differentiated cells that are untransduced (control) and transduced with single or multiple TRAIL variants or co-cultured with two different singly transduced cells. Percent apoptosis determined by percent of cells that are Raji (CFSE+) and annexin V+. (Top) Flow cytometry plots of CFSE and annexin V staining of various conditions. (Bottom) Graph of percent apoptosis of the various conditions.

As used herein, the term "antibody molecule" refers to a protein, e.g., an immunoglobulin chain or fragment thereof, comprising at least one immunoglobulin variable domain sequence. The term "antibody molecule" encompasses antibodies and antibody fragments. In an embodiment, an antibody molecule is a multispecific antibody molecule, e.g., a bispecific antibody molecule. Examples of antibody molecules include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multispecific antibodies formed from antibody fragments such as a bivalent fragment comprising two Fab fragments linked by a disulfide bridge at the hinge region, an isolated epitope binding fragment of an antibody, maxibodies, minibodies, nanobodies, intrabodies, diabodies, triabodies, tetrabodies, v-NAR and bis-scFv.

As used herein, a "combination therapy" or "administered in combination" means that two (or more) different agents or treatments are administered to a subject as part of a treatment regimen for a particular disease or condition. The treatment regimen includes the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

The term "coordinated" or "coordinated manner" means that a plurality of agents work together to provide a therapeutic benefit. Types of coordinated activity include agent-additive, agent-synergistic, multiplicative, independent function, localization-based, proximity-dependent, scaffold-based, multimer-based, and compensatory activity. In an embodiment the level of therapeutic benefit conferred by a plurality of exogenous polypeptides delivered in the same enucleated RBC is greater than would be seen if each of the plurality of polypeptides were delivered from different enucleated RBCs.

As used herein, "enucleated" refers to a cell that lacks a nucleus, e.g., a cell that lost its nucleus through differentiation into a mature red blood cell.

As used herein, the term "exogenous polypeptide" refers to a polypeptide that is not produced by a wild-type cell of that type or is present at a lower level in a wild-type cell than in a cell containing the exogenous polypeptide. In some embodiments, an exogenous polypeptide is a polypeptide encoded by a nucleic acid that was introduced into the cell, which nucleic acid is optionally not retained by the cell.

As used herein, the term "multimodal therapy" refers to a therapy, e.g., an enucleated red blood cell therapy, that provides a plurality (e.g., 2, 3, 4, or 5 or more) of exogenous agents (e.g., polypeptides) that have a coordinated function (e.g., agent-additive, agent-synergistic, multiplicative, independent function, localization-based, proximity-dependent, scaffold-based, multimer-based, or compensatory activity).

As used herein, the term "pathway" or "biological pathway" refers to a plurality of biological molecules, e.g., polypeptides, that act together in a sequential manner. Examples of pathways include signal transduction cascades. In some embodiments, a pathway begins with detection of an extracellular signal and ends with a change in transcription of a target gene. In some embodiments, a pathway begins with detection of a cytoplasmic signal and ends with a change in transcription of a target gene. A pathway can be linear or branched. If branched, it can have a plurality of inputs (converging), or a plurality of outputs (diverging).

As used herein, a "proximity-dependent" molecule refers to a first molecule that has a different, e.g., greater, activity when in proximity with a second molecule than when alone. In some embodiments, a pair of proximity-dependent ligands activates a downstream factor more strongly when the ligands are in proximity than when they are distant from each other.

As used herein, "receptor component" refers to a polypeptide that functions as a receptor, by itself or as part of a complex. Thus a receptor component encompasses a polypeptide receptor and a polypeptide that functions as part of a receptor complex.

The term "synergy" or "synergistic" means a more than additive effect of a combination of two or more agents (e.g., polypeptides that are part of an enucleated red blood cell) compared to their individual effects. In certain embodiments, synergistic activity is a more-than-additive effect of an enucleated red blood cell comprising a first polypeptide and a second polypeptide, compared to the effect of an enucleated red blood cell comprising the first polypeptide and an enucleated red blood cell comprising the second polypeptide. In some embodiments, synergistic activity is present when a first agent produces a detectable level of an output X, a second agent produces a detectable level of the output X, and the first and second agents together produce a more-than-additive level of the output X.

As used herein, the term "variant" of a polypeptide refers to a polypeptide having at least one sequence difference compared to that polypeptide, e.g., one or more substitutions, insertions, or deletions. In some embodiments, the variant has at least 70%, 80%, 85%, 90%, 95%, 96%, 97%, 98%, or 99% identity to that polypeptide. A variant includes a fragment. In some embodiments, a fragment lacks up to 1, 2, 3, 4, 5, 10, 20, or 100 amino acids on the N-terminus, C-terminus, or both (each independently), compared to the full-length polypeptide.

Exemplary Exogenous Polypeptides and Uses Thereof

In embodiments, the red blood cell therapeutics described herein comprise one or more (e.g., 2, 3, 4, 5, 6, 10 or more) different exogenous agents, e.g., exogenous polypeptides, lipids, or small molecules. In some embodiments, a red blood cell therapeutic comprises an exogenous fusion polypeptide comprising two or more different proteins described herein. In some embodiments, an enucleated red blood cell, e.g., a reticulocyte, comprises two or more different exogenous polypeptides described herein. In some embodiments, one or more (e.g., all) of the exogenous polypeptides are human polypeptides or fragments or variants thereof.

In some embodiments, the two or more polypeptides act on the same target, and in other embodiments, they act on two or more different targets. In some embodiments, the single target or plurality of targets is chosen from an endogenous human protein or a soluble factor (e.g., a polypeptide, small molecule, or cell-free nucleic acid).

One or more of the exogenous proteins may have post-translational modifications characteristic of eukaryotic cells, e.g., mammalian cells, e.g., human cells. In some embodiments, one or more (e.g., 2, 3, 4, 5, or more) of the exogenous proteins are glycosylated, phosphorylated, or both. In vitro detection of glycoproteins is routinely accomplished on SDS-PAGE gels and Western Blots using a modification of Periodic acid-Schiff (PAS) methods. Cellular localization of glycoproteins may be accomplished utilizing lectin fluorescent conjugates known in the art. Phosphorylation may be assessed by Western blot using phospho-specific antibodies.

Post-translation modifications also include conjugation to a hydrophobic group (e.g., myristoylation, palmitoylation, isoprenylation, prenylation, or glypiation), conjugation to a cofactor (e.g., lipoylation, flavin moiety (e.g., FMN or FAD), heme C attachment, phosphopantetheinylation, or retinylidene Schiff base formation), diphthamide formation, ethanolamine phosphoglycerol attachment, hypusine formation, acylation (e.g. O-acylation, N-acylation, or S-acylation), formylation, acetylation, alkylation (e.g., methylation or ethylation), amidation, butyrylation, gamma-carboxylation, malonylation, hydroxylation, iodination, nucleotide addition such as ADP-ribosylation, oxidation, phosphate ester (O-linked) or phosphoramidate (N-linked) formation, (e.g., phosphorylation or adenylylation), propionylation, pyroglutamate formation, S-glutathionylation, S-nitrosylation, succinylation, sulfation, ISGylation, SUMOylation, ubiquitination, Neddylation, or a chemical modification of an amino acid (e.g., citrullination, deamidation, eliminylation, or carbamylation), formation of a disulfide bridge, racemization (e.g., of proline, serine, alanine, or methionine). In embodiments, glycosylation includes the addition of a glycosyl group to arginine, asparagine, cysteine, hydroxylysine, serine, threonine, tyrosine, or tryptophan, resulting in a glycoprotein. In embodiments, the glycosylation comprises, e.g., O-linked glycosylation or N-linked glycosylation.

In some embodiments, one or more of the exogenous polypeptides is a fusion protein, e.g., is a fusion with an endogenous red blood cell protein or fragment thereof, e.g., a transmembrane protein, e.g., GPA or a transmembrane fragment thereof. In some embodiments, one or more of the exogenous polypeptides is fused with a domain that promotes dimerization or multimerization, e.g., with a second fusion exogenous polypeptide, which optionally comprises a dimerization domain. In some embodiments, the dimerization domain comprises a portion of an antibody molecule, e.g., an Fc domain or CH3 domain. In some embodiments, the first and second dimerization domains comprise knob-in-hole mutations (e.g., a T366Y knob and a Y407T hole) to promote heterodimerization.

An exemplary human polypeptide, e.g., a human polypeptide selected from any of Tables 1-4, includes:

a) a naturally occurring form of the human polypeptide, e.g., a naturally occurring form of the human polypeptide that is not associated with a disease state;

b) the human polypeptide having a sequence appearing in a database, e.g., GenBank database, on Jan. 11, 2017, for example a naturally occurring form of the human polypeptide that is not associated with a disease state having a sequence appearing in a database, e.g., GenBank database, on Jan. 11, 2017;

c) a human polypeptide having a sequence that differs by no more than 1, 2, 3, 4, 5 or 10 amino acid residues from a sequence of a) or b);

d) a human polypeptide having a sequence that differs at no more than 1, 2, 3, 4, 5 or 10% its amino acids residues from a sequence of a) or b);

e) a human polypeptide having a sequence that does not differ substantially from a sequence of a) or b); or f) a human polypeptide having a sequence of c), d), or e) that does not differ substantially in a biological activity, e.g., an enzymatic activity (e.g., specificity or turnover) or binding activity (e.g., binding specificity or affinity) from a human polypeptide having the sequence of a) or b). Candidate peptides under f) can be made and screened for similar activity as described herein and would be equivalent hereunder if expressed in enucleated RBCs as described herein).

In embodiments, an exogenous polypeptide comprises a human polypeptide or fragment thereof, e.g., all or a fragment of a human polypeptide of a), b), c), d), e), or f) of the preceding paragraph. In an embodiment, the exogenous polypeptide comprises a fusion polypeptide comprising all or a fragment of a human polypeptide of a), b), c), d), e), or f) of the preceding paragraph and additional amino acid sequence. In an embodiment the additional amino acid sequence comprises all or a fragment of human polypeptide of a), b), c), d), e), or f) of the preceding paragraph for a different human polypeptide.

The invention contemplates that functional fragments or variants thereof (e.g., a ligand-binding fragment or variant thereof of the receptors listed in Tables 1-4) can be made and screened for similar activity as described herein and would be equivalent hereunder if expressed in enucleated RBCs as described herein).

In embodiments, the two or more exogenous agents (e.g., polypeptides) have related functions that are agent-additive, agent-synergistic, multiplicative, independent function, localization-based, proximity-dependent, scaffold-based, multimer-based, or compensatory, as described herein. In some embodiments, more than one of these descriptors applies to a given RBC.

Agent-Additive Configurations

When two or more agents (e.g., polypeptides) are agent-additive, the effect of the agents acting together is greater than the effect of either agent acting alone. In an embodiment, two agents have different (e.g., complementary) functions in the RBC (e.g., on the RBC surface) and act together to have a stronger effect (compared to either of the agents acting alone), e.g., a higher binding affinity for the target, or a greater degree of modulation of signal transduction by the target, e.g., a single target. In some embodiments, two or more agents each bind to the same target, e.g., to different epitopes within the same target protein.

In an embodiment the agents associate with one another, e.g., are members of a heterodimeric complex. In an embodiment, the agents have greater avidity for a target when acting together than when acting alone.

In some embodiments, the two or more agents enable tighter binding to a target than either agent alone. In some embodiments, a heterodimer of receptor components, e.g., cytokine receptor components, e.g., interleukin receptor components, e.g., IL-1 receptor components, bind to a target, e.g., IL-1, with higher affinity than either receptor component alone. Many signaling molecules form heterodimers or heteromultimers on the cell surface to bind to their ligand. Cytokine receptors, for example, can be heterodimers or heteromultimers. For instance, IL-2 receptor comprises three different molecules: IL2Ra, IL2Rb, and IL2Rg. The IL-13 receptor is a heterodimer of IL13Ra and IL4R. The IL-23 receptor is a heterodimer of IL23R and IL12Rb1. The TNFa receptor is, in embodiments, a heterodimer of TNFR1 and TNFR2. In some embodiments, one or more of the exogenous polypeptides comprises a cytokine of Table 1, or a cytokine receptor-binding fragment or variant thereof. The expressed cytokines typically have the wild type human receptor sequence or a variant or fragment thereof that is able to bind and signal through its target receptor. A table of cytokines and their receptors is provided herein as Table 1. The cytokines can be present on the surface of the RBC.

TABLE 1

| Cytokines and Receptors | |
|---|---|
| Name | Cytokine Receptor(s)(Da) and Form |
| Interleukins | |
| IL-1-like | |
| IL-1α | CD121a, CDw121b |
| IL-1β | CD121a, CDw121b |
| IL-1RA | CD121a |
| IL-18 | IL-18Rα, β |
| Common g chain (CD132) | |
| IL-2 | CD25, 122, 132 |
| IL-4 | CD124, 213a13, 132 |
| IL-7 | CD127, 132 |
| IL-9 | IL-9R, CD132 |
| IL-13 | CD213a1, 213a2, |
| IL-15 | IL-15Ra, CD122, 132 |
| Common b chain (CD131) | |
| IL-3 | CD123, CDw131 |
| IL-5 | CDw125, 131 |
| Also related | |
| GM-CSF | CD116, CDw131 |
| IL-6-like | |
| IL-6 | CD126, 130 |
| IL-11 | IL-11Ra, CD130 |
| Also related | |
| G-CSF | CD114 |
| IL-12 | CD212 |
| LIF | LIFR, CD130 |
| OSM | OSMR, CD130 |
| IL-10-like | |
| IL-10 | CDw210 |
| IL-20 | IL-20Rα, β |
| Others | |
| IL-14 | IL-14R |
| IL-16 | CD4 |
| IL-17 | CDw217 |

TABLE 1-continued

Cytokines and Receptors

| Name | Cytokine Receptor(s)(Da) and Form |
|---|---|
| Interferons | |
| IFN-α | CD118 |
| IFN-β | CD118 |
| IFN-γ | CDw119 |
| TNF | |
| CD154 | CD40 |
| LT-β | LTβR |
| TNF-α | CD120a, b |
| TNF-β (LT-α) | CD120a, b |
| 4-1BBL | CD137 (4-1BB) |
| APRIL | BCMA, TACI |
| CD70 | CD27 |
| CD153 | CD30 |
| CD178 | CD95 (Fas) |
| GITRL | GITR |
| LIGHT | LTbR, HVEM |
| OX40L | OX40 |
| TALL-1 | BCMA, TACI |
| TRAIL | TRAILR1-4 |
| TWEAK | Apo3 |
| TRANCE | RANK, OPG |
| TGF-β | |
| TGF-β1 | TGF-βR1 |
| TGF-β2 | TGF-βR2 |
| TGF-β3 | TGF-βR3 |
| Miscellaneous hematopoietins | |
| Epo | EpoR |
| Tpo | TpoR |
| Flt-3L | Flt-3 |
| SCF | CD117 |
| M-CSF | CD115 |
| MSP | CDw136 |

In some embodiments the agents are different antibody-binding molecules, e.g., Fc-binding molecules, for the capture of antibodies in circulation, e.g., anti-drug antibodies. In embodiments, the agents are non-competitive with one another to enable higher affinity binding of individual antibodies or opsonized particles. For example, in embodiments, one or more agent is chosen from protein A, Fc receptor 1 (FcR1), FcR2a, FcR2b, FcR3, FcR4, FcRn (neonatal Fc receptor) or an antibody-binding fragment or variant thereof.

In some embodiments the target is a circulating cancer cell, e.g. a cancerous B cell, T cell, lymphoid cell, or a circulating tumor cell (CTC). In embodiments, the engineered red blood cell (e.g., a reticulocyte) is used to capture the cancer cell and remove it from circulation. For instance, the one or more agents bind to different proteins on the cell surface to enhance the specificity of the therapy. For example the agents comprise anti-EPCAM and anti CD45 antibody molecules to capture CTCs, or anti-CD19 and anti-CD20 antibody molecules to capture B cell lineage acute leukemic cells.

An enucleated erythroid cell can comprise a first exogenous polypeptide that interacts with a target (e.g., an anti-drug antibody) and a second exogenous polypeptide (e.g., a protease, e.g., IdeS) that modifies the target. In embodiments, the erythroid cell is administered to a subject, e.g., a subject having a cancer, e.g., a cancer described herein.

In embodiments, an effective amount of the enucleated erythroid cells comprising a first exogenous polypeptide and a second exogenous polypeptide is less than (e.g., less by 10%, 20%, 30%, 40%, 50%, 60%, 70%, 80%, 90%, 95%, 98%, 99%, 99.5%, 99.9%, or 99.99%) an effective amount of otherwise similar enucleated erythroid cells that lack the first exogenous polypeptide or lack the second exogenous polypeptide. In embodiments, the preselected amount is an effective dose or an in vitro effective amount of enucleated erythroid cells. In embodiments, the preselected amount (e.g., in vitro effective amount) is an amount that is effective in an assay, e.g., to convert at least 10%, 20%, 30%, 405, 50%, 60%, 70%, 80%, or 90% of substrate into produce in a preselected amount of time, e.g., 1, 2, 3, 4, 5, or 6 hours. In embodiments, the preselected amount (e.g., in vitro effective amount) is effective to cleave at least 50% of a target antibody in 5 hours. The assay may measure, e.g., reduction in levels of soluble, unmodified (e.g., non-cleaved) target in a solution.

In embodiments, the reference value for targets is the number of targets in the peripheral blood of the subject at the time of administration. In embodiments (e.g., embodiments involving an in vitro effective amount of cells) the reference value for targets is the number of targets in a reaction mixture for an assay.

First Exogenous Polypeptide (e.g., a Binding Agent)

The first exogenous polypeptide can bind a target. In embodiments, the first exogenous polypeptide comprises a binding domain that recognizes an antibody, e.g., an anti-drug antibody.

In embodiments, the first exogenous polypeptide comprises a binding domain and a membrane anchor domain (e.g., a transmembrane domain, e.g., type I or type II red blood cell transmembrane domain). In embodiments, the membrane anchor domain is C-terminal or N-terminal of the modifier (e.g., protease) domain. In embodiments, the transmembrane domain comprises GPA or a transmembrane portion thereof, e.g., as set out in SEQ ID NO: 9 herein or a transmembrane portion thereof, or a polypeptide having at least 70%, 75%, 80%, 85%, 90%, 95%, 96%, 97%, 98%, 99% identity to any of the foregoing. In embodiments, the GPA polypeptide is C-terminal of the binding domain.

In embodiments, the first exogenous polypeptide comprises an address moiety or targeting moiety described in WO2007030708, e.g., in pages 34-45 therein, which application is herein incorporated by reference in its entirety.

Other examples of proteins that can be suitably adapted for use as the first exogenous polypeptide include ligand binding domains of receptors, such as where the target is the receptor ligand. Conversely, the first exogenous polypeptide can comprise a receptor ligand where the target is the receptor. A target ligand can be a polypeptide or a small molecule ligand.

In a further embodiment, a first exogenous polypeptide may comprise a domain derived from a polypeptide that has an immunoglobulin-like fold, such as the 10th type III domain of human fibronectin ("Fn3"). See U.S. Pat. Nos. 6,673,901; 6,462,189. Fn3 is small (about 95 residues), monomeric, soluble and stable. It does not have disulfide bonds which permit improved stability in reducing environments. The structure may be described as a beta-sandwich similar to that of Ab VH domain except that Fn3 has seven beta-strands instead of nine. There are three loops on each end of Fn3; and the positions of three of these loops correspond to those of CDR1, 2 and 3 of the VH domain. The 94 amino acid Fn3 sequence is:

(SEQ ID NO: 18)
VSDVPRDLEWAATPTSLLISWDAPAVTVRYYRITYGETGGNSPVQEFTV

PGSKSTATISGLKPGVDYTITGYAVTGRGDSPASSKPISINYRT

The amino acid positions of the CDR-like loops will be defined as residues 23-30 (BC Loop), 52-56 (DE Loop) and 77-87 (FG Loop). Accordingly, one or more of the CDR-like loops may be modified or randomized, to generate a library of Fn3 binding domains which may then be screened for binding to a desired address binding site. See also PCT Publication WO0232925.

Fn3 is an example of a large subfamily of the immunoglobulin superfamily (IgSF). The Fn3 family includes cell adhesion molecules, cell surface hormone and cytokine receptors, chaperonin, and carbohydrate-binding domains, all of which may also be adapted for use as binding agents. Additionally, the structure of the DNA binding domains of the transcription factor NF-kB is also closely related to the Fn3 fold and may also be adapted for use as a binding agent. Similarly, serum albumin, such as human serum albumin contains an immunoglobulin-like fold that can be adapted for use as a targeting moiety.

In still other embodiments, the first exogenous polypeptide can comprise an engineered polypeptide sequence that was selected, e.g., synthetically evolved, based on its kinetics and selectivity for binding to the address site. In embodiments, the sequence of the first exogenous polypeptide is designed using a screen or selection method, e.g., by phage display or yeast two-hybrid screen.

In some embodiments, the first exogenous polypeptide comprises a peptide ligand for a soluble receptor (and optionally the target comprises a soluble receptor), a synthetic peptide that binds a target, a complement regulatory domain (and optionally the target comprises a complement factor), or a ligand for a cell surface receptor (and optionally the target comprises the cell surface receptor).

Second Exogenous Polypeptide (e.g., Protease)

In embodiments, the second exogenous polypeptide (which modifies the target) is a factor set out in Table 4. In some embodiments, the protease is a protease set out in Table 4. In embodiments, the protease is a bacterial protease, a human protease, or a plant protease, or a fragment or variant thereof.

In embodiments, the second exogenous polypeptide (which modifies the target) is a protease. Exemplary proteases include those classified as Aminopeptidases; Dipeptidases; Dipeptidyl-peptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Aspartic proteinases; Metalloproteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidase, d-stereospecific aminopeptidase, and aminopeptidase. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, and beta-ala-his dipeptidase. Dipeptidyl-peptidases and tripeptidyl peptidases include dipeptidyl-peptidase I, dipeptidyl-peptidase II, dipeptidyl peptidase III, dipeptidyl-peptidase IV, dipeptidyl-dipeptidase, tripeptidyl-peptidase I, and tripeptidyl-peptidase II. Peptidyl-dipeptidases include peptidyl-dipeptidase A and peptidyl-dipeptidase B. Serine-type carboxypeptidases include lysosomal pro-x carboxypeptidase, serine-type D-ala-D-ala carboxypeptidase, carboxypeptidase C, and carboxypeptidase D. Metallocarboxypeptidases include carboxypeptidase A, carboxypeptidase B, lysine(arginine) carboxypeptidase, gly-X carboxypeptidase, alanine carboxypeptidase, muramoylpentapeptide carboxypeptidase, carboxypeptidase H, glutamate carboxypeptidase, carboxypeptidase M, muramoyltetrapeptide carboxypeptidase, zinc D-ala-D-ala carboxypeptidase, carboxypeptidase A2, membrane pro-x carboxypeptidase, tubulinyl-tyr carboxypeptidase, and carboxypeptidase T. Omegapeptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, and acylmuramoyl-ala peptidase. Serine proteinases include chymotrypsin, chymotrypsin C, metridin, trypsin, thrombin, coagulation factor Xa, plasmin, enteropeptidase, acrosin, alpha-lytic protease, glutamyl, endopeptidase, cathepsin G, coagulation factor VIIa, coagulation factor IXa, cucumisi, prolyl oligopeptidase, coagulation factor XIa, brachyurin, plasma kallikrein, tissue kallikrein, pancreatic elastase, leukocyte elastase, coagulation factor XIIa, chymase, complement component clr55, complement component c1s55, classical-complement pathway c3/c5 convertase, complement factor I, complement factor D, alternative-complement pathway c3/c5 convertase, cerevisin, hypodermin C, lysyl endopeptidase, endopeptidase 1a, gamma-reni, venombin AB, leucyl endopeptidase, tryptase, scutelarin, kexin, subtilisin, oryzin, endopeptidase K, thermomycolin, thermitase, endopeptidase SO, T-plasminogen activator, protein C, pancreatic endopeptidase E, pancreatic elastase II, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, limulus clotting factor C, limulus clotting factor, limulus clotting enzyme, omptin, repressor lexa, bacterial leader peptidase I, and togavirin, flavirin. Cysteine proteinases include cathepsin B, papain, ficin, chymopapain, asclepain, clostripain, streptopain, actinide, cathepsin 1, cathepsin H, calpain, cathepsin T, glycyl, endopeptidase, cancer procoagulant, cathepsin S, picornain 3C, picornain 2A, caricain, ananain, stem bromelain, fruit bromelain, legumain, histolysain, and interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin A, scytalidopepsin B, xanthomonapepsin, cathepsin E, barrierpepsin, bacterial leader peptidase I, pseudomonapepsin, and plasmepsin. Metalloproteinases include atrolysin A, microbial collagenase, leucolysin, interstitial collagenase, neprilysin, envelysin, IgA-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin 2, matrilysin gelatinase, aeromonolysin, pseudolysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, and toxilysin. Proteinases of unknown mechanism include thermopsin and multicatalytic endopeptidase complex. In embodiments, the second exogenous polypeptide comprises a fragment or variant of any of the foregoing.

In embodiments, the second exogenous polypeptide comprises an IdeS polypeptide. In some embodiments, the IdeS polypeptide comprises the sequence set out below as SEQ ID NO: 8 or a proteolytically active fragment of the sequence of SEQ ID NO: 8 (e.g., a fragment of at least 100, 150, 200, 250, or 300 amino acids) or a sequence having at least 70%, 75%, 80%, 85%, 90%, 95%, 96%, 97%, 98%, 99% identity to any of the foregoing. In some embodiments involving nucleic acids, the nucleic acid encodes an IdeS polypeptide having the sequence set out below as SEQ ID NO: 8, or a proteolytically active fragment thereof, or a sequence having at least 70%, 75%, 80%, 85%, 90%, 95%, 96%, 97%, 98%, 99% identity to any of the foregoing.

IdeS polypeptide:
(SEQ ID NO: 8)
DSFSANQEIRYSEVTPYHVTSVWTKGVTPPAKFTQGEDVFHAPYVANQGW

YDITKTFNGKDDLLCGAATAGNMLHWWFDQNKEKIEAYLKKHPDKQKIMF

GDQELLDVRKVINTKGDQTNSELFNYFRDKAFPGLSARRIGVMPDLVLDM

FINGYYLNVYKTQTTDVNRTYQEKDRRGGIFDAVFTRGDQSKLLTSRHDF

KEKNLKEISDLIKKELTEGKALGLSHTYANVRINHVINLWGADFDSNGNL

KAIYVTDSDSNASIGMKKYFVGVNSAGKVAISAKEIKEDNIGAQVLGLFT

LSTGQDSWNQTN

In embodiments, the second exogenous polypeptide comprises a modifier domain (e.g., a protease domain, e.g., an IdeS polypeptide) and a membrane anchor domain (e.g., a transmembrane domain, e.g., type I or type II red blood cell transmembrane domain). In embodiments, the membrane anchor domain is C-terminal or N-terminal of the modifier (e.g., protease) domain. In embodiments, the transmembrane domain comprises GPA or a transmembrane portion thereof. In embodiments, the GPA polypeptide has a sequence of:

(SEQ ID NO: 9)
LSTTEVAMHTSTSSSVTKSYISSQTNDTHKRDTYAATPRAHEVSEISVRT

VYPPEEETGERVQLAHHFSEPEITLIIFGVMAGVIGTILLISYGIRRLIK

KSPSDVKPLPSPDTDVPLSSVEIENPETSDQ or a transmembrane portion thereof, or a polypeptide having at least 70%, 75%, 80%, 85%, 90%, 95%, 96%, 97%, 98%, 99% identity to any of the foregoing. In embodiments, the GPA polypeptide is C-terminal of the modifier (e.g., protease) domain.

In some embodiments, a linker is disposed between the IdeS polypeptide and the transmembrane polypeptide, e.g., a glycine-serine linker, e.g., a linker comprising a sequence of GGSGGSGG (SEQ ID NO: 10) and/or GGGSGGGS (SEQ ID NO: 11).

In some embodiments, the exogenous polypeptide, e.g., the second exogenous polypeptide, e.g., a protease, e.g., IdeS polypeptide, comprises a leader sequence, e.g., a GPA leader sequence, e.g., MYGKIIFVLLLSEIVSISA (SEQ ID NO: 12).

In some embodiments, the exogenous polypeptide, e.g., the second exogenous polypeptide further comprises a tag, e.g., an HA tag or a FLAG tag.

In some embodiments, the protease (e.g., immunoglobulin degrading enzyme, e.g., immunoglobulin-G degrading enzyme, e.g., IdeS) cleaves an immunoglobulin at a hinge region, a CH2 region, or between a hinge and CH2 region. In embodiments, the protease cleaves an immunoglobulin at one of the sequences below, e.g., between the two italicized glycines or the italicized alanine and glycine in the sequences below.

Human IgG1 Hinge/CH2 Sequence
(SEQ ID NO: 13)
CPPCPAPELLGGPSVF

Human IgG2 Hinge/CH2 Sequence
(SEQ ID NO: 14)
CPPCPAPPVAGPSVF

Human IgG3 Hinge/CH2 Sequence
(SEQ ID NO: 15)
CPRCPAPELLGGPSVF

Human IgG4 Hinge/CH2 Sequence
(SEQ ID NO: 16)
AHHAQAPEFLGGPSVF

In embodiments, the protease (e.g., a bacterial protease) cleaves IgG, e.g., IdeS or IgA protease.

In embodiments, the protease (e.g., a papain family protease, e.g., papain) cleaves an immunoglobulin between the Fc and Fab regions, e.g., a histidine-threonine bond between positions 224 and 225 of the heavy chain and/or a glutamic acid-leucine bond between positions 233 and 234 of the heavy chain.

In embodiments, the protease or other modifier acts on a target listed in Table 4.

In embodiments, the second exogenous polypeptide comprises a catalytic moiety described in WO2007030708, e.g., in pages 45-46 therein, which application is herein incorporated by reference in its entirety.

The second exogenous polypeptide can comprise a moiety capable of acting on a target to induce a chemical change, thereby modulate its activity, e.g., a moiety capable of catalyzing a reaction within a target. The second exogenous polypeptide can comprise a naturally occurring enzyme, an active (e.g., catalytically active) fragment thereof, or an engineered enzyme, e.g., a protein engineered to have an enzymatic activity, such as a protein designed to contain a serine protease active motif. A catalytic domain of a second exogenous polypeptide may comprise the arrangement of amino acids that are effective to induce the desired chemical change in the target. They may be N-terminal or C-terminal truncated versions of natural enzymes, mutated versions, zymogens, or complete globular domains.

The second exogenous polypeptide can comprise an enzymatically active site that alone is promiscuous, binding with a cleavage site it recognizes on many different biomolecules, and may have relatively poor reaction kinetics. In embodiments, the first exogenous polypeptide supplies or improves specificity by increasing the local concentration of target near the second exogenous polypeptide.

The second exogenous polypeptide can, in embodiments, modify the target so that it is recognized and acted upon by another enzyme (e.g., an enzyme that is already present in a subject). In an embodiment, the second exogenous polypeptide comprises a moiety that alters the structure of the target so that its activity is inhibited or upregulated. Many naturally occurring enzymes activate other enzymes, and these can be exploited in accordance with the compositions and methods described herein.

The second exogenous polypeptide can comprise a protease, a glycosidase, a lipase, or other hydrolases, an amidase (e.g., N-acetylmuramoyl-L-alanine amidase, PGRP-L amidase), or other enzymatic activity, including isomerases, transferases (including kinases), lyases, oxidoreductases, oxidases, aldolases, ketolases, glycosidases, transferases and the like. In embodiments, the second exogenous polypeptide comprises human lysozyme, a functional portion of a human lysozyme, a human PGRP-L, a functional portion of a human PGRP-L, a phospholipase A2, a functional portion of a phospholipase A2, or a matrix metalloproteinase (MMP) extracellular enzyme such as MMP-2 (gelatinase A) or MMP-9 (gelatinase B).

In embodiments, the second exogenous polypeptide is a serine proteinase, e.g., of the chymotrypsin family which includes the mammalian enzymes such as chymotrypsin, trypsin or elastase or kallikrein, or the substilisin family which includes the bacterial enzymes such as subtilisin. The general three-dimensional structure is different in the two families but they have the same active site geometry and catalysis proceeds via the same mechanism. The serine proteinases exhibit different substrate specificities which are related to amino acid substitutions in the various enzyme subsites interacting with the substrate residues. Three residues which form the catalytic triad are important in the catalytic process: His-57, Asp-102 and Ser-195 (chymotrypsinogen numbering).

In embodiments, the second exogenous polypeptide is a cysteine proteinase which includes the plant proteases such as papain, actinidin or bromelain, several mammalian lysosomal cathepsins, the cytosolic calpains (calcium-activated), and several parasitic proteases (e.g., *Trypanosoma, Schistosoma*). Papain is the archetype and the best studied member of the family. Like the serine proteinases, catalysis proceeds through the formation of a covalent intermediate and involves a cysteine and a histidine residue. The essential Cys-25 and His-159 (papain numbering) play the same role as Ser-195 and His-57 respectively. The nucleophile is a thiolate ion rather than a hydroxyl group. The thiolate ion is stabilized through the formation of an ion pair with neighboring imidazolium group of His-159. The attacking nucleophile is the thiolate-imidazolium ion pair in both steps and then a water molecule is not required.

In embodiments, the second exogenous polypeptide is an aspartic proteinase, most of which belong to the pepsin family. The pepsin family includes digestive enzymes such as pepsin and chymosin as well as lysosomal cathepsins D, processing enzymes such as renin, and certain fungal proteases (penicillopepsin, rhizopuspepsin, endothiapepsin). A second family comprises viral proteinases such as the protease from the AIDS virus (HIV) also called retropepsin. In contrast to serine and cysteine proteinases, catalysis by aspartic proteinases does not involve a covalent intermediate, though a tetrahedral intermediate exists. The nucleophilic attack is achieved by two simultaneous proton transfers: one from a water molecule to the dyad of the two carboxyl groups and a second one from the dyad to the carbonyl oxygen of the substrate with the concurrent CO—NH bond cleavage. This general acid-base catalysis, which may be called a "push-pull" mechanism leads to the formation of a non-covalent neutral tetrahedral intermediate.

In embodiments, the second exogenous polypeptide is a metalloproteinase, which can be found in bacteria, fungi as well as in higher organisms. They differ widely in their sequences and their structures but the great majority of enzymes contain a zinc (Zn) atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non-covalent tetrahedral intermediate after the attack of a zinc-bound water molecule on the carbonyl group of the scissile bond. This intermediate is further decomposed by transfer of the glutamic acid proton to the leaving group.

In embodiments, the second exogenous polypeptide comprises an isomerase (e.g., an isomerase that breaks and forms chemical bonds or catalyzes a conformational change). In embodiments, the isomerase is a racemase (e.g., amino acid racemase), epimerase, cis-trans isomerase, intramolecular oxidoreductase, intramolecular transferase, or intramolecular lyase.

In embodiments, the second exogenous protease comprises a chaperone. For instance, the chaperone can be a general chaperone (e.g., GRP78/BiP, GRP94, GRP170), a lectin chaperone (e.g., calnexin or calreticulin), a non-classical molecular chaperone (e.g., HSP47 or ERp29), a folding chaperone (e.g., PDI, PPI, or ERp57), a bacterial or archaeal chaperone (e.g., Hsp60, GroEL/GroES complex, Hsp70, DnaK, Hsp90, HtpG, Hsp100, Clp family (e.g., ClpA and ClpX), Hsp104). In embodiments, the enucleated erythrocyte comprises a co-chaperone, e.g., immunophilin, Sti1, p50 (Cdc37), or Aha1. In embodiments, the molecular chaperone is a chaperonin.

Candidates for the second exogenous protein (which modifies a target) can be screened based on their activity. Depending on the specific activity of each molecule being tested, an assay appropriate for that molecule can be used. For example, if the second exogenous protein is a protease, the assay used to screen the protease can be an assay to detect cleavage products generated by the protease, e.g., a chromatography or gel electrophoresis based assay.

In an example, the second exogenous polypeptide may have kinase activity. An assay for kinase activity could measure the amount of phosphate that is covalently incorporated into the target of interest. For example, the phosphate incorporated into the target of interest could be a radioisotope of phosphate that can be quantitated by measuring the emission of radiation using a scintillation counter.

Targets and Indications

In embodiments, the target is a target listed in Table 4.

In embodiments, the target is an immune checkpoint molecule selected from PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGF beta. In embodiments, the target is an inhibitory ligand listed in Table 3, and the first exogenous polypeptide optionally comprises a binding domain from a corresponding target receptor of Table 3. In some embodiments, the target is a target receptor of Table 3, and the first exogenous polypeptide optionally comprises a binding domain from a corresponding inhibitory ligand of Table 3. In some embodiments, the second exogenous polypeptide comprises a protease that cleaves an immune checkpoint molecule, e.g., trypsin. In embodiments, e.g., for treating cancer, a T cell is activated or prevented from being inactivated, e.g., by contacting its receptor (e.g., a receptor of Table 3) with a molecule that blocks T cell inhibition.

In embodiments, the target is an antibody e.g., a human antibody.

Figure 7:
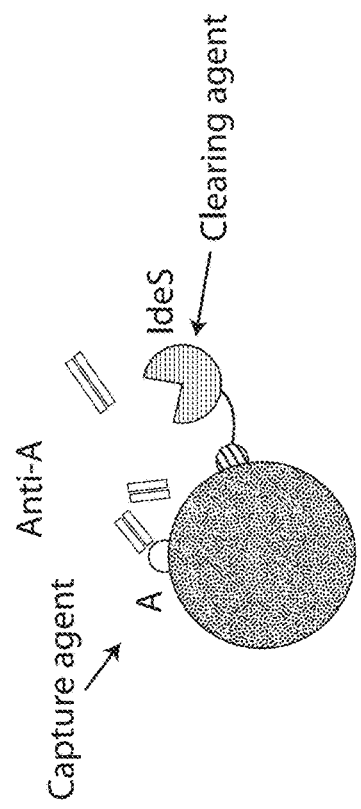
FIG. 7 is a diagram of an erythroid cell comprising a first exogenous polypeptide that binds a target, e.g., an unwanted anti-drug antibody produced by a subject in reaction to treatment with a drug, a second exogenous polypeptide that cleaves the target, and an optional third exogenous polypeptide comprising a therapeutic protein, e.g., an alternative to the drug against which the subject produced anti-drug antibodies.

Engineered erythroid cells described herein can also be used to treat a subject that has antibodies against a drug (e.g., see FIG. 7). The erythroid cell can reduce levels of anti-drug antibodies in a subject, and can optionally further comprise a therapeutic protein that treats the disease. For instance, the erythroid cell comprises a first exogenous polypeptide that binds a target, e.g., wherein the target is an anti-drug antibody. The erythroid cell can further comprise a second exogenous polypeptide (e.g., IdeS) that inactivates, e.g., cleaves the target. The erythroid cell may optionally further comprise a third exogenous polypeptide, e.g., a therapeutic protein that treats the same disease as the prior therapeutic to which the subject developed anti-drug antibodies, e.g., a therapeutic protein which is the same as or different from the prior therapeutic to which the subject developed anti-drug antibodies. In embodiments, the subject comprises anti-drug antibodies against an anti-CD20 antibody molecule, anti-VEGF-A antibody molecule, anti-HER2 antibody molecule, an G-CSF analogue such as filgrastim, anti EGFR antibody molecule (e.g., cetuximab), an erythropoietin, e.g., epoetin, or an interferon e.g., IFNβ1a or IFNβ1b. In such methods of treatment, the patient may be tested for the presence of anti-drug antibodies, e.g., for the presence of neutralizing anti-drug antibodies, before, during and/or after administration of the engineered erythroid cells described herein.

Agent-Synergistic Configurations

When two or more agents (e.g., polypeptides) are agent-synergistic, the agents act on two or more different targets within a single pathway. In an embodiment, the action of the two or more agents together is greater than the action of any of the individual agents. For example, the first and second polypeptides are ligands for cellular receptors that signal to the same downstream target. For example, the first exogenous polypeptide comprises a ligand for a first target cellular receptor, and the second exogenous polypeptide comprises a ligand for a second target cellular receptor, e.g., which first and second target cellular receptors signal to the same downstream target. In embodiments, the first exogenous polypeptide acts on the first target and the second exogenous polypeptide acts on the second target simultaneously, e.g., there is some temporal overlap in binding of the first exogenous polypeptide to the first target and binding of the second exogenous polypeptide to the second target. In some embodiments the simultaneous action generates a synergistic response of greater magnitude than would be expected when either target is acted on alone or in isolation.

In an embodiment, the first and second polypeptides are ligands for a first cellular receptor and a second cellular receptor that mediates apoptosis. In an embodiment the agents comprise two or more TRAIL receptor ligands, e.g., wild-type or mutant TRAIL polypeptides, or antibody molecules that bind TRAIL receptors, and induce apoptosis in a target cell, e.g., a cancer cell. In some embodiments, an enucleated RBC comprising TRAIL receptor ligands is used to treat NSCLC. In some embodiments, a RBC comprising TRAIL receptor ligands further comprises a targeting moiety, e.g., a targeting moiety described herein. In an embodiment the first target and the second target interacts with the same substrate, e.g., a substrate protein. In an embodiment the first target and the second target interact with different substrates.

TRAIL (TNF-related apoptosis inducing ligand) is a member of the TNF family that induces apoptosis. TRAIL has at least two receptors, TRAIL R1 and TRAIL R2. TRAIL receptor agonists, e.g., mutants of TRAIL that bind one or more of the receptors, or antibody molecules that bind one or both of TRAIL R1 or TRAIL R2 (see, e.g. Gasparian et al., Apoptosis 2009 Jun. 14(6), Buchsbaum et al. Future Oncol 2007 Aug. 3(4)), have been developed as a clinical therapy for a wide range of cancers. Clinical trials of TRAIL receptor agonists have failed for, among other reasons, the fact that many primary cancers are not sensitive to signaling through a single receptor but rather require engagement of both receptors to induce cytotoxicity (Marconi et al., Cell Death and Disease (2013) 4, e863). In one embodiment the agents expressed on the engineered blood cell are single receptor-specific TRAIL agonists that, in combination, enable the cell to engage and agonize both TRAIL receptors simultaneously, thus leading to a synergistic induction of apoptosis of a target cancer cell. Thus, in some embodiments, the enucleated red blood cell (e.g., reticulocyte) comprises on its surface a first polypeptide that binds TRAIL R1 and a second polypeptide that binds TRAIL R2. In embodiments, each polypeptide has a Kd for TRAIL R1 or TRAIL R2 that is 2, 3, 4, 5, 10, 20, 50, 100, 200, or 500-fold stronger than the Kd for the other receptor. While not wishing to be bound by theory, in some embodiments an enucleated red blood cell comprising a TRAIL R1-specific ligand and a TRAIL R2-specific ligand promote better heterodimerization of TRAIL R1 and TRAIL R2 than an enucleated red blood cell comprising a ligand that binds to TRAIL R1 and TRAIL R2 with about the same affinity.

In some embodiments, one, two, or more of the exogenous polypeptides are members of the TNF superfamily. In some embodiments, the exogenous polypeptides bind to one or both of death receptors DR4 (TRAIL-R1) and DR5 (TRAIL-R2). In some embodiments, the exogenous polypeptides bind to one or more of TNFRSF10A/TRAILR1, TNFRSF10B/TRAILR2, TNFRSF10C/TRAILR3, TNFRSF10D/TRAILR4, or TNFRSF11B/OPG. In some embodiments, the exogenous polypeptides activate one or more of MAPK8/JNK, caspase 8, and caspase 3.

In some embodiments, a TRAIL polypeptide is a TRAIL agonist having a sequence of any of SEQ ID NOS: 1-5 herein, or a sequence with at least 70%, 80%, 85%, 90%, 95%, 96%, 97%, 98%, or 99% identity thereto. Sequence identity is measured, e.g., by BLAST (Basic Local Alignment Search Tool). SEQ ID Nos. 1-5 are further described in Mohr et al. BMC Cancer (2015) 15:494), which is herein incorporated by reference in its entirety.

Soluble TRAIL variant DR4-1

SEQ ID NO: 1

MAMMEVQGGPSLGQTCVLIVIFTVLLQSLCVAVTYVYFTNELKQMQDKYS

KSGIACELKEDDSYWDPNDEESMNSPCWQVKWQLRQLVRKMILRTSEETI

STVQEKQQNISPLVRERGPQRVAAHITGTRRRSNTLSSPNSKNEKALGRK

INSWESSRSGHSFLSNLHLRNGELVIHEKGFYYIYSQTYFRFQEEIKENT

KNDKQMVQYIYKYTSYPDPILLMKSARNSCWSKDAEYGLYSIYQGGIFEL

KENDRIFVSVTNEHLIDMDHEASFFGAFLVG

Soluble TRAIL variant DR4-2

SEQ ID NO: 2

MAMMEVQGGPSLGQTCVLIVIFTVLLQSLCVAVTYVYFTNELKQMQDKYS

KSGIACELKEDDSYWDPNDEESMNSPCWQVKWQLRQLVRKMILRTSEETI

STVQEKQQNISPLVRERGPQRVAAHITGTRGRSNTLSSPNSKNEKALGRK

```
-continued
INSWESSRRGHSFLSNLHLRNGELVIHEKGFYYIYSQTYFRFQEEIKENT

KNDKQMVQYIYKYTSYPDPILLMKSARNSCWSKDAEYGLYSIYQGGIFEL

KENDRIFVSVTNEHLIDMDHEASFFGAFLVG

Soluble TRAIL variant DR4-3
                                        SEQ ID NO: 3
MAMMEVQGGPSLGQTCVLIVIFTVLLQSLCVAVTYVYFTNELKQMQDKYS

KSGIACELKEDDSYWDPNDEESMNSPCWQVKWQLRQLVRKMILRTSEETI

STVQEKQQNISPLVRERGPQRVAAHITGTRRRSNTLSSPNSKNEKALGIK

INSWESSRRGHSFLSNLHLRNGELVIHEKGFYYIYSQTYFRFQEEIKENT

KNDKQMVQYIYKYTDYPDPILLMKSARNSCWSKDAEYGLYSIYQGGIFEL

KENDRIFVSVTNEHLIDMDHEASFFGAFLVG

Soluble TRAIL variant DR5-1
                                        SEQ ID NO: 4
MAMMEVQGGPSLGQTCVLIVIFTVLLQSLCVAVTYVYFTNELKQMQDKYS

KSGIACELKEDDSYWDPNDEESMNSPCWQVKWQLRQLVRKMILRTSEETI

STVQEKQQNISPLVRERGPQRVAAHITGTRGRSNTLSSPNSKNEKALGRK

INSWESSRSGHSFLSNLHLRNGELVIHEKGFYYIYSQTYFRFQEEIKENT

KNDKQMVQYIYKYTSYPDPILLMKSARNSCWSKDAEYGLYSIYQGGIFEL

KENDRIFVSVTNEHLIDMHHEASFFGAFLVG

Soluble TRAIL variant DR5-2
                                        SEQ ID NO: 5
MAMMEVQGGPSLGQTCVLIVIFTVLLQSLCVAVTYVYFTNELKQMQDKYS

KSGIACELKEDDSYWDPNDEESMNSPCWQVKWQLRQLVRKMILRTSEETI

STVQEKQQNISPLVRERGPQRVAAHITGTRGRSNTLSSPNSKNEKALGRK

INSWESSRSGHSFLSNLHLRNGELVIHEKGFYYIYSQTYFRFQERIKENT

KNDKQMVQYIYKYTSYPDPILLMKSARNSCWSKDAEYGLYSIYQGGIFEL

KENDRIFVSVTNEHLIDMHHEASFFGAFLVG
```

All combinations of the TRAIL receptor ligands are envisioned. In some embodiments, the first and second agents comprise SEQ ID NO: 1 and SEQ ID NO: 2; SEQ ID NO: 1 and SEQ ID NO: 3; SEQ ID NO: 1 and SEQ ID NO: 4; SEQ ID NO: 1 and SEQ ID NO: 5; SEQ ID NO: 2 and SEQ ID NO: 3; SEQ ID NO: 2 and SEQ ID NO: 4; SEQ ID NO: 2 and SEQ ID NO: 5; SEQ ID NO: 3 and SEQ ID NO: 4; SEQ ID NO: 3 and SEQ ID NO: 5; or SEQ ID NO: 4 and SEQ ID NO: 5, or a fragment or variant of any of the foregoing.

In some embodiments, the TRAIL receptor ligand comprises an antibody molecule. In embodiments, the antibody molecule recognizes one or both of TRAIL R1 and TRAIL R2. The antibody molecule may be, e.g., Mapatumumab (human anti-DR4 mAb), Tigatuzumab (humanized anti-DR5 mAb), Lexatumumab (human anti-DR5 mAb), Conatumumab (human anti-DR5 mAb), or Apomab (human anti-DR5 mAb). In some embodiments, the enucleated red blood cell (e.g., reticulocyte) comprises two or more (e.g., three, four, five, or more) different antibody molecules that bind a TRAIL receptor. In some embodiments, the enucleated red blood cell (e.g., reticulocyte) comprises at least one antibody molecule that binds a TRAIL receptor and at least one TRAIL polypeptide.

In some embodiments, the agents are modulators of a multi-step pathway that act agent-synergistically by targeting upstream and downstream steps of the pathway, e.g., simultaneously.

Multiplicative Configurations

When two or more agents (e.g., polypeptides) are multiplicative, a first agent acts on a first molecule that is part of a first pathway and a second agent acts on a second molecule that is part of a second pathway, which pathways act in concert toward a desired response.

In some embodiments, the desired response is cell death, e.g., of a cancer cell. Without wishing to be bound by theory, in cancer treatment it may be beneficial to activate endogenous or exogenous anti-tumor T cells that are anergic or otherwise non-functioning, e.g., due to the tumor or tumor microenvironment. In some embodiments, the agents trigger multiple T cell activation pathways to induce an anti-cancer immune response. In some embodiments, the engineered erythroid cell promotes T cell proliferation. In embodiments, one or more (e.g., 2, 3, 4, or 5 or more) T cell activation ligands comprise a ligand of Table 2 or a T-cell activating variant (e.g., fragment) thereof.

In embodiments, one or more (e.g., 2, 3, 4, or 5 or more) T cell activation ligands comprise an antibody molecule that binds a target receptor of Table 2 or a T-cell activating variant (e.g., fragment) thereof. In some embodiments, the first and second polypeptides comprise different T cell activation ligands, e.g. CD80, 41BB-ligand, CD86, or any combination thereof, to stimulate T cells and overcome anergy in an immuno-oncology setting. In some embodiments, the enucleated red blood cell (e.g., reticulocyte) comprises 4-1BBL, OX40L, and CD40L, or fragments or variants thereof. In embodiments, these proteins signal through complementary activation pathways. In some embodiments the ligands are activating cytokines, interferons, or TNF family members (e.g., of Table 1), e.g. IFNa, IL2, or IL6 or any combination thereof. In some embodiments the agents are combinations of the above classes of molecules. The agents can be derived from endogenous ligands or antibody molecules to the target receptors.

TABLE 2

| T cell activation | |
|---|---|
| Activating Ligand | Target Receptor on T cell |
| B7-H2 (e.g., Accession Number NP_056074.1) | ICOS, CD28 (e.g., Accession Number NP_006130.1) |
| B7-1 (e.g., Accession Number NP_005182.1) | CD28 (e.g., Accession Number NP_006130.1) |
| B7-2 (e.g., Accession Number AAA86473) | CD28 (e.g., Accession Number NP_006130.1) |
| CD70 (e.g., Accession Number NP_001243.1) | CD27 (e.g., Accession Number NP_001233.1) |
| LIGHT (e.g., Accession Number NP_003798.2) | HVEM (e.g., Accession Number AAQ89238.1) |

TABLE 2-continued

| T cell activation | |
| --- | --- |
| Activating Ligand | Target Receptor on T cell |
| HVEM (e.g., Accession Number AAQ89238.1) | LIGHT (e.g., Accession Number NP_003798.2) |
| CD40L (e.g., Accession Number BAA06599.1) | CD40 (e.g., Accession Number NP_001241.1) |
| 4-1BBL (e.g., Accession Number NP_003802.1) | 4-1BB (e.g., Accession NP_001552.2) |
| OX40L (e.g., Accession Number NP_003317.1) | OX40 (e.g., Accession Number NP_003318.1) |
| TL1A (e.g., Accession Number NP_005109.2) | DR3 (e.g., Accession Number NP_683866.1) |
| GITRL (e.g., Accession Number NP_005083.2) | GITR (e.g., Accession Number NP_004186.1) |
| CD30L (e.g., Accession Number NP_001235.1), | CD30 (e.g., Accession Number NP_001234.3) |
| TIM4 (e.g., Accession Number NP_612388.2) | TIM1 (e.g., Accession Number NP_036338.2) |
| SLAM (e.g., Accession Number AAK77968.1) | SLAM (e.g., Accession Number AAK77968.1) |
| CD48 (e.g., Accession Number CAG33293.1) | CD2 (e.g., Accession Number NP_001315538.1) |
| CD58 (e.g., Accession Number CAG33220.1) | CD2 (e.g., Accession Number NP_001315538.1) |
| CD155 (e.g., Accession Number NP_001129240.1) | CD226 (e.g., Accession Number NP_006557.2) |
| CD112 (e.g., Accession Number NP_001036189.1) | CD226 (e.g., Accession Number NP_006557.2) |
| CD137L (e.g., Accession Number NP_003802.1) | CD137 (e.g., Accession NP_001552.2) |

In some embodiments, an anti-IL6 or TNFa antibody molecule comprises a sequence of either of SEQ ID NO: 6 or 7 herein, or a sequence with at least 70%, 80%, 85%, 90%, 95%, 96%, 97%, 98%, or 99% identity thereto.

```
Anti-IL6 scFv
                                           SEQ ID NO: 6
EVQLVESGGGLVQPGGSLRLSCAASGFNFNDYFMNWVRQAPGKGLEWVA

QMRNKNYQYGTYYAESLEGRFTISRDDSKNSLYLQMNSLKTEDTAVYYC

ARESYYGFTSYWGQGTLVTVSSGGGGSGGGGSGGGGSDIQMTQSPSSLS

ASVGDRVTITCQASQDIGISLSWYQQKPGKAPKLLIYNANNLADGVPSR

FSGSGSGTDFTLTISSLQPEDFATYYCLQHNSAPYTFGQGTKLEIKR

Anti-TNFα scFv
                                           SEQ ID NO: 7
EVQLVESGGGLVQPGRSLRLSCAASGFTFDDYAMHWVRQAPGKGLEWVS

AITWNSGHIDYADSVEGRFTISRDNAKNSLYLQMNSLRAEDTAVYYCAK

VSYLSTASSLDYWGQGTLVTVSSGGGGSGGGGSGGGGSDIQMTQSPSSL

SASVGDRVTITCRASQGIRNYLAWYQQKPGKAPKLLIYAASTLQSGVPS

RFSGSGSGTDFTLTISSLQPEDVATYYCQRYNRAPYTFGQGTKVEIK
```

As another example, the first and second polypeptides comprise a T cell activating ligand and an agent which inhibits an immune inhibitory molecule (e.g., an immune inhibitory receptor), e.g. CD80 and anti-PD1, in an immuno-oncology setting. In another embodiment, one agent is an activating 4-1BBL, or fragment or variant thereof, and a second agent an antibody molecule that blocks PD1 signaling (e.g., an antibody molecule to PD1 or PD-L). Thus, in embodiments, a target T cell is both activated and prevented from being repressed. Examples of agents that inhibit an immune inhibitory molecule include inhibitors of (e.g., antibody molecules that bind) PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGF beta, or a functional variant (e.g., fragment) thereof. In some embodiments, the agent that inhibits an immune inhibitory molecule is an inhibitor of an inhibitory ligand of Table 3, or an inhibitory fragment or variant thereof. In some embodiments, the agent that inhibits an immune inhibitory molecule is an antibody molecule that binds a target receptor of Table 3, or a fragment or variant thereof.

TABLE 3

| T cell inhibition | |
| --- | --- |
| Inhibitory Ligand | Target Receptor on T cell |
| B7-1 | CTLA4, B7H1 |
| B7-2 | CTLA4 |
| B7DC | PD1 |
| B7H1 | PD1, B7-1 |
| HVEM | CD160, BTLA |
| COLLAGEN | LAIR1 |
| GALECTIN9 | TIM3 |
| CD48, TIM4 | TIM4R |
| CD48 | 2B4 |
| CD155, CD112, CD113 | TIGIT |
| PDL1 | PD1 |

In some embodiments, one of the agents for treating a cancer comprises an activating cytokine, e.g., IL-2, IL-12, or another activating cytokine of Table 1, or a fragment or variant thereof.

In some embodiments the objective is to activate or to inhibit T cells. To ensure that T cells are preferentially targeted over other immune cells that may also express either activating or inhibitory receptors as described herein, one of the agents on the red blood cell (e.g., reticulocyte) may comprise a targeting moiety, e.g., an antibody molecule that binds the T cell receptor (TCR) or another T cell marker.

Targeting moieties are described in more detail in the section entitled "Localization configurations" herein. In some embodiments, a specific T cell subtype or clone may be enhanced (a T cell with anti-tumor specificity) or inhibited. In some embodiments, one or more of the agents on the red blood cell (e.g., reticulocyte) is a peptide-MHC molecule that will selectively bind to a T cell receptor in an antigen-specific manner.

In some embodiments a plurality of agents comprise multiple antigens derived from a complex target, e.g. a tumor cell, against which it is desirable to mount a complex immune response with multiple specificities.

In some embodiments, the first and second exogenous polypeptides comprise, in some embodiments, an antigen and a costimulatory molecule, e.g., wherein the erythroid cell can act as an APC, e.g., for cancer vaccination.

In some embodiments, an enucleated red blood cell (e.g., reticulocyte) comprising a first exogenous polypeptide and a second exogenous polypeptide is administered to a subject having a first target and a second target. In embodiments, the first exogenous polypeptide acts on (e.g., binds) the first target and the second exogenous polypeptide acts on the second target.

Optionally, the enucleated red blood cell comprises a third exogenous polypeptide and the patient comprises a third target. In embodiments, the third exogenous polypeptide acts on the third target.

In some embodiments an erythroid cell comprises a first exogenous polypeptide which is an agonist or antagonist of a first target in a first pathway, and further comprises a second exogenous polypeptide which is an agonist or antagonist of a second target in a second pathway, wherein the first and second pathways act in concert toward a desired response. The first and second exogenous polypeptides can both be agonists; can both be antagonists; or one can be an agonist and the other can be an antagonist. In some embodiments, one or more of the exogenous polypeptides are immune checkpoint agonists or antagonists. In some embodiments, the erythroid cell further comprises a targeting agent.

Independent Function Configurations

When two or more agents (e.g., polypeptides) have an independent function relationship, the agents have two distinct (e.g., complementary) functions. For example, a first agent binds a first target and the second agent binds a second target. The patient may lack the first or second target. Optionally, the first and second agents are in different pathways.

In sepsis, tumor lysis syndrome, and other conditions marked by a cytokine storm, the damage is driven by a diverse mix of inflammatory cytokines. Existing monotherapies against one cytokine are often insufficient to treat these acute conditions. Furthermore it can sometimes be impossible to measure the driver of the cytokine storm in time to prevent clinical damage. In an embodiment, the first and second peptides are molecules (e.g., antibody molecules) that bind two different cytokines. In some embodiments the agents bind and neutralize different cytokines and thus the engineered red cell product provides multifaceted protection from cytokine storm.

In embodiments the cytokines comprise interleukins, e.g., IL-1, IL02, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-22, IL-23, IL-25, IL-26, IL-27, IL-28, IL-29, IL-30, IL-31, IL-32, IL-33, IL-35, or IL-36. In some embodiments, the cytokine is a cytokine of Table 1 or a fragment or variant thereof. In some embodiments, the first cytokine is TNFa and the second is an interleukin, e.g., IL-6, or a fragment or variant of any of the foregoing. In some embodiments, the agents comprise anti-TNFa, anti-IL-6, or anti-IFNg antibody molecules, or any combination thereof, or a fragment or variant of any of the foregoing.

In some embodiments, an enucleated red blood cell (e.g., reticulocyte) comprising a first exogenous polypeptide and a second exogenous polypeptide is administered to a subject having a first target but not a second target, or wherein the patient is not known to have a first target or second target. In embodiments, the first exogenous polypeptide acts on (e.g., binds) the first target and the second exogenous polypeptide remains substantially unbound. Optionally, the enucleated red blood cell comprises a third exogenous polypeptide and the patient lacks a third target, or is not known to have the third target. In some embodiments, the enucleated red blood cell comprises a plurality of exogenous polypeptides, and the patient does not have, or is not known to have, targets for one or a subset of the plurality of exogenous polypeptides.

Figure 4:
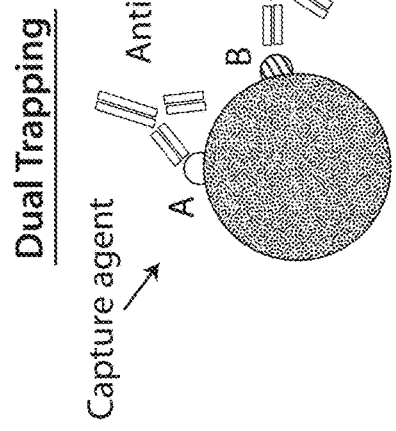
FIG. 4 is a diagram of an erythroid cell comprising a first exogenous polypeptide (white), a second exogenous polypeptide (hatching), and a third exogenous polypeptide (close hatching) wherein each exogenous polypeptide comprises a capture agent capable of trapping a target, e.g., an unwanted target. The erythroid cell can engage in dual trapping, where it uses more than one exogenous polypeptide to bind a single or multiple soluble factors.
Figure 5:
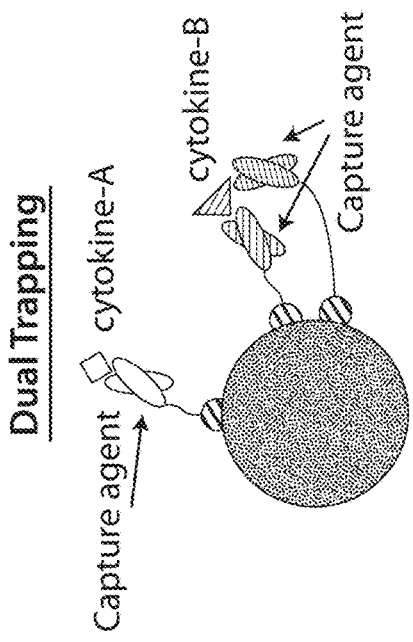
FIG. 5 is a diagram of an erythroid cell comprising a first exogenous polypeptide and a second exogenous polypeptide wherein each exogenous polypeptide is capable of trapping an antibody, e.g., unwanted antibody, e.g., an anti-drug antibody.
Figure 6:
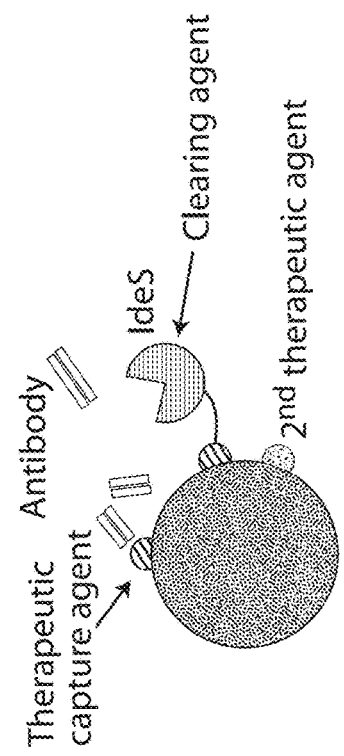
FIG. 6 is a diagram of an erythroid cell comprising a first exogenous polypeptide that binds a target, e.g., an antibody, e.g., an unwanted antibody, e.g., an anti-drug antibody, and a second exogenous polypeptide that modifies the target, e.g., cleaves the target. The second exogenous polypeptide may comprise a protease such as IdeS.

An example of an independent function configuration is shown in FIG. 4. The erythroid cell of FIG. 4 comprises a first exogenous polypeptide (white), a second exogenous polypeptide (hatching), and an optional third exogenous polypeptide (close hatching). The first exogenous polypeptide can bind a first target, e.g., cytokine A, and the second exogenous polypeptide can independently bind a second target, e.g., cytokine B. This engineered erythroid cell trap and clear both cytokines if both are present in the subject. If only one of the cytokines is present in the subject, the engineered erythroid cell can clear that cytokine. In embodiments, one or more (e.g., two or all) of the exogenous polypeptides comprise antibody molecules, e.g., scFvs, and optionally further comprise a transmembrane domain. In embodiments, the targets comprise a plurality of cytokines, chemokines, or a combination thereof.

Localization Configurations

When two or more agents (e.g., polypeptides) have a localization relationship, a first agent localizes the RBC to a site of action that enhances the activity of the second or other agent or agents compared to their activity when not localized to the site of action (e.g., by binding of the first agent to its target, there is an increase in the local concentration of the second agent in the area of its target). In some embodiments one agent serves to target the red blood cell (e.g., reticulocyte) to a site of action and one or more agents have a therapeutic effect. In an embodiment, binding of the first agent increases the activity of an entity, e.g., polypeptide, bound by the second agent. In an embodiment, the first agent binds to a substrate or product of the entity, e.g., polypeptide, bound by the second agent. The agent that localizes the RBC may be, e.g., a ligand for a receptor on a target cell, or an antibody that binds a cell surface molecule on a target cell.

Figure 9:
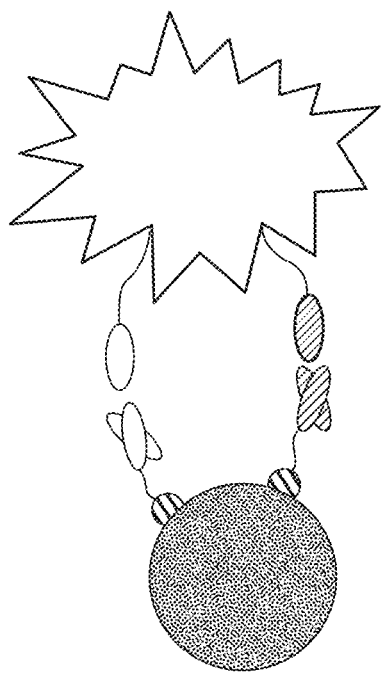
FIG. 9 is a diagram of an erythroid cell comprising a first exogenous polypeptide with a first targeting agent and a second exogenous polypeptide with a second targeting agent.

As shown in FIG. 9, the cell can comprise one or more targeting agents. The targeting agent can be an exogenous polypeptide. In embodiments, an erythroid cell comprises two targeting agents, which may increase the specificity and/or affinity and/or avidity of the erythroid cell binding to its target, compared to an otherwise similar erythroid cell comprising only one of the targeting agents. The erythroid cell optionally further comprises an exogenous polypeptide with therapeutic activity, e.g., anti-cancer activity. The exogenous polypeptide with therapeutic activity can comprise an enzyme, capture reagent, agonist, or antagonist.

In embodiments, the targeting moiety comprises a receptor or a fragment or variant thereof. In embodiments, the targeting moiety comprises an antibody molecule such as an scFv.

As another example, the targeting agent binds at or near a cancer cell, e.g., solid tumor cell, and the second agent (e.g., second polypeptide) has an anti-cancer function. In some embodiments the site of action is tumor vasculature. In embodiments, the targeting agent binds a marker of neovasculature, e.g. binds an integrin such as avB1, avB3, or avB5, or a4b1 integrins, e.g. a synthetic peptide knottin (Kim et al, JACS 2016, 137(1)) or an endogenous or natural ligand, e.g. echistatin, RGD, EETI2.5F, or VCAM-1, or binds prostate-specific membrane antigen, which is also found abundantly on neovasculature. In some embodiments, the targeting agent binds a cancer cell marker such as CD269 (expressed, e.g., in multiple myeloma cells) or CD123 (expressed, e.g., in ALM cells), CD28 (expressed, e.g., in T cells; CD28 can be bound by CD80/CD86), NY-ESO-1 (expressed, e.g., in ovarian cancer).

The therapeutic agent may have, e.g., an anti-cancer effect, of which there are several strategies. For example the therapeutic agent may be an enzyme, e.g. asparaginase, methionine gamma lyase (MGL), serine dehyrodgenase, or fragment or variant thereof, that degrades metabolites that are selectively required by tumor cells to grow. The therapeutic agent may be an inhibitor of angiogenesis, e.g. an inhibitor of angiopoitin or an inhibitor of VEGF or VEGFR to prevent further growth of blood vessels. The therapeutic agent may be an immunostimulatory molecule to activate T cells, either a cytokine or a T cell activation ligand (see, e.g., Table 1 and Table 2). The therapeutic agent may bind an immune effector cell, e.g. a T cell or an inflammatory macrophage and may capture and bring the effector cell into proximity of the tumor. The therapeutic agent may be a direct mediator of cell killing, e.g. TRAIL or FAS-L or other death ligands, or a toxin. In some embodiments, the therapeutic agent comprises an agonist of a TRAIL receptor, e.g., an agonistic antibody molecule. In embodiments, the therapeutic agent is a pro-apoptotic agent. In embodiments, the therapeutic agent comprises an adjuvant. For any of these therapeutic agents, the net result is a red cell therapeutic that localizes to a tumor site and thus concentrates its anti-tumor effect in a location that increases its efficacy.

Figure 8:
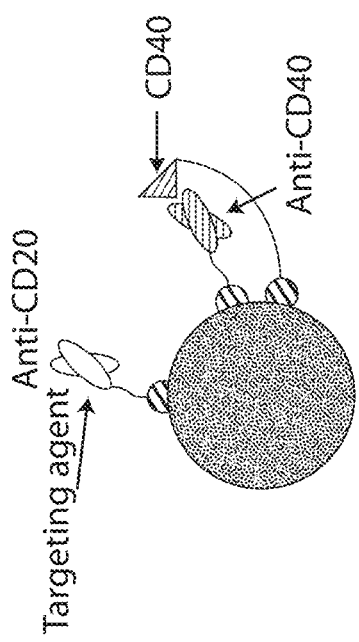
FIG. 8 is a diagram of an erythroid cell comprising a first exogenous polypeptide with therapeutic activity (e.g., an anti-CD40 antibody molecule), a second exogenous polypeptide (e.g., CD40 or a fragment or variant thereof) that inhibits the first exogenous polypeptide, and optionally a third exogenous polypeptide that comprises a targeting agent, e.g., an anti-CD20 antibody molecule.
Figure 10:
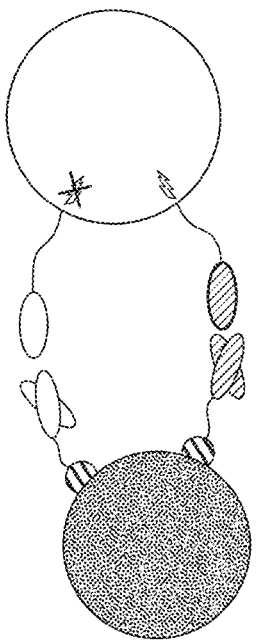
FIG. 10 is a diagram of an erythroid cell comprising an antagonist and/or agonist.

In some embodiments, e.g., for treating a B cell cancer, the first exogenous polypeptide comprises a surface-exposed anti-CD20 antibody molecule that can target the cell to a cancer cell, and the second exogenous polypeptide comprises a surface-exposed anti-CD40 antibody molecule that can inhibit (e.g., kill) the cancer cell. The erythroid cell can further comprise an inhibitor of the anti-CD40 antibody molecule, e.g., as illustrated in FIG. 8.

Figure 11:
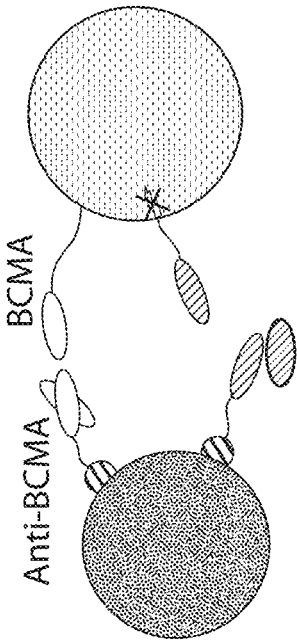
FIG. 11 is a diagram or an erythroid cell comprising a targeting agent (e.g., an anti-CD4 antibody molecule) and an internal payload (e.g., IDO).

The first exogenous polypeptide can comprise a targeting agent and the second exogenous polypeptide can comprise an enzyme (e.g., FIG. 11). For example, in some embodiments, e.g., for treating a cancer, the erythroid cell comprises a first polypeptide comprising a targeting agent that binds a cancer cell and a second polypeptide that inhibits (e.g., kills, induces anergy in, inhibits growth of) the cancer cell. For instance, the targeting agent can comprise an anti-CD4 antibody which binds CD4 on the surface of a T cell, e.g., a cancerous T cell. The second polypeptide can comprise an enzyme which can be surface-exposed or intracellular, e.g., intracellular and not membrane associated. The enzyme may be IDO or a fragment or variant thereof, which depletes tryptophan and can induce anergy in the cancerous T cell, or ADA or a fragment or variant thereof. The enzyme may be a protease.

In embodiments, the target cell is an immune cell, e.g., a T cell, e.g., a helper T cell, and/or a disease cell. The targeting agent may comprise an antibody molecule, e.g., an scFv.

Figure 12:
FIG. 12 is a diagram of an erythroid cell comprising a first exogenous polypeptide comprising a targeting agent and a second exogenous polypeptide comprising an agonist of a target.

The first exogenous polypeptide can comprise a targeting agent and the second exogenous polypeptide can comprise an agonist of a target (see, e.g., FIG. 12). In embodiments, the targeting agent comprises a receptor or fragment or variant thereof, an antibody molecule, a ligand or fragment or variant thereof, a cytokine or fragment or variant thereof. In embodiments, the second exogenous polypeptide comprises an attenuator, an activator, a cell-killing agent, or a cytotoxic molecule (e.g., a small molecule, protein, RNA e.g., antisense RNA, or TLR ligand). In embodiments, the second exogenous polypeptide is intracellular, e.g., not membrane associated, and in some embodiments, the second exogenous polypeptide is surface-exposed.

Figure 13:
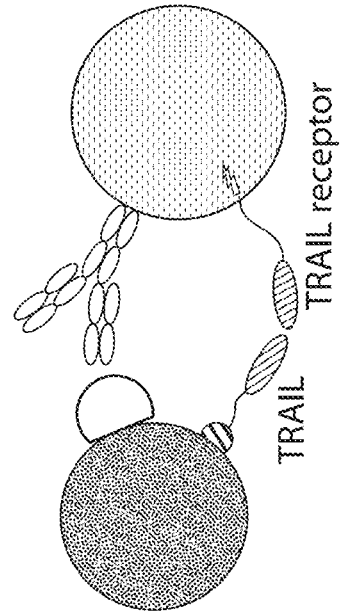
FIG. 13 is a diagram of an erythroid cell comprising a first exogenous polypeptide comprising a targeting agent (e.g., an anti-BCMA antibody molecule) and a second exogenous polypeptide comprising a capture agent.

The erythroid cell can comprise a targeting agent and a capture agent (e.g., FIG. 13). For example, the first exogenous polypeptide can comprise a targeting agent that binds a plasma cell, e.g., an anti-BCMA antibody molecule. In embodiments, the second exogenous polypeptide binds its target in a way that prevents the target from interacting with an endogenous receptor, e.g., binds the target at a moiety that overlaps with the receptor binding site. In embodiments, the targeting moiety binds a receptor at the site of disease. In embodiments, the targeting agent comprises a ligand or a cytokine or fragment or variant thereof, or an antibody molecule, e.g., an scFv. In embodiments, the capture agent comprises a receptor or fragment or variant thereof, or an antibody molecule, e.g., an scFv. In embodiments, the ligand is an unwanted cytokine or chemokine.

Figure 14:
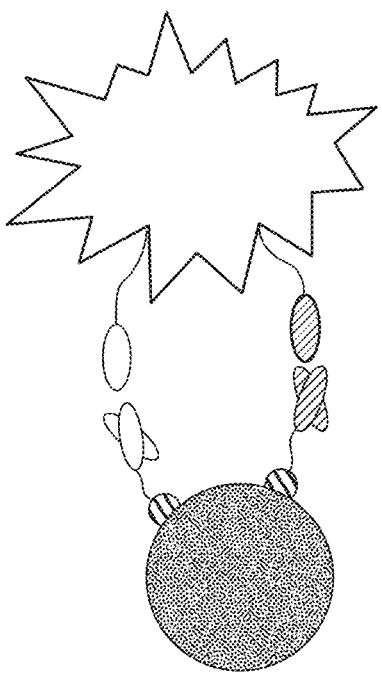
FIG. 14 is a diagram of an erythroid cell comprising a first exogenous polypeptide comprising a targeting agent and a second exogenous polypeptide (e.g., TRAIL) that promotes a given activity, e.g., apoptosis.

A targeting agent can direct an erythroid cell to a particular sub-type of cell. The cell can further comprise a second exogenous polypeptide that promotes a given activity or pathway in the target cell, e.g., can attenuate, activate, or induce cell death. For instance, FIG. 14 depicts an erythroid cell comprising a first exogenous polypeptide that can bind a target cell. The erythroid cell can further comprise a second exogenous polypeptide that inhibits (e.g., kills, or inhibits growth of) the cancer cell. For instance, the second exogenous polypeptide can comprise a cell-killing agent, e.g., a pro-apoptotic agent, e.g., a TRAIL polypeptide that induces apoptosis in the cancer cell. The erythroid cell may also comprise a targeting agent and an attenuator or activator that is surface exposed or intracellular. For example, the cell can comprise a targeting agent and an enzyme such as IDO or ADA or a fragment or variant thereof.

Proximity-Based Configurations

When two or more agents (e.g., polypeptides) have a proximity-based relationship, the two agents function more strongly, e.g., exert a more pronounced effect, when they are in proximity to each other than when they are physically separate. In embodiments, the two agents are in proximity when they are directly binding to each other, when they are part of a complex (e.g., linked by a third agent), when they are present on the same cell membrane, or when they are present on the same subsection of a cell membrane (e.g., within a lipid raft, outside a lipid raft, or bound directly or indirectly to an intracellular structure such as a cytoskeleton component). In some embodiments, first polypeptide binds a first target molecule and the second polypeptide binds a second target molecule, and this binding causes the first target molecule and the second target molecule to move into closer proximity with each other, e.g., to bind each other. In some embodiments, the first and second target molecules are cell surface receptors on a target cells.

An example of a proximity-based configuration is shown in FIG. 4. The erythroid cell of FIG. 4 comprises an optional first exogenous polypeptide (white), a second exogenous polypeptide (light gray), and a third exogenous polypeptide (dark gray). The second and third exogenous polypeptides bind to different epitopes within the same polypeptide chain of a target, e.g., cytokine B. The second and third exogenous polypeptides, which are mounted on the erythrocyte, bind to the target with higher avidity than if the second and third exogenous polypeptides were free polypeptides. As examples, two or more exogenous polypeptides could bind different sites on the same target, wherein the target is a cytokine, an enzyme, or an antibody.

Scaffold Configurations

When two or more agents (e.g., polypeptides) have a scaffold relationship, the agents bring two or more targets together, to increase the likelihood of the targets interacting with each other. In an embodiment the first and second agent are associated with each other (forming a scaffold) at the surface of the RBC, e.g., two complexed polypeptides. In an embodiment, the red blood cell (e.g., reticulocyte) comprises a bispecific antibody molecule, e.g., an antibody molecule that recognizes one or more (e.g., 2) proteins described herein, e.g., in any of Table 1, Table 2, and Table 3.

The targets may comprise, e.g., proteins, cells, small molecules, or any combination thereof. In an embodiment, the first and second targets are proteins. In an embodiment, the first and second targets are cells.

As another example, a RBC brings an immune effector cell (e.g., T cell) and a cancer cell in close proximity with one another to facilitate the killing of the cancer cell by the immune effector cell. Thus, in some embodiments, the first polypeptide binds a cell surface marker of a cancer cell and the second polypeptide binds a cell surface marker of an immune effector cell.

The first and second polypeptides may comprise, e.g., antibody molecules. In some embodiments, the cancer cell marker is selected from CD19 (expressed, e.g., in B cell acute leukemia), EpCAM (expressed, e.g., in CTCs), CD20 (expressed, e.g., in B cell acute leukemia), CD45 (expressed, e.g., in CTCs), EGFR, HER2 (expressed, e.g., in breast cancer cells). In some embodiments, the immune cell marker is CD3.

In some embodiments, the RBC brings an immune effector cell into proximity with another immune cell, e.g., to promote antigen presentation (e.g., when one cell is an antigen presenting cell and the other cell is a T cell), e.g., for a cancer vaccine.

In some embodiments, a RBC expresses an exogenous fusion polypeptide comprising a first antibody molecule domain and a second antibody molecule domain, wherein the exogenous polypeptide functions as a bispecific antibody, e.g., wherein the first antibody molecule domain binds a first target on a first cell and the second antibody molecule domain binds a second target on a second cell, e.g., a different cell type.

Multimer Configurations

When two or more agents (e.g., polypeptides) have a multimer configuration, the agents combine with each other, e.g., bind each other, to form a complex that has a function or activity on a target. In an embodiment, the agents are subunits of a cell surface complex, e.g., MHCI, and a function is to bind a peptide. In an embodiment, the agents are subunits of MHCII, and a function is to bind a peptide.

In an embodiment, the agents are subunits of a cell surface molecule, e.g., MHCI and a peptide, e.g., a peptide loaded on the MHCI molecule, and a function is to present the peptide. In an embodiment, the agents are subunits of a MHCII and a peptide, e.g., a peptide loaded on the MHCII molecule, and a function is to present the peptide. In one embodiment, the complex is a functional MHC I, the agents are MHC I (alpha chain 1-3) and beta-2 microglobulin, or fragments or variants thereof. In one embodiment the complex is MHC II and the agents are MHC II alpha chain and MHC II beta chain, or fragments or variants thereof. In some embodiments, the MHC molecule comprises human MHC class I or II, e.g., MHC II alpha subunit and MHC II beta subunit or a fusion molecule comprising both subunits or antigen-presenting fragments thereof. A RBC with these two polypeptides is used, in some embodiments, for immune induction or antigen presentation. In some embodiments, the RBC comprises a single protein that is a fusion between an MHC molecule and an antigen, e.g., a single-chain peptide-MHC construct. In some embodiments, a non-membrane tethered component of the complex, e.g. the peptide, or the beta-2 microglobulin, is assembled with another agent within the cell prior to trafficking to the surface, is secreted by the cell then captured on the surface by the membrane-tethered component of the multimer, or is added in a purified form to an engineered red blood cell.

The antigen is, in some embodiments, a cancer antigen, e.g., for a cancer vaccine. In some embodiments, the antigen is about 8, 9, 10, 11, 12, 13, 14, 15, 16, 17, 18, 19, 20, 25, 30, or 35 amino acids in length.

In some embodiments the complex comprises multiple subdomains derived from different polypeptide chains, all of which must be expressed in order for the complex to be active.

Compensatory Configurations

When two or more agents (e.g., polypeptides) have a compensatory relationship, a first agent reduces an undesirable characteristic of a second agent. For example, in some embodiments, the second agent has a given level of immunogenicity, and the first agent reduces the immunogenicity, e.g., by negatively signaling immune cells (see Table 3), or by shielding an antigenic epitope of the second agent. In some embodiments, the second agent has a given half-life, and the first agent increases the half-life of the second agent. For example, the first agent can comprise a chaperone or fragment or variant thereof.

An enucleated erythroid cell can co-express a therapeutic protein and its inhibitor (e.g., FIG. 8). The inhibitor can be released (e.g., cease binding the therapeutic but remain on the surface of the cell) in at the desired location in the body, to activate the therapeutic protein.

For instance, in some embodiments, the erythroid cell comprises a first exogenous polypeptide with therapeutic activity (e.g., an anti-CD40 antibody molecule), a second exogenous polypeptide (e.g., CD40 or a fragment or variant thereof) that inhibits the first exogenous polypeptide. The second polypeptide (e.g., CD40) may inhibit activity of the first exogenous polypeptide (e.g., anti-CD40) until the erythroid cell is at a desired location, e.g., a cancer cell, e.g., limiting off-target effects. The second exogenous polypeptide (e.g., CD40 or a variant thereof) may comprise a variant of the target (e.g., endogenous CD40) that the first exogenous polypeptide (e.g., anti-CD40) binds. For instance, the variant can be a weakly-binding variant that is competed away in the presence of the target. In embodiments, the Kd of the first exogenous polypeptide for the second exogenous polypeptide is at least 2, 3, 5, 10, 20, 50, or 100-fold greater than the Kd of the first exogenous polypeptide for its target. The erythroid cell optionally comprises a third exogenous polypeptide that comprises a targeting agent, e.g., an anti-CD20 antibody molecule.

In some embodiments, the enucleated erythroid cell comprises a prodrug (e.g., pro-insulin) that becomes a drug (e.g., insulin) at a desired site in a subject.

Enucleated Red Blood Cells Comprising Three or More Agents (e.g., Polypeptides)

In embodiments, a red blood cell (e.g., reticulocyte) described herein comprises three or more, e.g., at least 4, 5, 10, 20, 50, 100, 200, 500, or 1000 agents. In embodiments, a population of red blood cells described herein comprises three or more, e.g., at least 4, 5, 10, 20, 50, 100, 200, 500, 1000, 2000, or 5000 agents, e.g., wherein different RBCs in the population comprise different agents or wherein different RBCs in the population comprise different pluralities of agents. In embodiments, two or more (e.g., all) of the agents in the RBC or population or RBCs have agent-additive, agent-synergistic, multiplicative, independent function, localization-based, proximity-dependent, scaffold-based, multimer-based, or compensatory activity.

In embodiments, the RBC is produced by contacting a RBC progenitor cell with a plurality of mRNAs encoding the agents.

Eukaryotic Display Screening.

In an embodiment, a combinatorial, high-diversity pool of cells is produced, e.g., for use in an in vitro or in vivo binding assay. A combinatorial, high-diversity nucleic acid library encoding cell-surface proteins can be created. Such a library could, e.g., consist of entirely variable sequences, or comprise a fixed sequence fused to a highly variable, combinatorial sequence. These can be introduced into red blood cell progenitors as a mixture or individually, using methods such as electroporation, transfection or viral transduction. In one embodiment, the cells are subsequently grown in differentiation media until the desired level of maturity. In one embodiment, the cells are used for a highly multiplexed in-vitro assay. Cells are incubated with a biological sample in a microtiter plate. Wells are washed using a cell-compatible buffer, with a desired level of stringency. The remaining cells are isolated and analyzed for the enrichment of specific sequences. In one embodiment, the analysis is performed at the protein level, e.g., using mass spectrometry, to identify the amino acid motifs that are enriched in the bound population. In an embodiment, the analysis is performed at the nucleic acid level (RNA or DNA) to identify the nucleic acid sequences identifying the corresponding amino-acid motif enriched in the bound population. In an embodiment, the high-diversity cell population is injected into an animal model (either healthy or diseased). In one embodiment the cells are fluorescently labeled to visualize their in vivo distribution or localization. Various tissues of the animal could then be collected and analyzed for the relative enrichment of specific amino-acid motifs or nucleic acid sequences identifying the corresponding amino-acid motif.

Expression Optimization.

A large number of variants can be simultaneously transfected into individual cells to assess their relative transcription or translation ability. In embodiments, a library of protein coding sequences are designed and synthesized with a diversity of 5' untranslated regions, 3' untranslated regions, codon representations, amino acid changes, and other sequence differences. This library would be introduced into red blood cell progenitors as a mixture or individually, using methods such as electroporation, transfection or viral transduction. In one embodiment, the cells are subsequently grown in differentiation media until the desired level of maturity.

Physical Characteristics of Enucleated Red Blood Cells

In some embodiments, the RBCs (e.g., reticulocytes) described herein have one or more (e.g., 2, 3, 4, or more) physical characteristics described herein, e.g., osmotic fragility, cell size, hemoglobin concentration, or phosphatidylserine content. While not wishing to be bound by theory, in some embodiments an enucleated RBC that expresses an exogenous protein has physical characteristics that resemble a wild-type, untreated RBC. In contrast, a hypotonically loaded RBC sometimes displays aberrant physical characteristics such as increased osmotic fragility, altered cell size, reduced hemoglobin concentration, or increased phosphatidylserine levels on the outer leaflet of the cell membrane.

In some embodiments, the enucleated RBC comprises an exogenous protein that was encoded by an exogenous nucleic acid that was not retained by the cell, has not been purified, or has not existed fully outside an RBC. In some embodiments, the RBC is in a composition that lacks a stabilizer.

Osmotic Fragility

In some embodiments, the enucleated red blood cell exhibits substantially the same osmotic membrane fragility as an isolated, uncultured erythroid cell that does not comprise an exogenous polypeptide. In some embodiments, the population of enucleated red blood cells has an osmotic fragility of less than 50% cell lysis at 0.3%, 0.35%, 0.4%, 0.45%, or 0.5% NaCl. Osmotic fragility can be assayed using the method of Example 59 of WO2015/073587.

Cell Size

In some embodiments, the enucleated RBC has approximately the diameter or volume as a wild-type, untreated RBC.

In some embodiments, the population of RBC has an average diameter of about 4, 5, 6, 7, or 8 microns, and optionally the standard deviation of the population is less than 1, 2, or 3 microns. In some embodiments, the one or more RBC has a diameter of about 4-8, 5-7, or about 6 microns. In some embodiments, the diameter of the RBC is less than about 1 micron, larger than about 20 microns, between about 1 micron and about 20 microns, between about 2 microns and about 20 microns, between about 3 microns and about 20 microns, between about 4 microns and about 20 microns, between about 5 microns and about 20 microns, between about 6 microns and about 20 microns, between about 5 microns and about 15 microns or between about 10 microns and about 30 microns. Cell diameter is measured, in some embodiments, using an Advia 120 hematology system.

In some embodiment the volume of the mean corpuscular volume of the RBCs is greater than 10 fL, 20 fL, 30 fL, 40 fL, 50 fL, 60 fL, 70 fL, 80 fL, 90 fL, 100 fL, 110 fL, 120 fL, 130 fL, 140 fL, 150 fL, or greater than 150 fL. In one embodiment the mean corpuscular volume of the RBCs is less than 30 fL, 40 fL, 50 fL, 60 fL, 70 fL, 80 fL, 90 fL, 100 fL, 110 fL, 120 fL, 130 fL, 140 fL, 150 fL, 160 fL, 170 fL, 180 fL, 190 fL, 200 fL, or less than 200 fL. In one embodiment the mean corpuscular volume of the RBCs is between 80-100, 100-200, 200-300, 300-400, or 400-500 femtoliters (fL). In some embodiments, a population of RBCs has a mean corpuscular volume set out in this paragraph and the standard deviation of the population is less than 50, 40, 30, 20, 10, 5, or 2 fL. The mean corpuscular volume is measured, in some embodiments, using a hematological analysis instrument, e.g., a Coulter counter.

Hemoglobin Concentration

In some embodiments, the enucleated RBC has a hemoglobin content similar to a wild-type, untreated RBC. In some embodiments, the RBCs comprise greater than 1%, 2%, 3%, 4%, 5%, 6%, 7%, 8%, 9% or greater than 10% fetal hemoglobin. In some embodiments, the RBCs comprise at least about 20, 22, 24, 26, 28, or 30 pg, and optionally up to about 30 pg, of total hemoglobin. Hemoglobin levels are determined, in some embodiments, using the Drabkin's reagent method of Example 33 of WO2015/073587.

Phosphatidylserine Content

In some embodiments, the enucleated RBC has approximately the same phosphatidylserine content on the outer leaflet of its cell membrane as a wild-type, untreated RBC. Phosphatidylserine is predominantly on the inner leaflet of the cell membrane of wild-type, untreated RBCs, and hypotonic loading can cause the phosphatidylserine to distribute to the outer leaflet where it can trigger an immune response. In some embodiments, the population of RBC comprises less than about 30, 25, 20, 15, 10, 9, 8, 6, 5, 4, 3, 2, or 1% of cells that are positive for Annexin V staining. Phosphatidylserine exposure is assessed, in some embodiments, by staining for Annexin-V-FITC, which binds preferentially to PS, and measuring FITC fluorescence by flow cytometry, e.g., using the method of Example 54 of WO2015/073587.

Other Characteristics

In some embodiments, the population of RBC comprises at least about 50%, 60%, 70%, 80%, 90%, or 95% (and optionally up to 90 or 100%) of cells that are positive for GPA. The presence of GPA is detected, in some embodiments, using FACS.

In some embodiments, the RBCs have a half-life of at least 30, 45, or 90 days in a subject.

In some embodiments, a population of cells comprising RBCs comprises less than about 10, 5, 4, 3, 2, or 1% echinocytes.

In some embodiments, an RBC is enucleated, e.g., a population of cells comprising RBCs used as a therapeutic preparation described herein is greater than 50%, 60%, 70%, 80%, 90% enucleated. In some embodiments, a cell, e.g., an RBC, contains a nucleus that is non-functional, e.g., has been inactivated.

Methods of Manufacturing Enucleated Red Blood Cells

Methods of manufacturing enucleated red blood cells (e.g., reticulocytes) comprising (e.g., expressing) exogenous agent (e.g., polypeptides) are described, e.g., in WO2015/073587 and WO2015/153102, each of which is incorporated by reference in its entirety.

In some embodiments, hematopoietic progenitor cells, e.g., CD34+ hematopoietic progenitor cells, are contacted with a nucleic acid or nucleic acids encoding one or more exogenous polypeptides, and the cells are allowed to expand and differentiate in culture.

In some embodiments, the two or more polypeptides are encoded in a single nucleic acid, e.g. a single vector. In embodiments, the single vector has a separate promoter for each gene, has two proteins that are initially transcribed into a single polypeptide having a protease cleavage site in the middle, so that subsequent proteolytic processing yields two proteins, or any other suitable configuration. In some embodiments, the two or more polypeptides are encoded in two or more nucleic acids, e.g., each vector encodes one of the polypeptides.

The nucleic acid may be, e.g., DNA or RNA. A number of viruses may be used as gene transfer vehicles including retroviruses, Moloney murine leukemia virus (MMLV), adenovirus, adeno-associated virus (AAV), herpes simplex virus (HSV), lentiviruses such as human immunodeficiency virus 1 (HIV 1), and spumaviruses such as foamy viruses, for example.

In some embodiments, the cells are produced using sortagging, e.g., as described in WO2014/183071 or WO2014/183066, each of which is incorporated by reference in its entirety.

In some embodiments, the RBCs are expanded at least 1000, 2000, 5000, 10,000, 20,000, 50,000, or 100,000 fold (and optionally up to 100,000, 200,000, or 500,000 fold). Number of cells is measured, in some embodiments, using an automated cell counter.

In some embodiments, the population of RBC comprises at least 30, 35, 40, 45, 50, 55, 60, 65, 70, 75, 80, 85, 90, 95, or 98% (and optionally up to about 80, 90, or 100%) enucleated RBC. In some embodiments, the population of RBC contains less than 1% live enucleated cells, e.g., contains no detectable live enucleated cells. Enucleation is measured, in some embodiments, by FACS using a nuclear stain. In some embodiments, at least 30, 35, 40, 45, 50, 55, 60, 65, 70, 75, or 80% (and optionally up to about 70, 80, 90, or 100%) of RBC in the population comprise one or more (e.g., 2, 3, 4 or more) of the exogenous polypeptides.

Expression of the polypeptides is measured, in some embodiments, by FACS using labeled antibodies against the polypeptides. In some embodiments, at least 30, 35, 40, 45, 50, 55, 60, 65, 70, 75, or 80% (and optionally up to about 70, 80, 90, or 100%) of RBC in the population are enucleated and comprise one or more (e.g., 2, 3, 4, or more) of the exogenous polypeptides. In some embodiments, the population of RBC comprises about $1\times10^9$-$2\times10^9$, $2\times10^9$-$5\times10^9$, $5\times10^9$-$1\times10^{10}$, $1\times10^{10}$-$2\times10^{10}$, $2\times10^{10}$-$5\times10^{10}$, $5\times10^{10}$-$1\times10^{11}$, $1\times10^{11}$-$2\times10^{11}$, $2\times10^{11}$-$5\times10^{11}$, $5\times10^{11}$-$1\times10^{12}$, $1\times10^{12}$-$2\times10^{12}$, $2\times10^{12}$-$5\times10^{12}$, or $5\times10^{12}$-$1\times10^{13}$ cells.

Physically Proximal, Synergistic Agents

In some aspects, the present disclosure provides a composition comprising a first agent and a second agent in physical proximity to each other. In some embodiments, agents act synergistically when they are in physical proximity to each other but not when they are separate. In some embodiments, the first and second agent are covalently linked, e.g., are part of a fusion protein or are chemically conjugated together. In some embodiments, the first and second agent are non-covalently linked, e.g., are bound directly to each other or to a scaffold. In some embodiments, the first and second agents are part of (e.g., linked to) a nanoparticle (e.g., 1-100, 100-2,500, or 2,500-10,000 nm in diameter) liposome, vesicle, bead, polymer, implant, or polypeptide complex.

In some embodiments, the composition comprises at least 3, 4, 5, 6, 7, 8, 9, or 10 different agents that are in physical proximity to each other (e.g., covalently or noncovalently linked).

In some embodiments, the composition comprises one or more (e.g., 2, 3, 4, 5, or more) agents described herein, e.g., exogenous polypeptides described herein, e.g., polypeptides of any of Table 1, Table 2, or Table 3, or a fragment or variant thereof, or an antibody molecule thereto. In some embodiments, one or more (e.g., 2, 3, or more) of the exogenous polypeptides comprise cytokines, interleukins, cytokine receptors, Fc-binding molecules, T-cell activating ligands, T cell receptors, immune inhibitory molecules, costimulatory molecule, MHC molecules, APC-binding molecule, toxin, targeting agent, anti-cancer agent, cancer cell marker, agent that binds a cancer cell marker, or TRAIL receptor ligands.

In some embodiments, one or more (e.g., 2, 3, or more) of the exogenous polypeptides comprise TRAIL receptor ligands, e.g., a sequence of any of SEQ ID NOS: 1-5 herein, or a sequence with at least 70%, 80%, 85%, 90%, 95%, 96%, 97%, 98%, or 99% identity thereto, or an antibody molecule that binds a TRAIL receptor. In some embodiments, the first agent binds to a first TRAIL receptor, e.g., TRAIL-RI, and the second agent binds to a second TRAIL receptor, e.g., TRAIL-RII. In embodiments, the two TRAIL receptor ligands in proximity provide a synergistic degree of apoptosis in a target cell, compared to either TRAIL receptor ligand alone. Example 1 herein demonstrates a synergistic activity when cancer cells are treated with a composition comprising two TRAIL receptor ligands in close proximity (e.g., on the surface of an enucleated red blood cell).

Engineered Red Blood Cells Comprising One or More Agents

In some aspects, the present disclosure provides an engineered red blood cell (e.g., reticulocyte) comprising an exogenous agent. More specifically, in some aspects, the present disclosure provides an enucleated red blood cell (e.g., reticulocyte) comprising an exogenous polypeptide. The red blood cell optionally further comprises a second, different, exogenous polypeptide.

In some embodiments, the exogenous polypeptide (e.g., an exogenous polypeptide comprised by a red blood cell that optionally further comprises a second exogenous polypeptide) is an exogenous polypeptide described herein. In embodiments, the polypeptide is selected from any of Table 1, Table 2, or Table 3, or a fragment or variant thereof, or an antibody molecule thereto.

In some embodiments, the exogenous polypeptide (e.g., an exogenous polypeptide comprised by a red blood cell that optionally further comprises a second exogenous polypeptide) comprises a stimulatory ligand, e.g., CD80, CD86, 41BBL, or any combination thereof, e.g., for the treatment of a cancer. In some embodiments, the exogenous polypeptide comprises a cancer cell antigen such as CD269, e.g., for the treatment of a cancer such as multiple myeloma.

In some embodiments, the exogenous polypeptide (e.g., an exogenous polypeptide comprised by a red blood cell that optionally further comprises a second exogenous polypeptide) inhibits an immune checkpoint molecule. In embodiments, the exogenous polypeptide is situated at the surface of the engineered red blood cell (e.g., comprises a transmembrane portion and a surface-exposed portion) and binds an immune checkpoint molecule. In embodiments, the immune checkpoint molecule is PD-1 or PD-L1. In embodiments, the immune checkpoint molecule is PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 or TGF beta.

In some embodiments, the exogenous polypeptide (e.g., an exogenous polypeptide comprised by a red blood cell that optionally further comprises a second exogenous polypeptide) inhibits an immune checkpoint molecule. In one embodiment, the inhibitor of the immune checkpoint molecule is an inhibitory antibody molecule (e.g., an antibody such as a monospecific antibody, monoclonal antibody, or a single chain antibody). The antibody molecule may be, e.g., humanized or fully human. In other embodiments, the inhibitor of the immune checkpoint molecule is a fusion protein, e.g., an Fc-receptor fusion protein. In some embodiments, the inhibitor of the immune checkpoint molecule is an agent, such as an antibody molecule, that interacts with an immune checkpoint protein. In some embodiments, the inhibitor of the immune checkpoint molecule is an agent, such as an antibody molecule, that interacts with the ligand of an immune checkpoint receptor. In one embodiment, the inhibitor of the immune checkpoint molecule is an inhibitor (e.g., an inhibitory antibody or small molecule inhibitor) of CTLA-4 (e.g., an anti-CTLA4 antibody such as ipilimumab/Yervoy or tremelimumab). In one embodiment, the inhibitor of the immune checkpoint molecule is an inhibitor (e.g., an inhibitory antibody or small molecule inhibitor) of PD-1 (e.g., nivolumab/Opdivo®; pembrolizumab/Keytruda®; pidilizumab/CT-011). In one embodiment, the inhibitor of the immune checkpoint molecule is an inhibitor (e.g., an inhibitory antibody or small molecule inhibitor) of PD-L1 (e.g., MPDL3280A/RG7446; MEDI4736; MSB0010718C; BMS 936559). In one embodiment, the inhibitor of the immune checkpoint molecule is an inhibitor (e.g., an inhibitory antibody or Fc fusion or small molecule inhibitor) of PDL2 (e.g., a PDL2/Ig fusion protein such as AMP 224). In one embodiment, the inhibitor of the immune checkpoint molecule is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. Inhibitors of immune checkpoint molecules can be broken down into at least 4 major categories: i) agents such as antibody molecules that block an inhibitory pathway directly on T cells or natural killer (NK) cells (e.g., PD-1 targeting antibodies such as nivolumab and pembrolizumab, antibodies targeting TIM-3, and antibodies targeting LAG-3, 2B4, CD160, A2aR, BTLA, CGEN-15049, or KIR), ii) agents such as antibodies that activate stimulatory pathways directly on T cells or NK cells (e.g., antibodies targeting OX40, GITR, or 4-1BB), iii) agents such as antibody molecules that block a suppressive pathway on immune cells or rely on antibody-dependent cellular cytotoxicity to deplete suppressive populations of immune cells (e.g., CTLA-4 targeting antibodies such as ipilimumab, antibodies targeting VISTA, and antibodies targeting PD-L2, Gr1, or Ly6G), and iv) agents such as antibody molecules that block a suppressive pathway directly on cancer cells or that rely on antibody-dependent cellular cytotoxicity to enhance cytotoxicity to cancer cells (e.g., rituximab, antibodies targeting PD-L1, and antibodies targeting B7-H3, B7-H4, Gal-9, or MUC1). Such agents described herein can be designed and produced, e.g., by conventional methods known in the art (e.g., Templeton, Gene and Cell Therapy, 2015; Green and Sambrook, Molecular Cloning, 2012).

Vehicles for Polypeptides Described Herein

While in many embodiments herein, the one or more (e.g., two or more) exogenous polypeptides are situated on or in a red blood cell, it is understood that any exogenous polypeptide or combination of exogenous polypeptides described herein can also be situated on or in another vehicle. The vehicle can comprise, e.g., a cell, an erythroid cell, a corpuscle, a nanoparticle, a micelle, a liposome, or an exosome. For instance, in some aspects, the present disclosure provides a vehicle (e.g., a cell, an erythroid cell, a corpuscle, a nanoparticle, a micelle, a liposome, or an exosome) comprising, e.g., on its surface, one or more agents described herein. In some embodiments, the one or more agent comprises a polypeptide that binds PD-1 (e.g., an antibody molecule that binds PD-1 or an agonist of PD-1 such as PD-L1), a polypeptide that binds PD-L1 (e.g., an antibody molecule that binds PD-L1), a polypeptide that binds CD20 (e.g., an antibody molecule that binds CD20), or a polypeptide that binds a TRAIL receptor (e.g., an agonist of a TRAIL receptor). In some embodiments, the one or more agents comprise an agent selected a polypeptide of any of Table 1, Table 2, or Table 3, or a fragment or variant thereof, or an agonist or antagonist thereof, or an antibody molecule thereto. In some embodiments, the vehicle comprises two or more agents described herein, e.g., any pair of agents described herein.

In some embodiments, the vehicle comprises an erythroid cell. In embodiments, the erythroid cell is a nucleated red blood cell, red blood cell precursor, or enucleated red blood cell. In embodiments, the erythroid cell is a cord blood stem cell, a CD34+ cell, a hematopoietic stem cell (HSC), a spleen colony forming (CFU-S) cell, a common myeloid progenitor (CMP) cell, a blastocyte colony-forming cell, a burst forming unit-erythroid (BFU-E), a megakaryocyte-erythroid progenitor (MEP) cell, an erythroid colony-forming unit (CFU-E), a reticulocyte, an erythrocyte, an induced pluripotent stem cell (iPSC), a mesenchymal stem cell (MSC), a polychromatic normoblast, an orthochromatic normoblast, or a combination thereof. In some embodiments, the erythroid cells are immortal or immortalized cells.

Cells Encapsulated in a Membrane

In some embodiments, enucleated erythroid cells or other vehicles described herein are encapsulated in a membrane, e.g., semi-permeable membrane. In embodiments, the membrane comprises a polysaccharide, e.g., an anionic polysaccharide alginate. In embodiments, the semipermeable membrane does not allow cells to pass through, but allows passage of small molecules or macromolecules, e.g., metabolites, proteins, or DNA. In embodiments, the membrane is one described in Lienert et al., "Synthetic biology in mammalian cells: next generation research tools and therapeutics" Nature Reviews Molecular Cell Biology 15, 95-107 (2014), incorporated herein by reference in its entirety. While not wishing to be bound by theory, in some embodiments, the membrane shields the cells from the immune system and/or keeps a plurality of cells in proximity, facilitating interaction with each other or each other's products.

Methods of Treatment with Compositions Herein, e.g., Enucleated Red Blood Cells

Methods of administering enucleated red blood cells (e.g., reticulocytes) comprising (e.g., expressing) exogenous agent (e.g., polypeptides) are described, e.g., in WO2015/073587 and WO2015/153102, each of which is incorporated by reference in its entirety.

In embodiments, the enucleated red blood cells described herein are administered to a subject, e.g., a mammal, e.g., a human. Exemplary mammals that can be treated include without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like). The methods described herein are applicable to both human therapy and veterinary applications.

In some embodiments, the RBCs are administered to a patient every 1, 2, 3, 4, 5, or 6 months.

In some embodiments, a dose of RBC comprises about $1\times10^9$-$2\times10^9$, $2\times10^9$-$5\times10^9$, $5\times10^9$-$1\times10^{10}$, $1\times10^{10}$-$2\times10^{10}$, $2\times10^{10}$-$5\times10^{10}$, $5\times10^{10}$-$1\times10^{11}$, $1\times10^{11}$-$2\times10^{11}$, $2\times10^{11}$-$5\times10^{11}$, $5\times10^{11}$-$1\times10^{12}$, $1\times10^{12}$-$2\times10^{12}$, $2\times10^{12}$-$5\times10^{12}$, or $5\times10^{12}$-$1\times10^{13}$ cells.

In some embodiments, the RBCs are administered to a patient in a dosing regimen (dose and periodicity of administration) sufficient to maintain function of the administered RBCs in the bloodstream of the patient over a period of 2 weeks to a year, e.g., one month to one year or longer, e.g., at least 2 weeks, 4 weeks, 6 weeks, 8 weeks, 3 months, 6 months, a year, 2 years.

In some aspects, the present disclosure provides a method of treating a disease or condition described herein, comprising administering to a subject in need thereof a composition described herein, e.g., an enucleated red blood cell (e.g., reticulocyte) described herein. In some embodiments, the disease or condition is a cancer. In some aspects, the disclosure provides a use of an erythroid cell, e.g., red blood cell, described herein for treating a disease or condition described herein, e.g., a cancer. In some aspects, the disclosure provides a use of an erythroid cell, e.g., red blood cell described herein for manufacture of a medicament for treating a disease or condition described herein, e.g., a cancer.

Types of cancer include acute lymphoblastic leukaemia (ALL), acute myeloid leukaemia (AML), anal cancer, bile duct cancer, bladder cancer, bone cancer, bowel cancer, brain tumours, breast cancer, cancer of unknown primary, cancer spread to bone, cancer spread to brain, cancer spread to liver, cancer spread to lung, carcinoid, cervical cancer, choriocarcinoma, chronic lymphocytic leukaemia (CLL), chronic myeloid leukaemia (CML), colon cancer, colorectal cancer, endometrial cancer, eye cancer, gallbladder cancer, gastric cancer, gestational trophoblastic tumours (GTT), hairy cell leukaemia, head and neck cancer, Hodgkin lymphoma, kidney cancer, laryngeal cancer, leukaemia, liver cancer, lung cancer, NSCLC, lymphoma, melanoma skin cancer, mesothelioma, men's cancer, molar pregnancy, mouth and oropharyngeal cancer, myeloma, nasal and sinus cancers, nasopharyngeal cancer, non-Hodgkin lymphoma (NHL), oesophageal cancer, ovarian cancer, pancreatic cancer, penile cancer, prostate cancer, rare cancers, rectal cancer, salivary gland cancer, secondary cancers, skin cancer (non-melanoma), soft tissue sarcoma, stomach cancer, testicular cancer, thyroid cancer, unknown primary cancer, uterine cancer, vaginal cancer, and vulval cancer.

Additional Tables

TABLE 4

Exemplary modifiers, e.g., proteases

| Modifier | Exemplary target |
|---|---|
| Proteases | |
| IdeS | IgG |
| IdeZ (an immunoglobulin-degrading enzyme from Streptococcus equi subspecies zooepidemicus) | IgG |
| IgA protease | IgG |
| Papain | IgG |
| ADAM17/TACE | TNF-alpha |

TABLE 4-continued

| Exemplary modifiers, e.g., proteases | |
|---|---|
| Modifier | Exemplary target |
| mesotrypsin | Peptides comprising linkages involving the carboxyl group of lysine or arginine |
| Lysozyme | peptidoglycan |
| Endolysin | peptidoglycan |
| Endoproteinase, e.g., LysC (can cleave proteins on C-terminal side of lysine residues) | Protein having a Lys-Xaa motif |
| Metalloendopeptidase, e.g., LysN (can cleave proteins on amino side of lysine residues) | Protein having an Xaa-Lys motif |
| Elastase, e.g., Pseudomonas elastase (PaE) | C3 |
| alkaline protease (PaAP) | C3 |
| 56 kDa protease from Serratia marcescens | C5a, C1-INH, alpha 2-antiplasmin, antithrombin III |
| C5a peptidase, e.g., Streptocoocal C5a peptidase, ScpA, ScpB, SCPA | C5a |
| Plasmin | IgG, C3b, iC3b |
| cysteine protease, e.g., Streptococcal pyrogenic exotoxin B (SpeB) | IgG, cytokines, extracellular matrix proteins |
| PrtH (e.g., from Porphyromonas) | IgG or C3 |
| Staphylokinase | plasminogen, IgG, C3b |
| Matrix metalloproteinases (e.g., MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP26, MMP27, MMP28) | ECM proteins, e.g., collagen, gelatin, fibronectin, laminin, aggrecan, elastin, fibrin |
| Other modifiers | |
| Protein disulfide isomerases | Proteins comprising two cysteine residues |
| Glycosyltransferases, e.g., α-glucan-branching glycosyltransferase, enzymatic branching factor, branching glycosyltransferase, enzyme Q, glucosan transglycosylase, glycogen branching enzyme, amylose isomerase, plant branching enzyme, α-1,4-glucan:α-1,4-glucan-6-, glycosyltransferase, starch branching enzyme, UDP-N-acetyl-D-galactosamine, polypeptide, N-acetylgalactosaminyltransferase, GDP-fucose protein O-fucosyltransferase 2, O-GlcNAc transferase | Protein comprising tyrosine, serine, threonine, or asparagine glycosylation site |
| Acetyltransferases or deacetylases, e.g., nucleosome-histone acetyltransferase, histone acetokinase, histone acetylase, histone transacetylase, histone deacetylase | histone |
| Acyltransferases | Protein comprising an acyl group |
| Phosphatases, e.g., protein-tyrosine-phosphatase, phosphotyrosine phosphatase, phosphoprotein phosphatase (phosphotyrosine), phosphotyrosine histone phosphatase, protein phosphotyrosine phosphatase, tyrosylprotein phosphatase, phosphotyrosine protein phosphatase, phosphotyrosylprotein phosphatase, tyrosine O-phosphate phosphatase, PPT-phosphatase, PTPase, [phosphotyrosine]protein phosphatase, PTP-phosphatase | phosphoprotein |
| Kinases, e.g., non-specific serine/threonine protein kinase, Fas-activated serine/threonine kinase, Goodpasture antigen-binding protein kinase, IκB kinase, cAMP-dependent protein kinase, cGMP-dependent protein kinase, protein kinase C, polo kinase, cyclin-dependent kinase, mitogen-activated protein kinase, mitogen-activated protein kinase kinase kinase, receptor protein serine/threonine kinase, dual-specificity kinase | Protein comprising a serine or threonine phosphorylation site |
| Gamma-carboxylases | Protein comprising glutamic acid |
| Methyltransferases | Protein comprising a lysine methylation site; DNA; RNA |
| Complement-factor inactivating moiety, e.g., complement control protein, Factor H or Factor I | Complement factor, e.g., C1, C2a, C4b, C3, C3a, C3b, C5, C5a, C5b, C6, C7, C8, or C9 |

EXAMPLES

Example 1. Agent-Synergistic Activity of eRBC Expressing Two Different TRAIL Receptor Ligands on the Surface The genes for TRAIL receptor agonists DR4.2 (SEQ ID 2) and DR5.2 (SEQ ID 5) were synthesized. The genes were cloned into a lentivirus vector (SBI) upstream of the gene for human glycophorin A and separated by a sequence encoding a 12-amino acid Gly-Ser (GGGSGGGSGGGS (SEQ ID NO: 19)) flexible linker and an HA epitope tag (YPYDVPDY (SEQ ID NO: 20)).

Human CD34+ cells derived from mobilized peripheral blood cells from normal human donors were purchased frozen from AllCells Inc. Cells were thawed in PBS with 1% FBS. Cells were then cultured in StemSpan SFEM media with StemSpan CC 100 Cytokine Mix at a density of 1E5 cells/mL. Media was swapped to differentiation media on day 5.

Virus production protocol was conducted as follows. Briefly, HEK293T cells were seeded 24 hours before transfection. Cells were transfected with lentivector containing the construct along with packaging plasmids. A media swap was performed 24 hours after transfection and viruses were harvested 72 hours after transfection. On day 6 after thaw, cells were transduced with equal volumes of each virus in a 1:1 cell volume to virus volume ratio, and spinoculated at 845×g for 1.5 hours with 5-10 g/ml of polybrene.

Transduced cells were differentiated in defined media to erythroid lineage cells and to mature enucleated reticulocytes following the method of Hu et al., Blood 18 Apr. 2013 Vol 121, 16. In brief, the cell culture procedure was comprised of 3 phases. Composition of the base culture medium was Iscove's Modified Dulbecco's Medium, 2% human peripheral blood plasma, 3% human AB serum, 200 mg/mL Holohuman transferrin, 3 IU/mL heparin, and 10 mg/mL insulin. In the first phase (day 0 to day 6), CD341 cells at a concentration of $10^5$/mL were cultured in the presence of 10 ng/mL stem cell factor, 1 ng/mL IL-3, and 3 IU/mL erythropoietin. In the second phase (day 7 to day 11), IL-3 was omitted from the culture medium. In the third phase that lasted until day 21, the cell concentration was adjusted to $10^6$/mL on day 11 and to $5 \times 10^6$/mL on day 15, respectively. The medium for this phase was the base medium plus 3 IU/mL erythropoietin, and the concentration of transferrin was adjusted to 1 mg/mL.

Expression of the transgenes was monitored by labeling with soluble TRAIL R1 and TRAIL R2 (purchased from Sigma-Aldrich Inc.) that had been chemically conjugated to complementary fluorescent dyes Fluorescein and DyLight 650 and staining by flow cytometry. Expression levels of both ligands DR4.2 and DR5.2 were verified through flow cytometry.

A tumor cell line apoptosis assay was conducted according to a modified version of Marconi et al., Cell Death and Disease 2013. In short, fully mature enucleated reticulocytes expressing DR4.2 and DR5.2 were incubated with CFSE-labeled Raji Cells for 24 hours at a 1:1 ratio. Afterwards cells were stained with annexin V and analyzed by flow cytometry. Apoptosis percentages were determined from CFSE positive Raji cells that also stained positive for annexin V.

As shown in FIG. 1, when CFSE-labeled Raji cells were incubated with untransduced, DR4.2 transduced, DR5.2 transduced, or a mixture of DR4.2 transduced and DR5.2 transduced cultured reticulocytes, minimal cell death was observed over background. However, when CFSE-labeled Raji cells were incubated with cultured reticulocytes that had been simultaneously transduced with both DR4.2 and DR5.2 and thus express both proteins simultaneously, a significant amount of cell death was observed (equivalent to the maximal amount of TRAIL-induced apoptosis achievable in this assay with Raji cells—see, e.g. Marconi et al., Cell Death and Disease 2013). This data indicates that the coordinated action of TRAIL receptor agonists on the surface of a single engineered red blood cell is able to induce cell killing in a synergistic manner, relative to cells expressing single TRAIL receptor agonists and even a mixture of cells that each express a different TRAIL receptor agonist.

The cell population may be formulated in AS-3 additive solution and administered intravenously to a patient suffering from Burkitt's Lymphoma. It is anticipated that the patient then exhibits an improvement in his symptoms as measured by reduction in lymph node size, improvement in hepatosplenomegaly, and/or reduction of nausea and vomiting.

Example 2. Generation of Capture eRBC Comprising 5 Cytokines for Use in Treating Sepsis The genes for anti-TNFa (SEQ ID 7), anti-IL6 (SEQ ID 6), CD14 (Uniprot # P08571), IFNGR1 (Uniprot # P15260), and IL12R1 (Uniprot # P42701) are synthesized by a commercial vendor. The genes are cloned into a lentivirus vector (SBI) upstream of the gene for human glycophorin A and separated by a sequence encoding a 12-amino acid Gly-Ser (GGGSGGGSGGGS (SEQ ID NO: 19)) flexible linker and an HA epitope tag (YPYDVPDY (SEQ ID NO: 20)).

Human CD34+ cells can be cultured, and virus can be produced, as described in Example 1. Transduced cells are differentiated as described herein.

To assess the expression of the transgenes, cells are labeled simultaneously with the ligands TNFa, IL-6, IFNg, and IL-12 (purchased from Life Technologies), as well as lipopolysaccharide (ThermoFisher), that are chemically conjugated to complementary fluorescent dyes. The cells are analyzed by flow cytometry to verify that (a) the agents are all expressed on the surface of the cell and (b) the agents are capable of binding to their target ligands.

The cell population is formulated in AS-3 additive solution and administered intravenously to a patient who is developing sepsis. It is anticipated that the patient then exhibits an improvement in his symptoms as measured by a reduction in circulating cytokine levels, a reduction or prevention of vascular leak syndrome, and improved survival.

Example 3. eRBC Comprising Combinatorial Library of Tumor Antigens for Use as Cancer Vaccine Human CD34+ cells can be cultured as described in Example 1. Cells are differentiated to erythroid lineage cells as described herein.

A sample of melanoma cancer cells is isolated from a patient by biopsy. The cells are lysed and total RNA is extracted using a silica column purification (ThermoFisher), quantified for RNA content by absorbance spectroscopy, and stored at −80 C.

Four days before terminal differentiation of the red blood cell culture, cells are collected, washed twice with serum-free IMDM, and resuspended to a final concentration of $10\text{-}40 \times 10^6$ cells/mL in Opti-MEM. Subsequently, 0.5 mL of the cell suspension is mixed with 20 ug of mRNA, and electroporated in a 0.4-cm cuvette using an Easyject Plus device (EquiBio, Kent, United Kingdom) at conditions of 300V and 150 uF. After electroporation, fresh red blood cell maturation medium is added to the cell suspension and cells are further incubated at 37° C. in a humidified atmosphere supplemented with 5% CO2.

Fully mature reticulocytes are characterized for protein expression by mass spectrometric analysis of cell lysate. Non-electroporated cells and electroporated cells that are administered PBS instead of RNA are used as controls to identify endogenous reticulocyte proteins from exogenous cancer-derived proteins.

The cell population is formulated in AS-3 additive solution and administered intravenously to a patient who suffering from melanoma. It is anticipated that the patient then exhibits an immune response against the melanoma antigens, measured by reduction in metastatic masses by CT scanning and resolution of melanoma skin lesions.

Example 4: Genetic Engineering of Erythrocytes as an Anti-Tumor Therapy for Non-Hodgkin's Lymphoma (NHL)

Red blood cells were generated that express on their surface antibodies against PD-1 and PD-L1 (RCT-antiPD-1 and RCT-antiPD-L) to assess whether these cells could bind their respective targets and activate a robust immune response. Binding of RCT-antiPD-1 and RCT-antiPD-L1 to recombinant PD-1 and PD-L1, respectively was determined using flow cytometry, and was shown to be highly specific. Red blood cells were also produced which express on their surface a fusion protein comprising, from N-to-C terminus, an ipilimumab-based anti-CTLA4 scFv antibody domain, an epitope tag, and full-length GPA (extracellular, transmembrane, and cytoplasmic domains. Robust expression of anti-CTLA4 polypeptides was observed in a flow cytometry assay, with over 95.2% of cells expressed anti-CTLA4 after transfection with a vector encoding anti-CTLA4.

Functional activity was tested using an in vitro Jurkat cell IL-2 secretion assay. In this assay, IL-2 secretion is inhibited by incubating Jurkat cells with NHL cells (Z138) expressing PD-L1 induced by stimulation with CD3/CD28 tetramers. IL-2 secretion was rescued by culturing the Jurkat and Z138 cells with RCT-antiPD-1 or RCT-antiPD-L1 but not control RCT. RCT-antiCTLA4 also showed a rescue and restoration of T cell IL-2 secretion.

The ability of these engineered red blood cells to elicit activation in a standard antigen recall assay was assayed. A robust 4-6 fold increase was demonstrated in interferon-gamma secretion of peripheral blood mononuclear cells (PBMC) in an antigen recall assay. Donor PBMC were stimulated with a common flu virus antigen. Memory T cells sensitive to immune checkpoint inhibition were tested for activation and gamma interferon secretion by co-culture with RCT-antiPD-1 or RCT-antiPD-L1 in comparison to control PBMCs or control RCT.

These experiments indicate that red blood cells are capable of engaging in specific cell-cell interactions and engaging the immune checkpoint.

In addition, red blood cells expressing an anti-CD20 single chain variable fragment on their surface (RCT-antiCD20) were generated. Their ability to bind CD20+ lymphoma cells in vitro was assessed. This experiment demonstrated efficient and specific binding of RCT-antiCD20 to target cells using flow cytometry and immunofluorescent microscopy. It was also assessed whether this interaction could induce apoptosis, by co-culturing RCT-antiCD20 cells with a panel of CD20+ human lymphoma cell lines, representing lymphoma subtypes; DoHH2 (follicular lymphoma), Ramos (Burkitt's lymphoma), Granta-519 (Mantle Cell Lymphoma) and SU-DHL-4 (diffuse large B cell lymphoma). In all cases, RCT-antiCD20 co-culture resulted in increased apoptosis relative to RCT or soluble Rituximab monoclonal antibody alone. Direct tumor cell killing in vitro is hypothesized to be more effective than monoclonal antibody alone due to the hyper-crosslinking of CD20 on the lymphoma cell. This effect was shown both by in situ demonstration of receptor clustering and by a stimulation of apoptotic pathways. These findings therefore demonstrate a novel biology for proteins expressed on RCT and warranted testing for impact on lymphoma tumors in vivo.

Example 5: Capture and Modification of a Target Protein

In this Example, transgenic enucleated erythroid cells were used to capture and modify a target protein. The control cells and the experimental cells each comprise endogenous glycophorin A (GPA) in their membranes, which was used to bind the target protein. The experimental cells expressed an exogenous protein comprising surface-exposed IdeS fused to GPA as a membrane anchor. IdeS is capable of cleaving antibodies to produce a F(ab')2 fragment and a Fc fragment. The target protein is an anti-GPA antibody that is fluorescently labelled with FITC. Both the constant and variable regions of the target antibody were FITC-labelled, so that if the antibody was cleaved, both fragments could be detected.

First, the control cells and IdeS-expressing cells were tested by FACS for the ability to bind the anti-GPA antibody. Both control and IdeS-expressing cells bound the antibody as measured by association of FITC with the cells (data not shown). In addition, both control and IdeS-expressing cells bound the antibody as measured by or using a second detection method with a fluorescently labeled anti-rabbit Fc antibody (data not shown). These measurements were taken at an early timepoint, before cells were incubated to allow IdeS-mediated cleavage of the target antibody.

Figure 2:
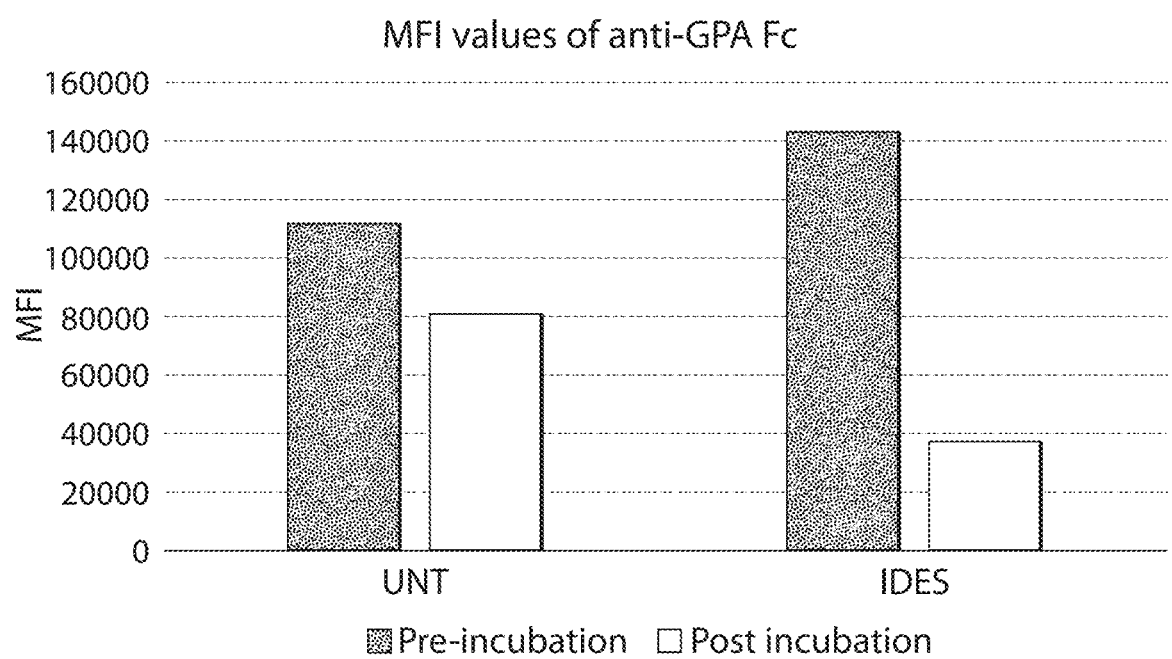
FIG. 2 is a bar graph showing the mean fluorescent intensity from control erythroid cells (UNT) or IdeS-expressing erythroid cells (IDES) labelled with an anti-Rabbit Fc fluorophore labeled antibody, before or after a 5 hour incubation.
Figure 3:
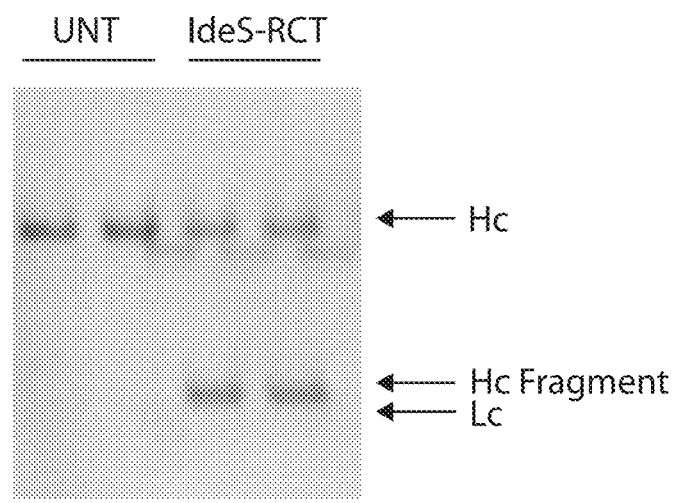
FIG. 3 is a Western blot showing intact heavy chain of target antibodies or fragments of the heavy chain in supernatant from control cells (UNT) or Ide-S expressing cells (IdeS-RCT). Arrows indicate the heavy chain (Hc), heavy chain fragment (Hc-fragment), and light chain (Lc).

In contrast, only the IdeS-expressing cells were able to cleave the target antibody. This was shown by incubating the control or IdeS-expressing cells with the target antibody to allow antibody cleavage to occur. Fluorescently labeled anti-rabbit Fc antibody was added to the reaction in order to detect intact antibodies on the surface of the erythroid cells. The IdeS-expressing cells showed a decrease in anti-rabbit Fc association with the cells (FIG. 2), indicating lower levels of Fc on the surface of the IdeS-expressing cells compared to the control cells. There was no decrease in the amount of the directly FITC-labeled target antibody associated with control cells or IdeS-expressing cells, indicating that at least the FITC-labeled variable region of the target antibody still bound the IdeS-expressing and control cells. This result was confirmed by Western blot, where anti rabbit heavy chain and anti rabbit light chain antibodies were used to detect intact and cleaved antibody in the supernatant of control or IdeS-expressing cells. The experiment showed that IdeS-expressing erythroid cells but not control erythroid cells cleaved the anti-GPA-antibody, resulting in appearance of the heavy chain fragment (FIG. 3).

Thus, the control cells were able to bind the target antibody, but only the IdeS-expressing cells were able to bind and cleave the target antibody.

Example 6: RCT-Anti-PD-L1 Promotes T Cell Proliferation

This Example demonstrates that co-culture of RCT-antiPD-L1 with PBMC has led to enhanced T-cell proliferation, based upon a 4.4 fold increase in total count of T cells following incubation with RCT-antiPD-L1 when compared to PBMCs alone.

Example 7: RCTs Expressing a Costimulatory Protein

Approaching T-cell activation from another angle, RCTs were engineered to express 41-BB-L, a co-stimulatory protein that is expressed on antigen presenting cells and binds the 41-BB receptor on T-cells (RCT-41-BB-L). Binding of RCT-41-BB-L to recombinant 41-BB was determined using flow cytometry. Co-culture of PBMCs with RCT-41-BB-L showed a 1.7 fold increase in T-cell proliferation compared to PBMCs alone. Finally, when RCT-41-BB-L were incubated with Jurkat cells overexpressing 41-BB and NFkB-Luc2P, activation of NFkB-mediated luciferase expression increased 30 fold compared to controls.

Example 8: Red Cell Therapeutics Co-Expressing Anti-CD20 and TRAIL Ligand

When erythroid cells were engineered to simultaneously express anti-CD20 as well as Trail ligand (an apoptosis inducing agent), co-culture of Ramos cells with RCT-antiCD20, RCT-Trail, and RCT-antiCD20+Trail (co-expressed) exert 32%, 47% and 76% apoptosis respectively after 48 hours, suggesting a synergistic cell-killing effect of the co-expressing RCTs.

A cell population comprising TRAIL ligand and anti-CD20 moiety may be formulated in AS-3 additive solution and administered intravenously to a patient, e.g., a patient suffering from a cancer.

---

The invention claimed is:

1. A genetically engineered enucleated erythroid cell comprising an exogenous polypeptide that comprises IL-15 or an IL15Rα-binding fragment thereof, wherein the exogenous polypeptide is at the surface of the enucleated erythroid cell, wherein the exogenous polypeptide does not comprise a sortase transfer signature, and
wherein the enucleated erythroid cell was produced by a process comprising:
introducing an exogenous nucleic acid encoding the exogenous polypeptide into a nucleated erythroid cell, or a precursor thereof; and
culturing the nucleated erythroid cell under conditions suitable for enucleation of the nucleated erythroid cell and for production of the exogenous polypeptide.

2. The genetically engineered enucleated erythroid cell of claim 1, further comprising a second exogenous polypeptide.

3. The genetically engineered enucleated erythroid cell of claim 2, wherein the second exogenous polypeptide comprises 4-1BBL or a 4-1BB-binding fragment of 4-1BBL.

4. A method of treating cancer in a subject, comprising administering to the subject a plurality of the enucleated erythroid cells of claim 1, in an amount effective to treat cancer in the subject.

5. The method of claim 4, wherein the cancer is a leukemia, a lymphoma, or a solid tumor.

6. The method of claim 4, further comprising administering an anti-neoplastic drug to the subject.

7. The method of claim 6, wherein the anti-neoplastic drug is chosen from a chemotherapeutic drug, a cancer growth blocker, a cancer vaccine, and a hormone therapy.

8. A method of stimulating a T cell, comprising contacting the T cell with the enucleated erythroid cell of claim 1, thereby stimulating the T cell.

9. A method of making a genetically engineered enucleated erythroid cell comprising an exogenous polypeptide that comprises IL-15 or an IL15Ra-binding fragment thereof, wherein the exogenous polypeptide is at the surface of the enucleated erythroid cell, wherein the exogenous polypeptide does not comprise a sortase transfer signature, and
wherein the method comprises:
introducing an exogenous nucleic acid encoding the exogenous polypeptide into a nucleated erythroid cell, or a precursor thereof; and
culturing the nucleated erythroid cell under conditions suitable for enucleation of the nucleated erythroid cell and for production of the exogenous polypeptide,
thereby making the enucleated erythroid cell.

10. The enucleated erythroid cell of claim 3, wherein the exogenous polypeptide and the second exogenous polypeptide have an abundance ratio of from about 2:1 to 1:2 by copy number.

11. The enucleated erythroid cell of claim 1, which is a reticulocyte.

12. The enucleated erythroid cell of claim 1, wherein the enucleated erythroid cell exhibits substantially the same osmotic membrane fragility as a corresponding isolated, unmodified, uncultured enucleated erythroid cell.

13. The enucleated erythroid cell of claim 1, which is not a hypotonically loaded cell.

14. The enucleated erythroid cell of claim 1, which is capable of promoting T cell proliferation.

15. The enucleated erythroid cell of claim 1, wherein the exogenous polypeptide further comprises a transmembrane domain.

16. The enucleated erythroid cell of claim 15, wherein the transmembrane domain comprises a glycophorin A (GPA) transmembrane domain.

17. The enucleated erythroid cell of claim 1, which is a mature red blood cell.

18. The enucleated erythroid cell of claim 1, wherein culturing the nucleated erythroid cell comprises expanding the nucleated erythroid cell by at least 1,000 fold.

* * * * *

UNITED STATES PATENT AND TRADEMARK OFFICE
CERTIFICATE OF CORRECTION

PATENT NO. : 10,568,910 B2
APPLICATION NO. : 15/906873
DATED : February 25, 2020
INVENTOR(S) : Avak Kahvejian et al.

Page 1 of 1

It is certified that error appears in the above-identified patent and that said Letters Patent is hereby corrected as shown below:

In the Claims

At Column 74, Claim number 9, Line number 34, delete "IL15Ra-binding" and insert --IL15Rα-binding--.

Signed and Sealed this
Nineteenth Day of May, 2020

Andrei Iancu
*Director of the United States Patent and Trademark Office*

SEQUENCE LISTING

```
<160> NUMBER OF SEQ ID NOS: 20

<210> SEQ ID NO 1
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220
```

```
Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 2
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Arg Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

```
<210> SEQ ID NO 3
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Asn Ile Ser Pro
            100                 105                 110

Leu Val Arg Glu Arg Gly Pro Gln Arg Val Ala Ala His Ile Thr Gly
            115                 120                 125

Thr Arg Arg Arg Ser Asn Thr Leu Ser Ser Pro Asn Ser Lys Asn Glu
130                 135                 140

Lys Ala Leu Gly Ile Lys Ile Asn Ser Trp Glu Ser Ser Arg Arg Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Asp Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

```
<210> SEQ ID NO 4
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 4

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met His His Glu Ala
            260                 265                 270

Ser Phe Phe Gly Ala Phe Leu Val Gly
        275                 280

<210> SEQ ID NO 5
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60
```

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Arg Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met His His Glu Ala
            260                 265                 270

Ser Phe Phe Gly Ala Phe Leu Val Gly
        275                 280

<210> SEQ ID NO 6
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Gly Lys Gly Leu Glu Trp Val
        35                  40                  45

Ala Gln Met Arg Asn Lys Asn Tyr Gln Tyr Gly Thr Tyr Tyr Ala Glu
    50                  55                  60

Ser Leu Glu Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Ser Tyr Tyr Gly Phe Thr Ser Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

```
Ser Leu Ser Ala Ser Val Gly Asp Arg Val Thr Ile Thr Cys Gln Ala
145                 150                 155                 160

Ser Gln Asp Ile Gly Ile Ser Leu Ser Trp Tyr Gln Gln Lys Pro Gly
                165                 170                 175

Lys Ala Pro Lys Leu Leu Ile Tyr Asn Ala Asn Asn Leu Ala Asp Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln His Asn Ser Ala Pro Tyr Thr Phe Gly Gln Gly Thr Lys Leu Glu
225                 230                 235                 240

Ile Lys Arg
```

```
<210> SEQ ID NO 7
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Gly Ile Arg Asn Tyr Leu Ala Trp Tyr Gln Gln Lys Pro
                165                 170                 175

Gly Lys Ala Pro Lys Leu Leu Ile Tyr Ala Ala Ser Thr Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Val Ala Thr Tyr Tyr Cys
    210                 215                 220

Gln Arg Tyr Asn Arg Ala Pro Tyr Thr Phe Gly Gln Gly Thr Lys Val
225                 230                 235                 240

Glu Ile Lys
```

```
<210> SEQ ID NO 8
<211> LENGTH: 312
<212> TYPE: PRT
<213> ORGANISM: Homo sapiens

<400> SEQUENCE: 8

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Lys
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Glu Lys Ile Glu Ala Tyr Leu Lys Lys His Pro Asp Lys Gln
                85                  90                  95

Lys Ile Met Phe Gly Asp Gln Glu Leu Leu Asp Val Arg Lys Val Ile
            100                 105                 110

Asn Thr Lys Gly Asp Gln Thr Asn Ser Glu Leu Phe Asn Tyr Phe Arg
        115                 120                 125

Asp Lys Ala Phe Pro Gly Leu Ser Ala Arg Arg Ile Gly Val Met Pro
    130                 135                 140

Asp Leu Val Leu Asp Met Phe Ile Asn Gly Tyr Tyr Leu Asn Val Tyr
145                 150                 155                 160

Lys Thr Gln Thr Thr Asp Val Asn Arg Thr Tyr Gln Glu Lys Asp Arg
                165                 170                 175

Arg Gly Gly Ile Phe Asp Ala Val Phe Thr Arg Gly Asp Gln Ser Lys
            180                 185                 190

Leu Leu Thr Ser Arg His Asp Phe Lys Glu Lys Asn Leu Lys Glu Ile
        195                 200                 205

Ser Asp Leu Ile Lys Lys Glu Leu Thr Glu Gly Lys Ala Leu Gly Leu
    210                 215                 220

Ser His Thr Tyr Ala Asn Val Arg Ile Asn His Val Ile Asn Leu Trp
225                 230                 235                 240

Gly Ala Asp Phe Asp Ser Asn Gly Asn Leu Lys Ala Ile Tyr Val Thr
                245                 250                 255

Asp Ser Asp Ser Asn Ala Ser Ile Gly Met Lys Lys Tyr Phe Val Gly
            260                 265                 270

Val Asn Ser Ala Gly Lys Val Ala Ile Ser Ala Lys Glu Ile Lys Glu
        275                 280                 285

Asp Asn Ile Gly Ala Gln Val Leu Gly Leu Phe Thr Leu Ser Thr Gly
    290                 295                 300

Gln Asp Ser Trp Asn Gln Thr Asn
305                 310

<210> SEQ ID NO 9
<211> LENGTH: 131
<212> TYPE: PRT
<213> ORGANISM: Homo sapiens
```

-continued

<400> SEQUENCE: 9

Leu Ser Thr Thr Glu Val Ala Met His Thr Ser Thr Ser Ser Val
1               5                  10                  15

Thr Lys Ser Tyr Ile Ser Ser Gln Thr Asn Asp Thr His Lys Arg Asp
            20                  25                  30

Thr Tyr Ala Ala Thr Pro Arg Ala His Glu Val Ser Glu Ile Ser Val
        35                  40                  45

Arg Thr Val Tyr Pro Pro Glu Glu Glu Thr Gly Glu Arg Val Gln Leu
    50                  55                  60

Ala His His Phe Ser Glu Pro Glu Ile Thr Leu Ile Ile Phe Gly Val
65                  70                  75                  80

Met Ala Gly Val Ile Gly Thr Ile Leu Leu Ile Ser Tyr Gly Ile Arg
                85                  90                  95

Arg Leu Ile Lys Lys Ser Pro Ser Asp Val Lys Pro Leu Pro Ser Pro
            100                 105                 110

Asp Thr Asp Val Pro Leu Ser Ser Val Glu Ile Glu Asn Pro Glu Thr
        115                 120                 125

Ser Asp Gln
    130

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Ser Gly Gly Ser Gly Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Ser Gly Gly Gly Ser
1               5

<210> SEQ ID NO 12
<211> LENGTH: 19
<212> TYPE: PRT
<213> ORGANISM: Homo sapiens

<400> SEQUENCE: 12

Met Tyr Gly Lys Ile Ile Phe Val Leu Leu Leu Ser Glu Ile Val Ser
1               5                  10                  15

Ile Ser Ala

<210> SEQ ID NO 13
<211> LENGTH: 16
<212> TYPE: PRT
<213> ORGANISM: Homo sapiens

```
<400> SEQUENCE: 13

Cys Pro Pro Cys Pro Ala Pro Glu Leu Leu Gly Gly Pro Ser Val Phe
1               5                   10                  15

<210> SEQ ID NO 14
<211> LENGTH: 15
<212> TYPE: PRT
<213> ORGANISM: Homo sapiens

<400> SEQUENCE: 14

Cys Pro Pro Cys Pro Ala Pro Pro Val Ala Gly Pro Ser Val Phe
1               5                   10                  15

<210> SEQ ID NO 15
<211> LENGTH: 16
<212> TYPE: PRT
<213> ORGANISM: Homo sapiens

<400> SEQUENCE: 15

Cys Pro Arg Cys Pro Ala Pro Glu Leu Leu Gly Gly Pro Ser Val Phe
1               5                   10                  15

<210> SEQ ID NO 16
<211> LENGTH: 16
<212> TYPE: PRT
<213> ORGANISM: Homo sapiens

<400> SEQUENCE: 16

Ala His His Ala Gln Ala Pro Glu Phe Leu Gly Gly Pro Ser Val Phe
1               5                   10                  15

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 17

Leu Pro Xaa Thr Gly
1               5

<210> SEQ ID NO 18
<211> LENGTH: 93
<212> TYPE: PRT
<213> ORGANISM: Homo sapiens

<400> SEQUENCE: 18

Val Ser Asp Val Pro Arg Asp Leu Glu Trp Ala Ala Thr Pro Thr Ser
1               5                   10                  15

Leu Leu Ile Ser Trp Asp Ala Pro Ala Val Thr Val Arg Tyr Tyr Arg
                20                  25                  30

Ile Thr Tyr Gly Glu Thr Gly Gly Asn Ser Pro Val Gln Glu Phe Thr
            35                  40                  45

Val Pro Gly Ser Lys Ser Thr Ala Thr Ile Ser Gly Leu Lys Pro Gly
        50                  55                  60
```

-continued

```
Val Asp Tyr Thr Ile Thr Gly Tyr Ala Val Thr Gly Arg Gly Asp Ser
 65                  70                  75                  80

Pro Ala Ser Ser Lys Pro Ile Ser Ile Asn Tyr Arg Thr
                 85                  90

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Ser Gly Gly Gly Ser Gly Gly Gly Ser
 1               5                  10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Pro Tyr Asp Val Pro Asp Tyr
 1               5
```